(12) United States Patent
Matsui et al.

(10) Patent No.: US 6,495,533 B1
(45) Date of Patent: Dec. 17, 2002

(54) DRUGS CONTAINING PHOSPHORIC ACID DERIVATIVES AS THE ACTIVE INGREDIENT

(75) Inventors: Toshiaki Matsui, Osaka (JP); Nagashige Omawari, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/914,016

(22) PCT Filed: Feb. 22, 2000

(86) PCT No.: PCT/JP00/01005
§ 371 (c)(1),
(2), (4) Date: Aug. 22, 2001

(87) PCT Pub. No.: WO00/50429
PCT Pub. Date: Aug. 31, 2000

(30) Foreign Application Priority Data

Feb. 23, 1999 (JP) ............................................. 11-044840
Oct. 4, 1999 (JP) ............................................. 11-283104

(51) Int. Cl.[7] ............................ A61K 31/66; L07F 9/02
(52) U.S. Cl. ....................... 514/120; 514/127; 514/129; 558/170; 558/208
(58) Field of Search ................................ 514/120, 127, 514/129; 558/170, 208; 562/23

(56) References Cited

U.S. PATENT DOCUMENTS 5,610,176 A    3/1997    Horwell et al.

FOREIGN PATENT DOCUMENTS

WO    WO 99/15162    4/1999

OTHER PUBLICATIONS

O Helen Chan et al., Evaluation of a Targeted Prodrug Strategy to Enhance Oral Absorption of Poorly Water–Soluble Compounds, Pharm. Res., vol. 15, No. 7, 1998, pp. 1012–1018.

Craig A. Townsend, Improved Asymmetric Synthesis of (–)–3–Aminonocardicinic Acid and Further Observations of the Mitsunobu Reaction for 2–Lactam Formation in Seryl Peptides, Tetrahedron Letters, vol. 23, No. 46, 1982, pp. 4859–4862.

A Wissner et al., Analogues of Platelet Activating Factor. 4.[1] Some Modifications of the Phosphocholine Moiety, J. Med. Chem.,. Soc. 1986, vol. 29, No. 3, pp. 328–333.

Craig A. Townsend et al., Nocardicin A: Stereochemical and Biomimetic Studies of Monocyclic β–Lactam Formation, J. Amer. Chem.Soc. 1983, vol. 105, No. 4, pp. 919–927.

European Search Report dated Mar. 4, 2002.

Thomas G. Mayer et al., Synthesis of a GPI Anchor of Yeast, Angew. Chem. Int. Ed. Engl., 1994, vol. 106, No. 21, pp. 2176–2181.

Hiroaki Suga et al., Esterolytic Antibodies Induced to Haptens with a 1,2–Amino Alcohol Functionality, J. Am. Chem. Soc., 1994, vol. 116, No. 2, pp. 487–494.

International Search Report dated Jun. 19, 2000.

*Primary Examiner*—T. A. Solola
*Assistant Examiner*—Joseph Murray
(74) *Attorney, Agent, or Firm*—Sughrue Mion, PLLC

(57) ABSTRACT

The present invention relates to phosphoric acid derivatives represented by general formula (I), wherein each symbol is as defined in the description and nontoxic salts thereof.

Because of having a TNFα production inhibitory effect, the compounds represented by general formula (I) are useful as preventives and/or remedies for rheumatoid arthritis, ulcerative colitis, Crohn's disease, hepatitis, sepsis, hemorrhagic shock, multiple sclerosis, cerebral infarction, diabetes, interstitial pneumonia, uveitis, pain, glomerulonephritis, HIV-associated diseases, cachexia, myocardial infarction, chronic heart failure, oral aphtha, Hansen's disease, infection, etc.

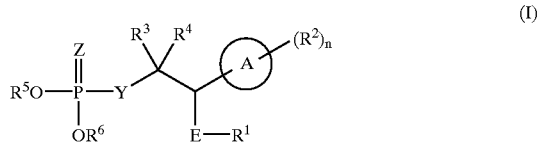

(I)

15 Claims, No Drawings

US 6,495,533 B1

DRUGS CONTAINING PHOSPHORIC ACID DERIVATIVES AS THE ACTIVE INGREDIENT

The Instant Application is a 371 of PCT/JP00/01005 filed Feb. 22, 2000.

TECHNICAL FIELD

This invention relates to phosphoric acid derivatives. More particularly, this invention relates to
1) phosphoric acid derivatives of the formula (I)

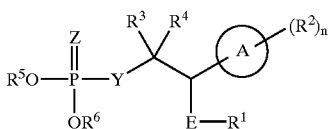

(I)

wherein all symbols are the same meaning as hereinafter defined and non-toxic salts thereof,
2) processes for the preparation thereof, and
3) pharmaceutical compositions containing them as active ingredient.

BACKGROUND

Tumor necrosis factor a (TNFα) was discovered found as a factor that induces tumor hemorrhagic necrosis. TNFα is produced by macrophages as well as various other cells, including lymphocytes (CD4+ T cells, CD8+ T cells, B cells), neutrophils, stellate cells, endothelial cells and smooth muscle cells. TNFα showed various physiological activities by affecting various cells. TNFα is believed to play an important role especially in inflammatory reactions as a biophylactic response. Macrophages and neutrophils are deeply involved in development and progress of inflammatory reaction. TNFα stimulates vulnerary activities of macrophages and increases release of inflammatory cytokines, including TNFα, interleukin-1 (IL-1), interleukin-6 (IL-6) and interleukin-8 (IL-8) etc. Also TNFα is associated with activation of neutrophils such as phagocytosis, degranulation, chemotaxis and expression of adhesion molecules and enhances production of platelet activating factor and active oxygen by neutrophils. TNFα stimulates growth, induction of interleukin-2 (IL-2) receptor and production of interferon γ and colony-stimulating factor in T cells, which play an important role in immune response. Besides TNFα provides help to B lymphocytes for antibody production and cell division.

It is reported below that TNFα is involved in variety of diseases. p0 (1) It may be a cause of fulminant hepatitis that TNFα levels in serum of the patients with fulminant hepatitis were higher than that of the patients with the severe form of acute hepatitis [H. Iwai et. al., Crit. Care. Med., 26, 873 (1998)].
(2) TNFα contents in intestinal mucosa from inflammatory bowel disease were markedly increased [Z. Kmiec, Arch. Immunol. Ther. Exp., 4, 143 (1998)].
(3) In the patients with Crohn's disease, anti TNFα antibody was effective endoscopically [D. W. Hommes et. al., Haemostasis, 27, 269 (1997)].
(4) There was a correlation between TNFα and glucose level in serum of the patients with insulin dependent diabetes [M. Muc-Wierzgon et. al., Pol. Arch. Med. Wewn., 97, 426 (1998)].
(5) In the patients with interstitial pneumonia, ability to produce TNFα by alveolar macrophages are enhanced than in controls [J. Ancochea et. al., Arch. Bronconeumol., 33, 335 (1997)].
(6) Anti-TNFα antibody was effective on experimental autoimmune uveitis in mice [G. Sartani et. al., Invest. Ophthalmol. Vis. Sci., 37, 2211 (1996)].
(7) Thalidomide, which is a TNFα production inhibitor, diminished mechanical allodynia and thermal hyperalgesia in bennet model and improved the pathologic vascular injury [C. Sommer et. al., Pain, 74, 83 (1998)].
(8) Thalidomide was effective for diarrhea and weight loss in HIV patients [D. Sharpstone et. al., Gastroenterol, 112, 1823 (1997)].
(9) Anti-TNFα antibody reduced infarct volume in middle cerebral artery ischemia-reperfusion model [G. Yang et. al., Neuroreport, 9, 2131 (1998)].

Therefore inhibitors of TNFα production may be considered useful as preventives and/or remedies of various diseases induced by inflammatory cytokines including TNFα. In view of physiological activity and involvement of TNFα with diseases, these inhibitors may be useful for rheumatoid arthritis, ulcerative colitis, Crohn's disease, hepatitis, sepsis, hemorrhagic shock, multiple sclerosis, cerebral infarction, diabetes, interstitial pneumonia, uveitis, pain, glomerulonephritis, HIV-associated diseases, cachexia, myocardial infarction, chronic heart failure, oral aphtha, Hansen's disease, infection, etc.

RELATED ARTS

For example, it is disclosed in JP kokai 55-118494 that the phosphorylcholine type compound of the formula (A)

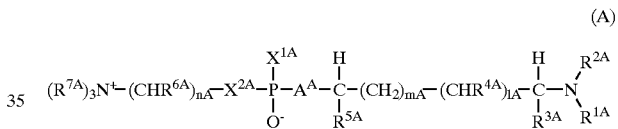

(A)

wherein $R^{1A}$ and $R^{2A}$ are the same or different to represent hydrogen atom, optionally substituted by alkyl, alkenyl, aralkyl, aryl, acyl, alkoxycarbonyl, alkoxycarbonylalkyl, aralkoxycarbonyl, alkoxycarbonylaminoalkyl, carbamoyl, thiocarbamoyl, or heterocyclic ring, $R^{3A}$ and $R^{5A}$ are the same or different to represent hydrogen atom, carboxyl, optionally substituted by alkyl, alkenyl, aralkyl, aryl, alkoxycarbonyl, or heterocyclic ring, $R^{4A}$ represents hydrogen atom, alkyl, alkenyl, aralkyl, or aryl etc., $A^A$ represents oxygen atom, sulfur atom, or —$NR^{8A}$— (wherein $R^{8A}$ repersents hydrogen atom, etc.), $R^{6A}$ is the same or different to represent hydrogen atom, or optionally substituted by alkyl, aralkyl, $R^{7A}$ represents alkyl, aralkyl, $X^{1A}$ and $X^{2A}$ represent oxygen atom or sulfur atom, $l^A$ and $m^A$ each, is 0, 1 or 2, and $n^A$ is 2 or 3 is useful as antitumor agent.

It is disclosed in WO 96/22966 that the compound of the formula (B)

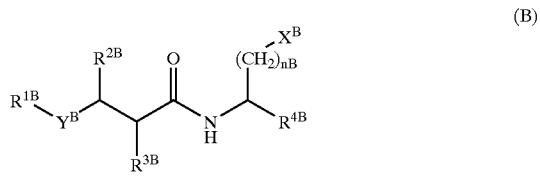

(B)

wherein $X^B$ represents —COOH, —$P^-O_3H$, —$SO_2R^{5B}$, —$SO_3H$, —$OP^-O_3H$, —$COOR^{4B}$ or —$CON(R^{4B})_2$, $Y^B$ repersents —CO—, —$SO_2$—, or —$PO_2$—, $R^{1B}$ represents alkyl, alkenyl, alkynyl, cycloalkyl, aryl, or heterocyclyl etc., $R^{2B}$ represents hydrogen atom, aryl, alkyl, alkenyl, alkynyl, or cycloalkyl etc., $R^{3B}$ represents alkyl, alkenyl, alkynyl, cycloalkyl, or heterocyclyl etc., or $R^{2B}$ and $R^{3B}$, taken together with the atom to which they are attached, represent heterocyclyl, $R^{4B}$ represents aryl, alkyl, or cycloalkyl etc., and $n^B$ is 0, 1 or 2 is useful as a cell adhesion inhibitor.

PURPOSE OF THE INVENTION

Energetic investigations have been carried out to find new compounds having TNFα production inhibitory activity. As a result, the present inventor have found that these aims may be accomplished by a phosphoric acid derivatives of the formula (I).

The phosphoric acid derivatives of the formula (I) have not been known as TNFα production inhibitor at all.

DISCLOSURE OF THE INVENTION

The present invention relates to
1) Phosphoric acid derivatives of the formula (I)

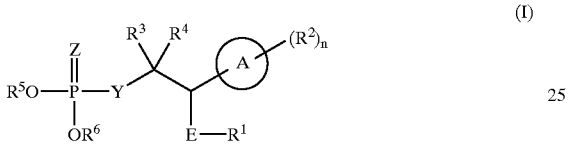

wherein $R^1$ is
(1) C1–20 alkyl,
(2) C1–20 alkyl which one carbon atom is replaced by an oxygen atom, a sulfur atom, —S(O)— or S(O)$_2$— (with the proviso that, a carbon atom which attached with E is not replaced by these groups),
(3) C2–20 alkenyl,
(4) C2–20 alkynyl,
(5) Cyc$^1$ (wherein Cyc$^1$ is C5–15 membered mono-, bi- or tricarbocyclic ring or 5–15 membered mono-, bi- or tricyclic hetero ring containing 1–4 nitrogen atoms, 1–2 oxygen atoms and/or one sulfur atom),
(6) C1–20 alkyl, C2–20 alkenyl or C2–20 alkynyl substituted by Cyc$^1$ (wherein all symbols are the same meaning as hereinbefore defined), Cyc$^1$ may be substituted by one or more substituents selected from the following (a)–(r):
(a) C1–8 alkyl,
(b) C1–8 alkoxy,
(c) nitro,
(d) halogen atom,
(e) trifluoromethyl,
(f) trifluoromethyloxy,
(g) hydroxy,
(h) cyano,
(i) NR$^{10}$R$^{11}$ (wherein R$^{10}$ and R$^{11}$ each, independently, is a hydrogen atom, C1–8 alkyl, C1–8 hydroxyalkyl, C2–5 acyl or C1–8 alkylsulfonyl),
(j) COOR$^{20}$ (wherein R$^{20}$ is a hydrogen atom or C1–4 alkyl),
(k) CONR$^{30}$R$^{31}$ (wherein R$^{30}$ and R$^{31}$ each, independently, is a hydrogen atom or C1–4 alkyl),
(l) —S(O)$_m$—R$^{32}$ (wherein m is 0, 1 or 2, R$^{32}$ is 1–8 alkyl or C1–8 alkyl substituted by C1–8 alkoxy, COOR$^{20}$ (wherein R$^{20}$ is the same meaning as hereinbefore defined) or CONR$^{30}$R$^{31}$ (wherein R$^{30}$ and R$^{31}$ each, independently, is a hydrogen atom or C1–4 alkyl)),
(m) —O—Cyc$^2$ (wherein Cyc$^2$ is C3–8 cycloalkyl or phenyl),
(n) —S—Cyc$^2$ (wherein Cyc$^2$ is the same meaning as hereinbefore defined),
(o) C1–8alkyl substituted by one substituent selected from C1–8 alkoxy, COOR$^{20}$ (wherein R$^{20}$ is the same meaning as hereinbefore defined), CONR$^{30}$R$^{31}$ (wherein R$^{30}$ and R$^{31}$ are the same meaning as hereinbefore defined), phenyl or hydroxy.
(p) C1–8alkoxy substituted by one substituent selected from C1–8 alkoxy, COOR$^{20}$ (wherein R$^{20}$ is the same meaning as hereinbefore defined), CONR$^{30}$R$^{31}$ (wherein R$^{30}$ and R$^{31}$ are the same meaning as hereinbefore defined), phenyl or hydroxy,
(q) C3–15 membered mono-, bi- or tricarbocyclic ring,
(r) 5–15 membered mono-, bi- or tricyclic hetero ring containing 1–4 nitrogen atoms, 1–2 oxygen atoms and/or one sulfur atom, E is
(a) —NR$^7$CO—,
(b) —NR$^7$SO$_2$—,
(c) —NR$^7$CONR$^8$—,
(d) —NR$^7$COO—,
(e) —CONR$^7$—,
(f) —NR$^7$CS—,
(g) —NR$^7$CSNR$^8$—,
(h) —NR$^7$CS—O—,
(i) —CSNR$^7$— or
(j) —NR$^7$— (wherein R$^7$ and R$^8$ each, independently, is a hydrogen or C1–4 alkyl), A ring is C3–15 membered mono-, bi- or tricarbocyclic ring or 5–15 membered mono-, bi- or trycyclic hetero ring containing 1–4 nitrogen atoms, 1–2 oxygen atoms and/or one sulfur atom, $R^2$ is the same meaning as hereinbefore defined substituents (a)–(r), $R^3$ and $R^4$
i) each, independently, is a hydrogen atom, C1–8 alkyl, C1–8 alkoxy, C1–8 hydroxyalkyl or phenyl, or
ii) taken together represents C2–6 alkylene, or
iii) one of $R^3$ or $R^4$, taken together with $R^2$, represent C1–5 alkylene, and the other one is a hydrogen atom, C1–8alkyl or C1–8alkoxy, n is an integer of 0, 1 or more, $R^5$ and $R^6$ each, independently, is a hydrogen atom, C1–8 alkyl, phenyl, C1–4 alkyl substituted by phenyl, C1–4 alkyl substituted by cyano or C1–4 alkyl substituted by trihalomethyl, Y and Z each, independently, is an oxygen atom or a sulfur atom, with the proviso that,
(1) when n is 2 or more integer, then $R^2$ is the same or different,
(2) when $R^1$ and $R^2$ represent contains a sulfur atom, then Y is an oxygen atom, and $R^1$ and $R^2$ do not represent contains a sulfur atom at the same time or a non-toxic salt thereof,
2) processes for the preparation thereof, and
3) pharmaceutical composition containing them as active ingredient.

In the present specification, C1–4 alkyl means methyl, ethyl, propyl, butyl and isomers thereof.

In the present specification, C1–8 alkyl means methyl, ethyl, propyl, butyl, pentyl, hexyl, heptyl, octyl and isomers thereof.

In the present specification, C1–20 alkyl means methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and isomers thereof.

In the present specification, C2–20 alkenyl means vinyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, butadienyl, pentadienyl, hexadienyl, heptadienyl, octadienyl, nonadienyl, decadienyl, undecadienyl, dodecadienyl, tridecadienyl, tetradecadienyl, pentadecadienyl, hexadecadienyl, heptadecadienyl, octadecadienyl, nonadecadienyl, icosadienyl, hexatrienyl, heptatrienyl, octatrienyl, nonatrienyl, decatrienyl, undecatrienyl, dodecatrienyl, tridecatrienyl, tetradecatrienyl, pentadecatrienyl, hexadecatrienyl, heptadecatrienyl, octadecatrienyl, nonadecatrienyl, icosatrienyl and isomers thereof.

In the present specification, C2–20 alkynyl means ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, icosynyl, butadiynyl, pentadiynyl, hexadiynyl, heptadiynyl, octadiynyl, nonadiynyl, decadiynyl, undecadiynyl, dodecadiynyl, tridecadiynyl, tetradecadiynyl, pentadecadiynyl, hexadecadiynyl, heptadecadiynyl, octadecadiynyl, nonadecadiynyl, icosadiynyl, hexatriynyl, heptatriynyl, octatriynyl, nonatriynyl, decatriynyl, undecatriynyl, dodecatriynyl, tridecatriynyl, tetradecatriynyl, pentadecatriynyl, hexadecatriynyl, heptadecatriynyl, octadecatriynyl, nonadecatriynyl, icosatriynyl and isomers thereof.

In the present specification, C1–8 alkoxy means methoxy, ethoxy, propoxy, butoxy, pentyloxy, hexyloxy, heptyloxy, octyloxy and isomers thereof.

In the present specification, C1–5 alkylene means methylene, ethylene, trimethylene, tetramethylene, pentamethylene and isomers thereof.

In the present specification, C2–6 alkynene means ethylene, trimethylene, tetramethylene, pentamethylene, hexamethylene and isomers thereof.

In the present specification, C2–5 acyl means acetyl, propionyl, butyryl, valeryl and isomers thereof.

In the present specification, a halogen atom is chlorine, bromine, fluorine or iodine.

In the present specification, C3–8 cycloalkyl means cyclopropyl, cyclobutyl, cyclopentyl, cyclohexyl, cycloheptyl and cyclooctyl.

In the present specification, C1–8 hydroxyalkyl means hydroxymethyl, hydroxyethyl, hydroxypropyl, hydroxybutyl, hydroxypentyl, hydroxyhexyl, hydroxyheptyl, hydroxyoctyl and isomers thereof.

In the present specification, C1–4 alkyl substituted by phenyl means phenylmethyl, phenylethyl, phenylpropyl and phenylbutyl.

In the present specification, C1–4 alkyl substituted by cyano means cyanomrethyl, cyanoethyl, cyanopropyl and cyanobutyl.

In the present specification, C1–4 alkyl substituted by trihalomethyl means methyl, ethyl, propyl or butyl substituted by trifluoromethyl, trichloromethyl, tribromomethyl or triiodomethyl.

In the present specification, C3–15 membered mono-, bi- or tricarbocyclic ring includes a C3–15 membered mono-, bi- or tricarbocyclic aryl, partially saturated or fully saturated one; for example, cyclopropane, cyclobutane, cyclopentane, cyclohexane, cycloheptane, cyclopentene, cyclohexene, cyclopentadiene, cyclohexadiene, benzene, pentalene, indene, naphthalene, azulene, fluorene, phenanthrene, anthracene, acenaphthylene, biphenylene, perhydropentalene, perhydroindene, perhydronaphthalene, perhydroazulene, perhydrofluorene, perhydrophenanthrene, perhydroanthracene, perhydroacenaphthylene, perhydrobiphenylene, adamantane etc.

In the present specification, 5–15 membered mono-, bi- or tricyclic heterocyclic ring containing 1–4 of nitrogen, 1–2 of oxygen and/or 1 of sulfur includes 5–15 membered mono-, bi- or tricyclic heterocyclic aryl, partially saturated or fully saturated one containing 1–4 of nitrogen, 1–2 of oxygen and/or 1 of sulfur.

Above-mentioned 5–15 membered mono-, bi- or tricyclic heterocyclic aryl containing 1–4 of nitrogen, 1–2 of oxygen and/or 1 of sulfur represents pyrrole, imidazole, triazole, tetrazole, pyrazole, pyridine, pyrazine, pyrimidine, pyridazine, azepine, diazepine, furan, pyran, oxepin, oxazepine, thiophene, thiin (thiopyran), thiepin, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzimidazole, carbazole, acridine, etc.

Above-mentioned 5–15 membered mono-, bi- or tricyclic heterocyclic ring which is partially saturated or fully saturated, containing 1–4 of nitrogen, 1–2 of oxygen and/or 1 of sulfur represents pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydrofuran, tetrahydrofuran, dihydropyran, tetrahydropyran, dihydrothiophene, tetrahydrothiophene, dihydrothiine (dihydrothiopyran), tetrahydrothiine (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, benzoxazepine, benzoxadiazepine, benzothiazepine, benzothiadiazepine, benzazepine, benzodiazepine, indoloxazepine, indolotetrahydrooxazepine, indolooxadiazepine, indolotetrahydrooxadiazepine, indolothiazepine, indolotetrahydrothiazepine, indolothiadiazepine, indolotetrahydrothiadiazepine, indoloazepine, indolotetrahydroazepine, indolodiazepine, indolotetrahydrodiazepine, benzofurazan, benzothiadiazole, benzotriazole, camphor, imidazothiazole, dihydrocarbazole, tetrahydrocarbazole, perhydrocarbazole, dihydroacridine, tetrahydroacridine, perhydroacridine, dioxolane, dioxane, dioxazine, etc.

In the present invention, as may be easily understood by those skilled n the art, the symbol:

indicates that the substituent attached thereto is in front of the sheet (β-position), unless otherwise specified, the symbol:

indicates that the substituent attached thereto is behind the sheet (α-position), unless otherwise specified, the symbol:

indicates that the substituent attached thereto is β-position or α-position (though it is single isomer that it attached thereto is either β-position or α-position, the structure is not determined), the symbol:

indicates the mixture of the compounds that the substituent attached thereto is β-position and α-position.

In the formula (I), ring A is preferably C3–15 membered mono-, bi- or tricarbocyclic ring, more preferably C3–7 membered monocarbocyclic ring, even more preferably benzene, cyclopentane, cyclohexane or cycloheptane, most preferably benzene.

In the formula (I), $R^3$ and $R^4$ are preferably that each, independently, is hydrogen atom or C1–8 alkyl, more preferably C1–4 alkyl, and most preferably that each, independently, is hydrogen atom and methyl.

In the formula (I), when one of $R^3$ and $R^4$ is a hydrogen atom and the ther is not a hydrogen atom, then the former is preferably attached to the α-position (behind the sheet), and the latter is preferably attached to the β-position (in front of the sheet).

In the formula (I), E is preferably —$NR^7CO$—, —$NR^7SO_2$—, —$NR^7CONR^8$—, or —$NR^7COO$—, more preferably —$NR^7CO$— or —$NR^7COO$— (wherein all symbols are the same meaning as hereinbefore defined), and most preferably —NHCO— or —NHCOO—.

In the formula (I), E may be attached α-position or β-position, preferably β-position (in front of the sheet).

In the formula (I), $R^1$ is preferably C1–20 alkyl, more preferably C5–10 alkyl, and most preferably heptyl.

In the formula (I), $R^2$ is prepreably C1–8 alkyl, C1–8 alkoxy, C1–8 alkylthio or $COOR^{20}$ ($R^{20}$ is the same meaning as hereinbefore defined), more preferably C1–4 alkoxy, C1–4 alkylthio, $COOR^{200}$ ($R^{200}$ is C1–4alkyl), and most preferably methoxy, isopropyloxy, methylthio or methoxycarbonyl.

In the formula (I), when benzene ring is substituted by $R^2$, then the position of substitution is preferably 3-position.

In the formula (I), n is preferably 0–5, and more preferably 0–2.

Concretely, the compounds that hereinafter described in the examples and the compounds in the following tables 1–89 are preferably. Besides, in the following tables, the numbers described before each group represent the position of substitution, Me is methyl group, Et is ethyl group, Ph is phenyl group and Py is pyridyl group.

TABLE 1

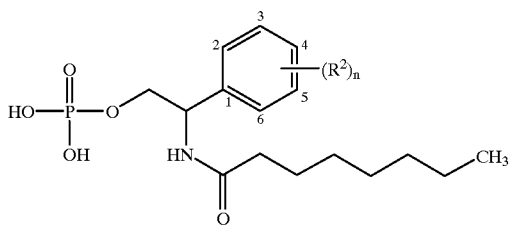

(I-A)

| No. | $(R^2)_n$ |
|---|---|
| 1 | H |
| 2 | 2-Me |
| 3 | 3-Me |
| 4 | 4-Me |
| 5 | 3,4-di-Me |
| 6 | 3,5-di-Me |
| 7 | 2,4,6-tri-Me |
| 8 | 2-OMe |
| 9 | 3-OMe |
| 10 | 4-OMe |
| 11 | 3,4-di-OMe |
| 12 | 3,5-di-OMe |
| 13 | 2,4,6-tri-OMe |
| 14 | 3-Me-5-OMe |
| 15 | 3,4-di-Me, 5-OMe |
| 16 | 2-$NO_2$ |
| 17 | 3-$NO_2$ |
| 18 | 4-$NO_2$ |
| 19 | 2-F |
| 20 | 3-F |
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |
| 30 | 3-OMe, 5-F |
| 31 | 3-$CF_3$ |
| 32 | 4-$CF_3$ |
| 33 | 3-Me, 5-$CF_3$ |
| 34 | 4-OH |
| 35 | 4-CN |
| 36 | 4-$NH_2$ |
| 37 | 4-$NHCOCH_3$ |
| 38 | 4-COOH |
| 39 | 4-Ph |
| 40 | 4-(4-Py) |

TABLE 2

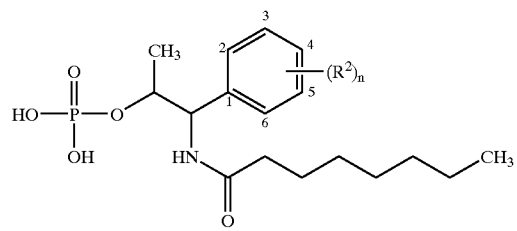

(I-B)

| No. | $(R^2)_n$ |
|---|---|
| 1 | H |
| 2 | 2-Me |
| 3 | 3-Me |
| 4 | 4-Me |

TABLE 2-continued

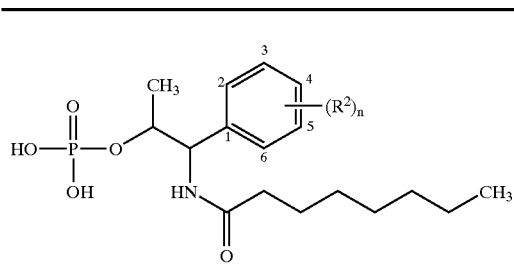

(I-B)

| No. | $(R^2)_n$ |
|---|---|
| 5 | 3,4-di-Me |
| 6 | 3,5-di-Me |
| 7 | 2,4,6-tri-Me |
| 8 | 2-OMe |
| 9 | 3-OMe |
| 10 | 4-OMe |
| 11 | 3,4-di-OMe |
| 12 | 3,5-di-OMe |
| 13 | 2,4,6-tri-OMe |
| 14 | 3-Me,5-OMe |
| 15 | 3,4-di-Me,5-OMe |
| 16 | 2-$NO_2$ |
| 17 | 3-$NO_2$ |
| 18 | 4-$NO_2$ |
| 19 | 2-F |
| 20 | 3-F |
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |
| 30 | 3-OMe,5-F |
| 31 | 3-$CF_3$ |
| 32 | 4-$CF_3$ |
| 33 | 3-Me,5-$CF_3$ |
| 34 | 4-OH |
| 35 | 4-CN |
| 36 | 4-$NH_2$ |
| 37 | 4-NHCOCH$_3$ |
| 38 | 4-COOH |
| 39 | 4-Ph |
| 40 | 4-(4-Py) |

TABLE 3

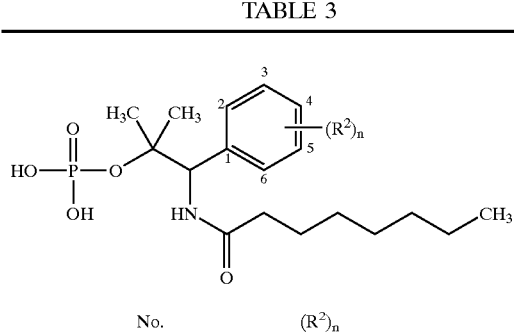

(I-C)

| No. | $(R^2)_n$ |
|---|---|
| 1 | H |
| 2 | 2-Me |
| 3 | 3-Me |
| 4 | 4-Me |
| 5 | 3,4-di-Me |
| 6 | 3,5-di-Me |
| 7 | 2,4,6-tri-Me |
| 8 | 2-OMe |

TABLE 3-continued

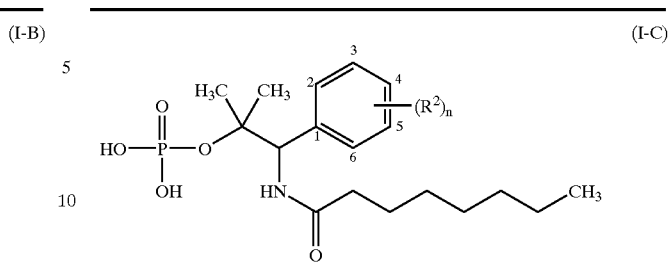

(I-C)

| No. | $(R^2)_n$ |
|---|---|
| 9 | 3-OMe |
| 10 | 4-OMe |
| 11 | 3,4-di-OMe |
| 12 | 3,5-di-OMe |
| 13 | 2,4,6-tri-OMe |
| 14 | 3-Me,5-OMe |
| 15 | 3,4-di-Me,5-OMe |
| 16 | 2-$NO_2$ |
| 17 | 3-$NO_2$ |
| 18 | 4-$NO_2$ |
| 19 | 2-F |
| 20 | 3-F |
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |
| 30 | 3-OMe,5-F |
| 31 | 3-$CF_3$ |
| 32 | 4-$CF_3$ |
| 33 | 3-Me,5-$CF_3$ |
| 34 | 4-OH |
| 35 | 4-CN |
| 36 | 4-$NH_2$ |
| 37 | 4-NHCOCH$_3$ |
| 38 | 4-COOH |
| 39 | 4-Ph |
| 40 | 4-(4-Py) |

TABLE 4

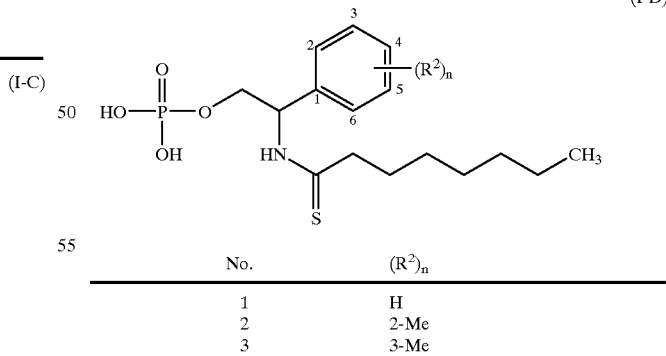

(I-D)

| No. | $(R^2)_n$ |
|---|---|
| 1 | H |
| 2 | 2-Me |
| 3 | 3-Me |
| 4 | 4-Me |
| 5 | 3,4-di-Me |
| 6 | 3,5-di-Me |
| 7 | 2,4,6-tri-Me |
| 8 | 2-OMe |
| 9 | 3-OMe |
| 10 | 4-OMe |
| 11 | 3,4-di-OMe |
| 12 | 3,5-di-OMe |

TABLE 4-continued (I-D)

| No. | $(R^2)_n$ |
|---|---|
| 13 | 2,4,6-tri-OMe |
| 14 | 3-Me,5-OMe |
| 15 | 3,4-di-Me,5-OMe |
| 16 | 2-NO$_2$ |
| 17 | 3-NO$_2$ |
| 18 | 4-NO$_2$ |
| 19 | 2-F |
| 20 | 3-F |
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |
| 30 | 3-OMe,5-F |
| 31 | 3-CF$_3$ |
| 32 | 4-CF$_3$ |
| 33 | 3-Me,5-CF$_3$ |
| 34 | 4-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 5

(I-E)

| No. | $(R^2)_n$ |
|---|---|
| 1 | H |
| 2 | 2-Me |
| 3 | 3-Me |
| 4 | 4-Me |
| 5 | 3,4-di-Me |
| 6 | 3,5-di-Me |
| 7 | 2,4,6-tri-Me |
| 8 | 2-OMe |
| 9 | 3-OMe |
| 10 | 4-OMe |
| 11 | 3,4-di-OMe |
| 12 | 3,5-di-OMe |
| 13 | 2,4,6-tri-OMe |
| 14 | 3-Me,5-OMe |
| 15 | 3,4-di-Me,5-OMe |
| 16 | 2-NO$_2$ |

TABLE 5-continued (I-E)

| No. | $(R^2)_n$ |
|---|---|
| 17 | 3-NO$_2$ |
| 18 | 4-NO$_2$ |
| 19 | 2-F |
| 20 | 3-F |
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |
| 30 | 3-OMe,5-F |
| 31 | 3-CF$_3$ |
| 32 | 4-CF$_3$ |
| 33 | 3-Me,5-CF$_3$ |
| 34 | 4-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 6

(I-F)

| No. | $(R^2)_n$ |
|---|---|
| 1 | H |
| 2 | 2-Me |
| 3 | 3-Me |
| 4 | 4-Me |
| 5 | 3,4-di-Me |
| 6 | 3,5-di-Me |
| 7 | 2,4,6-tri-Me |
| 8 | 2-OMe |
| 9 | 3-OMe |
| 10 | 4-OMe |
| 11 | 3,4-di-OMe |
| 12 | 3,5-di-OMe |
| 13 | 2,4,6-tri-OMe |
| 14 | 3-Me,5-OMe |
| 15 | 3,4-di-Me,5-OMe |
| 16 | 2-NO$_2$ |
| 17 | 3-NO$_2$ |
| 18 | 4-NO$_2$ |
| 19 | 2-F |
| 20 | 3-F |

TABLE 6-continued

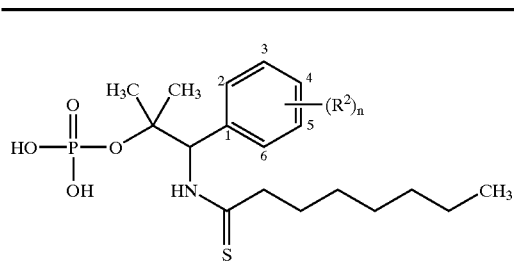

(I-F)

| No. | $(R^2)_n$ |
|---|---|
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |
| 30 | 3-OMe,5-F |
| 31 | 3-CF$_3$ |
| 32 | 4-CF$_3$ |
| 33 | 3-Me,5-CF$_3$ |
| 34 | 4-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 7

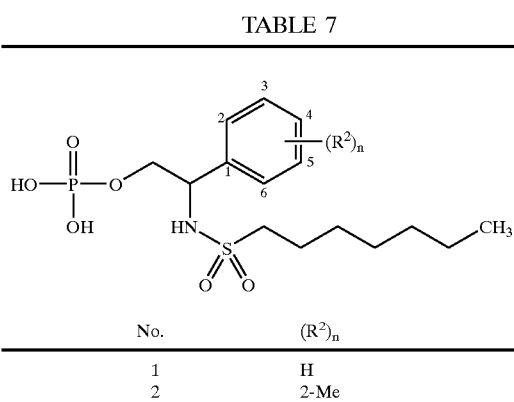

(I-G)

| No. | $(R^2)_n$ |
|---|---|
| 1 | H |
| 2 | 2-Me |
| 3 | 3-Me |
| 4 | 4-Me |
| 5 | 3,4-di-Me |
| 6 | 3,5-di-Me |
| 7 | 2,4,6-tri-Me |
| 8 | 2-OMe |
| 9 | 3-OMe |
| 10 | 4-OMe |
| 11 | 3,4-di-OMe |
| 12 | 3,5-di-OMe |
| 13 | 2,4,6-tri-OMe |
| 14 | 3-Me,5-OMe |
| 15 | 3,4-di-Me,5-OMe |
| 16 | 2-NO$_2$ |
| 17 | 3-NO$_2$ |
| 18 | 4-NO$_2$ |
| 19 | 2-F |
| 20 | 3-F |
| 21 | 4-F |
| 22 | 2,4,6-tri-F |
| 23 | 2-Br |
| 24 | 3-Br |

TABLE 7-continued

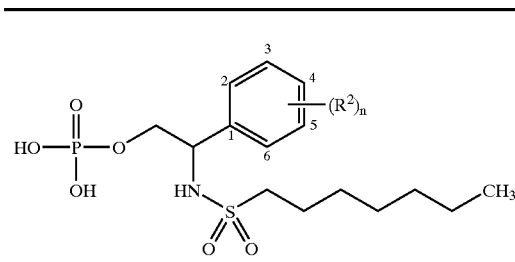

(I-G)

| No. | $(R^2)_n$ |
|---|---|
| 25 | 4-Br |
| 26 | 2-Cl |
| 27 | 3-Cl |
| 28 | 4-Cl |
| 29 | 4-I |
| 30 | 3-OMe,5-F |
| 31 | 3-CF$_3$ |
| 32 | 4-CF$_3$ |
| 33 | 3-Me,5-CF$_3$ |
| 34 | 4-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 8

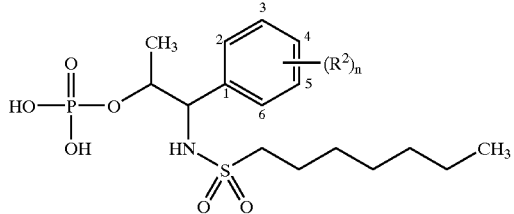

(I-H)

| No. | $(R^2)_n$ |
|---|---|
| 1 | H |
| 2 | 2-Me |
| 3 | 3-Me |
| 4 | 4-Me |
| 5 | 3,4-di-Me |
| 6 | 3,5-di-Me |
| 7 | 2,4,6-tri-Me |
| 8 | 2-OMe |
| 9 | 3-OMe |
| 10 | 4-OMe |
| 11 | 3,4-di-OMe |
| 12 | 3,5-di-OMe |
| 13 | 2,4,6-tri-OMe |
| 14 | 3-Me,5-OMe |
| 15 | 3,4-di-Me,5-OMe |
| 16 | 2-NO$_2$ |
| 17 | 3-NO$_2$ |
| 18 | 4-NO$_2$ |
| 19 | 2-F |
| 20 | 3-F |
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |

TABLE 8-continued

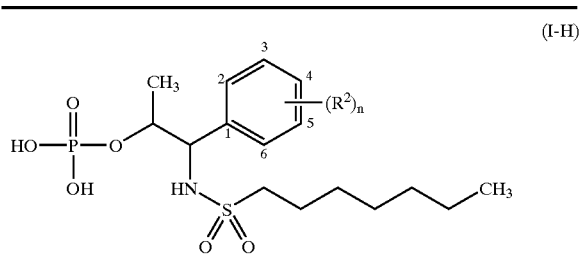

(I-H)

| No. | (R²)ₙ |
|---|---|
| 30 | 3-OMe,5-F |
| 31 | 3-CF₃ |
| 32 | 4-CF₃ |
| 33 | 3-Me,5-CF₃ |
| 34 | 4-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 9

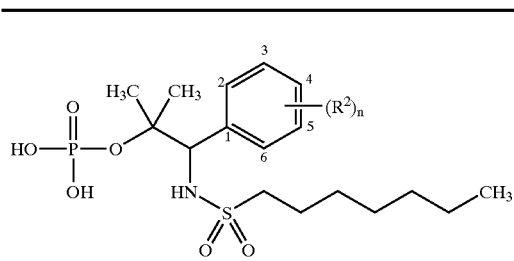

(I-J)

| No. | (R²)ₙ |
|---|---|
| 1 | H |
| 2 | 2-Me |
| 3 | 3-Me |
| 4 | 4-Me |
| 5 | 3,4-di-Me |
| 6 | 3,5-di-Me |
| 7 | 2,4,6-tri-Me |
| 8 | 2-OMe |
| 9 | 3-OMe |
| 10 | 4-OMe |
| 11 | 3,4-di-OMe |
| 12 | 3,5-di-OMe |
| 13 | 2,4,6-tri-OMe |
| 14 | 3-Me,5-OMe |
| 15 | 3,4-di-Me,5-OMe |
| 16 | 2-NO₂ |
| 17 | 3-NO₂ |
| 18 | 4-NO₂ |
| 19 | 2-F |
| 20 | 3-F |
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |
| 30 | 3-OMe,5-F |
| 31 | 3-CF₃ |
| 32 | 4-CF₃ |
| 33 | 3-Me,5-CF₃ |
| 34 | 4-OH |

TABLE 9-continued

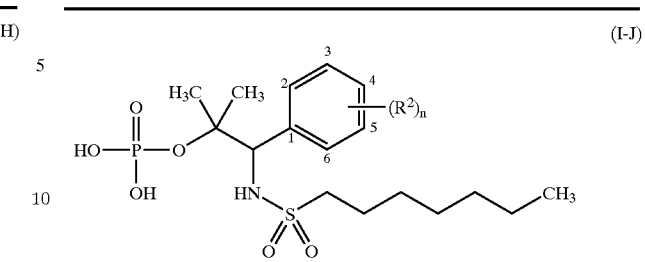

(I-J)

| No. | (R²)ₙ |
|---|---|
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 10

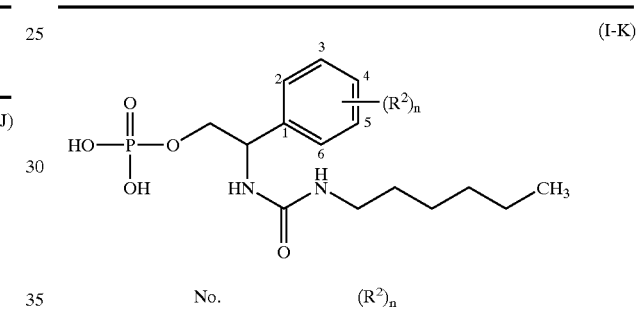

(I-K)

| No. | (R²)ₙ |
|---|---|
| 1 | H |
| 2 | 2-Me |
| 3 | 3-Me |
| 4 | 4-Me |
| 5 | 3,4-di-Me |
| 6 | 3,5-di-Me |
| 7 | 2,4,6-tri-Me |
| 8 | 2-OMe |
| 9 | 3-OMe |
| 10 | 4-OMe |
| 11 | 3,4-di-OMe |
| 12 | 3,5-di-OMe |
| 13 | 2,4,6-tri-OMe |
| 14 | 3-Me,5-OMe |
| 15 | 3,4-di-Me,5-OMe |
| 16 | 2-NO₂ |
| 17 | 3-NO₂ |
| 18 | 4-NO₂ |
| 19 | 2-F |
| 20 | 3-F |
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |
| 30 | 3-OMe,5-F |
| 31 | 3-CF₃ |
| 32 | 4-CF₃ |
| 33 | 3-Me,5-CF₃ |
| 34 | 4-OH |
| 35 | 4-CN |
| 36 | 4-NH₂ |
| 37 | 4-NHCOCH₃ |
| 38 | 4-COOH |

TABLE 10-continued (I-K)

| No. | $(R^2)_n$ |
|---|---|
| 39 | 4-Ph |
| 40 | 4-(4-Py) |

TABLE 11

(I-L)

| No. | $(R^2)_n$ |
|---|---|
| 1 | H |
| 2 | 2-Me |
| 3 | 3-Me |
| 4 | 4-Me |
| 5 | 3,4-di-Me |
| 6 | 3,5-di-Me |
| 7 | 2,4,6-tri-Me |
| 8 | 2-OMe |
| 9 | 3-OMe |
| 10 | 4-OMe |
| 11 | 3,4-di-OMe |
| 12 | 3,5-di-OMe |
| 13 | 2,4,6-tri-OMe |
| 14 | 3-Me,5-OMe |
| 15 | 3,4-di-Me,5-OMe |
| 16 | 2-NO$_2$ |
| 17 | 3-NO$_2$ |
| 18 | 4-NO$_2$ |
| 19 | 2-F |
| 20 | 3-F |
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |
| 30 | 3-OMe,5-F |
| 31 | 3-CF$_3$ |
| 32 | 4-CF$_3$ |
| 33 | 3-Me,5-CF$_3$ |
| 34 | 4-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 12

(I-M)

| No. | $(R^2)_n$ |
|---|---|
| 1 | H |
| 2 | 2-Me |
| 3 | 3-Me |
| 4 | 4-Me |
| 5 | 3,4-di-Me |
| 6 | 3,5-di-Me |
| 7 | 2,4,6-tri-iMe |
| 8 | 2-OMe |
| 9 | 3-OMe |
| 10 | 4-OMe |
| 11 | 3,4-di-OMe |
| 12 | 3,5-di-OMe |
| 13 | 2,4,6-tri-OMe |
| 14 | 3-Me,5-OMe |
| 15 | 3,4-di-Me,5-OMe |
| 16 | 2-NO$_2$ |
| 17 | 3-NO$_2$ |
| 18 | 4-NO$_2$ |
| 19 | 2-F |
| 20 | 3-F |
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |
| 30 | 3-OMe,5-F |
| 31 | 3-CF$_3$ |
| 32 | 4-CF$_3$ |
| 33 | 3-Me,5-CF$_3$ |
| 34 | 4-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 13

(I-N)

| No. | $(R^2)_n$ |
|---|---|
| 1 | H |
| 2 | 2-Me |
| 3 | 3-Me |
| 4 | 4-Me |

TABLE 13-continued

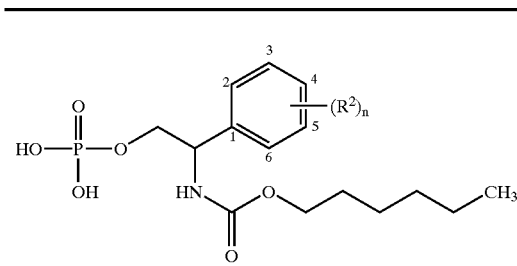

(I-N)

| No. | (R²)ₙ |
|---|---|
| 5 | 3,4-di-Me |
| 6 | 3,5-di-Me |
| 7 | 2,4,6-tri-Me |
| 8 | 2-OMe |
| 9 | 3-OMe |
| 10 | 4-OMe |
| 11 | 3,4-di-OMe |
| 12 | 3,5-di-OMe |
| 13 | 2,4,6-tri-OMe |
| 14 | 3-Me,5-OMe |
| 15 | 3,4-di-Me,5-OMe |
| 16 | 2-NO₂ |
| 17 | 3-NO₂ |
| 18 | 4-NO₂ |
| 19 | 2-F |
| 20 | 3-F |
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |
| 30 | 3-OMe,5-F |
| 31 | 3-CF₃ |
| 32 | 4-CF₃ |
| 33 | 3-Me,5-CF₃ |
| 34 | 4-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 14

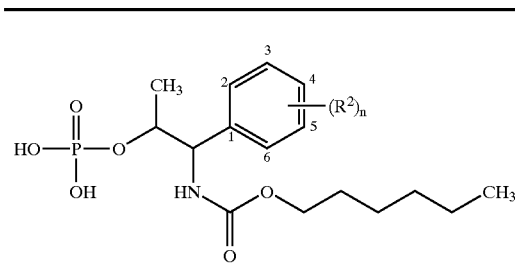

(I-O)

| No. | (R²)ₙ |
|---|---|
| 1 | H |
| 2 | 2-Me |
| 3 | 3-Me |
| 4 | 4-Me |
| 5 | 3,4-di-Me |
| 6 | 3,5-di-Me |
| 7 | 2,4,6-tri-Me |
| 8 | 2-OMe |

TABLE 14-continued (I-O)

| No. | (R²)ₙ |
|---|---|
| 9 | 3-OMe |
| 10 | 4-OMe |
| 11 | 3,4-di-OMe |
| 12 | 3,5-di-OMe |
| 13 | 2,4,6-tri-OMe |
| 14 | 3-Me,5-OMe |
| 15 | 3,4-di-Me,5-OMe |
| 16 | 2-NO₂ |
| 17 | 3-NO₂ |
| 18 | 4-NO₂ |
| 19 | 2-F |
| 20 | 3-F |
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |
| 30 | 3-OMe,5-F |
| 31 | 3-CF₃ |
| 32 | 4-CF₃ |
| 33 | 3-Me,5-CF₃ |
| 34 | 4-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 15

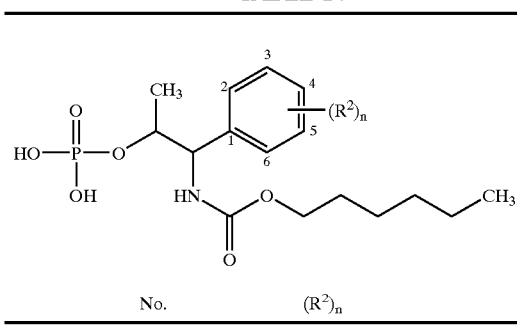

(I-P)

| No. | (R²)ₙ |
|---|---|
| 1 | H |
| 2 | 2-Me |
| 3 | 3-Me |
| 4 | 4-Me |
| 5 | 3,4-di-Me |
| 6 | 3,5-di-Me |
| 7 | 2,4,6-tri-Me |
| 8 | 2-OMe |
| 9 | 3-OMe |
| 10 | 4-OMe |
| 11 | 3,4-di-OMe |
| 12 | 3,5-di-OMe |

TABLE 15-continued (I-P)

[Structure: phosphate-O-C(CH3)2-CH(NHC(O)O-hexyl)-phenyl(R²)n]

| No. | (R²)n |
|---|---|
| 13 | 2,4,6-tri-OMe |
| 14 | 3-Me,5-OMe |
| 15 | 3,4-di-Me,5-OMe |
| 16 | 2-NO₂ |
| 17 | 3-NO₂ |
| 18 | 4-NO₂ |
| 19 | 2-F |
| 20 | 3-F |
| 21 | 4-F |
| 22 | 2,4,6-tri-F |
| 23 | 2-Br |
| 24 | 3-Br |
| 25 | 4-Br |
| 26 | 2-Cl |
| 27 | 3-Cl |
| 28 | 4-Cl |
| 29 | 4-I |
| 30 | 3-OMe,5-F |
| 31 | 3-CF₃ |
| 32 | 4-CF₃ |
| 33 | 3-Me,5-CF₃ |
| 34 | 4-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 16

(I-A1)

[Structure: phosphate-O-CH2-CH(NHC(O)-heptyl)-naphthyl(R²)n]

| No. | (R²)n |
|---|---|
| 1 | H |
| 2 | 2-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-di-Me |

TABLE 16-continued (I-A1)

[Structure: phosphate-O-CH2-CH(NHC(O)-heptyl)-naphthyl(R²)n]

| No. | (R²)n |
|---|---|
| 16 | 3-NO₂ |
| 17 | 4-NO₂ |
| 18 | 6-NO₂ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF₃ |
| 27 | 4-CF₃ |
| 28 | 6-CF₃ |
| 29 | 3-Me,6-CF₃ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 17

(I-B1)

[Structure: phosphate-O-CH(CH3)-CH(NHC(O)-heptyl)-naphthyl(R²)n]

| No. | (R²)n |
|---|---|
| 1 | H |
| 2 | 2-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-diMe |
| 16 | 3-NO₂ |
| 17 | 4-NO₂ |

TABLE 17-continued (I-B1)

| No. | (R²)ₙ |
|---|---|
| 18 | 6-NO₂ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF₃ |
| 27 | 4-CF₃ |
| 28 | 6-CF₃ |
| 29 | 3-Me,6-CF₃ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 18

(I-C1)

| No. | (R²)ₙ |
|---|---|
| 1 | H |
| 2 | 2-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-di-Me |
| 16 | 3-NO₂ |
| 17 | 4-NO₂ |
| 18 | 6-NO₂ |
| 19 | 3-F |

TABLE 18-continued (I-C1)

| No. | (R²)ₙ |
|---|---|
| 20 | 4-F |
| 21 | 3-Cl |
| 22 | 4-Cl |
| 23 | 3-Br |
| 24 | 4-Br |
| 25 | 4-I |
| 26 | 3-CF₃ |
| 27 | 4-CF₃ |
| 28 | 6-CF₃ |
| 29 | 3-Me,6-CF₃ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 19

(I-D1)

| No. | (R²)ₙ |
|---|---|
| 1 | H |
| 2 | 2-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-di-Me |
| 16 | 3-NO₂ |
| 17 | 4-NO₂ |
| 18 | 6-NO₂ |
| 19 | 3-F |
| 20 | 4-F |
| 21 | 3-Cl |

TABLE 19-continued (I-D1)

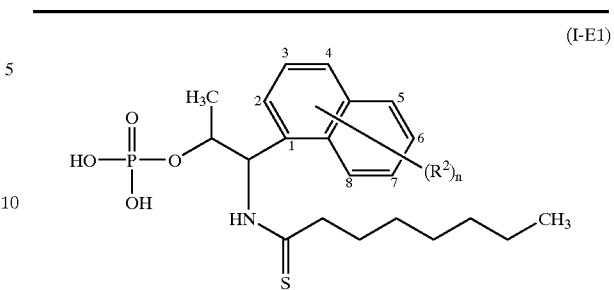

| No. | $(R^2)_n$ |
|---|---|
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me,6-CF$_3$ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 20

(I-E1)

| No. | $(R^2)_n$ |
|---|---|
| 1 | H |
| 2 | 2-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-diMe |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |

TABLE 20-continued (I-E1)

| No. | $(R^2)_n$ |
|---|---|
| 24 | 4-Br |
| 25 | 4-I |
| 26 | 3-CF$_3$ |
| 27 | 4-CF$_3$ |
| 28 | 6-CF$_3$ |
| 29 | 3-Me,6-CF$_3$ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 21

(I-F1)

| No. | $(R^2)_n$ |
|---|---|
| 1 | H |
| 2 | 2-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-diMe |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |

TABLE 21-continued (I-F1)

[Structure: naphthalene with positions labeled 1-8 bearing (R²)ₙ, connected to CH(C(CH₃)₂-O-P(=O)(OH)₂)-NH-C(=S)-C₇H₁₅]

| No. | (R²)ₙ |
|---|---|
| 26 | 3-CF₃ |
| 27 | 4-CF₃ |
| 28 | 6-CF₃ |
| 29 | 3-Me,6-CF₃ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 22

(I-G1)

[Structure: naphthalene with positions labeled 1-8 bearing (R²)ₙ, connected to CH(CH₂-O-P(=O)(OH)₂)-NH-SO₂-C₇H₁₅]

| No. | (R²)ₙ |
|---|---|
| 1 | H |
| 2 | 2-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-di-Me |
| 16 | 3-NO₂ |
| 17 | 4-NO₂ |
| 18 | 6-NO₂ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF₃ |
| 27 | 4-CF₃ |
| 28 | 6-CF₃ |

TABLE 22-continued (I-G1)

[Structure: same as Table 22]

| No. | (R²)ₙ |
|---|---|
| 29 | 3-Me,6-CF₃ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 23

(I-H1)

[Structure: naphthalene with positions labeled 1-8 bearing (R²)ₙ, connected to CH(CH(CH₃)-O-P(=O)(OH)₂)-NH-SO₂-C₇H₁₅]

| No. | (R²)ₙ |
|---|---|
| 1 | H |
| 2 | 2-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-di-Me |
| 16 | 3-NO₂ |
| 17 | 4-NO₂ |
| 18 | 6-NO₂ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF₃ |
| 27 | 4-CF₃ |
| 28 | 6-CF₃ |
| 29 | 3-Me,6-CF₃ |
| 30 | 4-OH |
| 31 | 5-OH |
| 32 | 6-OH |

TABLE 23-continued (I-H1)

| No. | $(R^2)_n$ |
|-----|-----------|
| 33 | 8-OH |
| 34 | 3,4-di-Me,6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 24

((I-J1))

| No. | $(R^2)_n$ |
|-----|-----------|
| 1 | H |
| 2 | 2-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-di-Me |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me,6-CF$_3$ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH$_2$ |

TABLE 24-continued ((I-J1))

| No. | $(R^2)_n$ |
|-----|-----------|
| 37 | 4-NHCOCH$_3$ |
| 38 | 4-COOH |
| 39 | 4-Ph |
| 40 | 4-(4-Py) |

TABLE 25

(I-K1)

| No. | $(R^2)_n$ |
|-----|-----------|
| 1 | H |
| 2 | 2-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-di-Me |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me,6-CF$_3$ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH$_2$ |
| 37 | 4-NHCOCH$_3$ |
| 38 | 4-COOH |
| 39 | 4-Ph |

TABLE 25-continued (I-K1)

| No. | $(R^2)_n$ |
|---|---|
| 40 | 4-(4-Py) |

TABLE 26

(I-L1)

| No. | $(R^2)_n$ |
|---|---|
| 1 | H |
| 2 | 2-Me |
| 3 | 3-Me |
| 4 | 4-Me |
| 5 | 5-Me |
| 6 | 6-Me |
| 7 | 7-Me |
| 8 | 8-Me |
| 9 | 4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-diMe |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me,6-CF$_3$ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 27

(I-M1)

| No. | $(R^2)_n$ |
|---|---|
| 1 | H |
| 2 | 2-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-di-Me |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me,6-CF$_3$ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 28

(I-N1)

| No. | $(R^2)_n$ |
|---|---|
| 1 | H |
| 2 | 2-Me |

TABLE 28-continued (I-N1)

[Structure: naphthyl group with (R²)ₙ substituents, CH(NHC(O)O-hexyl)-CH₂-O-P(O)(OH)₂]

| No. | (R²)ₙ |
|---|---|
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-diMe |
| 16 | 3-NO₂ |
| 17 | 4-NO₂ |
| 18 | 6-NO₂ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF₃ |
| 27 | 4-CF₃ |
| 28 | 6-CF₃ |
| 29 | 3-Me,6-CF₃ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 29

(I-O1)

[Structure: naphthyl group with (R²)ₙ substituents, CH(NHC(O)O-hexyl)-CH(CH₃)-O-P(O)(OH)₂]

| No. | (R²)ₙ |
|---|---|
| 1 | H |
| 2 | 2-Me |
| 3 | 3-Me |
| 4 | 4-Me |

TABLE 29-continued (I-O1)

| No. | (R²)ₙ |
|---|---|
| 5 | 5-Me |
| 6 | 6-Me |
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-di-Me |
| 16 | 3-NO₂ |
| 17 | 4-NO₂ |
| 18 | 6-NO₂ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF₃ |
| 27 | 4-CF₃ |
| 28 | 6-CF₃ |
| 29 | 3-Me,6-CF₃ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 30

(I-P1)

[Structure: naphthyl group with (R²)ₙ substituents, CH(NHC(O)O-hexyl)-C(CH₃)₂-O-P(O)(OH)₂]

| No. | (R²)ₙ |
|---|---|
| 1 | H |
| 2 | 2-Me |
| 3 | 3-Me |
| 4 | 4-Me |
| 5 | 5-Me |
| 6 | 6-Me |

TABLE 30-continued (I-P1)

[Structure: phosphate-O-C(CH₃)₂-CH(NHC(O)O-hexyl)-naphthyl with (R²)ₙ]

| No. | (R²)ₙ |
|---|---|
| 7 | 7-Me |
| 8 | 8-Me |
| 9 | 3,4-di-Me |
| 10 | 4,6-di-Me |
| 11 | 2,3,4-tri-Me |
| 12 | 3,5,7-tri-Me |
| 13 | 2-OMe |
| 14 | 4-OMe |
| 15 | 2-OMe,5,6-diMe |
| 16 | 3-NO₂ |
| 17 | 4-NO₂ |
| 18 | 6-NO₂ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF₃ |
| 27 | 4-CF₃ |
| 28 | 6-CF₃ |
| 29 | 3-Me,6-CF₃ |
| 30 | 4-OH |
| 31 | 5-OH |
| 32 | 6-OH |
| 33 | 8-OH |
| 34 | 3,4-di-Me,6-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 31

(I-A2)

| No. | (R²)ₙ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |

TABLE 31-continued (I-A2)

| No. | (R²)ₙ |
|---|---|
| 10 | 4,6-di-Me |
| 11 | 1,3,4-tri-Me |
| 12 | 3,5,7-tri-Me |
| 13 | 1-OMe |
| 14 | 5-OMe |
| 15 | 1-OMe, 5,6-di-Me |
| 16 | 3-NO₂ |
| 17 | 4-NO₂ |
| 18 | 6-NO₂ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF₃ |
| 27 | 4-CF₃ |
| 28 | 6-CF₃ |
| 29 | 3-Me, 6-CF₃ |
| 30 | 4-OH |
| 31 | 5-OH |
| 32 | 6-OH |
| 33 | 8-OH |
| 34 | 3,4-di-Me, 6-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 32

(I-B2)

| No. | (R²)ₙ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 1,3,4-tri-Me |
| 12 | 3,5,7-tri-Me |
| 13 | 1-OMe |

TABLE 32-continued (I-B2)

| No. | (R²)ₙ |
|---|---|
| 14 | 5-OMe |
| 15 | 1-OMe-5,6-di-Me |
| 16 | 3-NO₂ |
| 17 | 4-NO₂ |
| 18 | 6-NO₂ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF₃ |
| 27 | 4-CF₃ |
| 28 | 6-CF₃ |
| 29 | 3-Me, 6-CF₃ |
| 30 | 4-OH |
| 31 | 5-OH |
| 32 | 6-OH |
| 33 | 8-OH |
| 34 | 3,4-di-Me, 6-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 33

(I-C2)

| No. | (R²)ₙ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 1,3,4-tri-Me |
| 12 | 3,5,7-tri-Me |
| 13 | 1-OMe |
| 14 | 5-OMe |
| 15 | 1-OMe, 5,6-di-Me |
| 16 | 3-NO₂ |
| 17 | 4-NO₂ |

TABLE 33-continued (I-C2)

| No. | (R²)ₙ |
|---|---|
| 18 | 6-NO₂ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF₃ |
| 27 | 4-CF₃ |
| 28 | 6-CF₃ |
| 29 | 3-Me, 6-CF₃ |
| 30 | 4-OH |
| 31 | 5-OH |
| 32 | 6-OH |
| 33 | 8-OH |
| 34 | 3,4-di-Me, 6-OH |
| 35 | 4-CN |
| 36 | 4-NH₂ |
| 37 | 4-NHCOCH₃ |
| 38 | 4-COOH |
| 39 | 4-Ph |
| 40 | 4-(4-Py) |

TABLE 34

(I-D2)

| No. | (R²)ₙ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 1,3,4-tri-Me |
| 12 | 3,5,7-tri-Me |
| 13 | 1-OMe |
| 14 | 5-OMe |
| 15 | 1-OMe, 5,6-di-Me |
| 16 | 3-NO₂ |
| 17 | 4-NO₂ |
| 18 | 6-NO₂ |
| 19 | 3-F |
| 20 | 4-F |
| 21 | 3-Cl |

TABLE 34-continued (I-D2)

Structure: Naphthalene with positions 1-8 labeled, substituted at position 2 with CH(NHC(=S)C₇H₁₅)CH₂OP(=O)(OH)₂, and $(R^2)_n$ on the other ring.

| No. | $(R^2)_n$ |
|---|---|
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me, 6-CF$_3$ |
| 30 | 4-OH |
| 31 | 5-OH |
| 32 | 6-OH |
| 33 | 8-OH |
| 34 | 3,4-di-Me, 6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 35

(I-E2)

Structure: Naphthalene substituted at position 2 with CH(NHC(=S)C₇H₁₅)CH(CH₃)OP(=O)(OH)₂, and $(R^2)_n$.

| No. | $(R^2)_n$ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 1,3,4-tri-Me |
| 12 | 3,5,7-tri-Me |
| 13 | 1-OMe |
| 14 | 5-OMe |
| 15 | 1-OMe, 5,6-di-Me |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |

TABLE 35-continued (I-E2)

| No. | $(R^2)_n$ |
|---|---|
| 26 | 3-CF$_3$ |
| 27 | 4-CF$_3$ |
| 28 | 6-CF$_3$ |
| 29 | 3-Me, 6-CF$_3$ |
| 30 | 4-OH |
| 31 | 5-OH |
| 32 | 6-OH |
| 33 | 8-OH |
| 34 | 3,4-di-Me, 6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 36

(I-F2)

Structure: Naphthalene substituted at position 2 with CH(NHC(=S)C₇H₁₅)C(CH₃)₂OP(=O)(OH)₂, and $(R^2)_n$.

| No. | $(R^2)_n$ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 1,3,4-tri-Me |
| 12 | 3,5,7-tri-Me |
| 13 | 1-OMe |
| 14 | 5-OMe |
| 15 | 1-OMe, 5,6-di-Me |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me, 6-CF$_3$ |

TABLE 36-continued

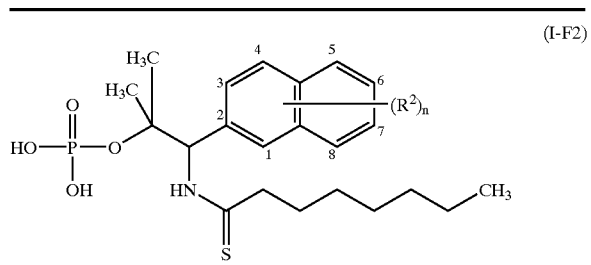

(I-F2)

| No. | $(R^2)_n$ |
|---|---|
| 30 | 4-OH |
| 31 | 5-OH |
| 32 | 6-OH |
| 33 | 8-OH |
| 34 | 3,4-di-Me, 6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 37

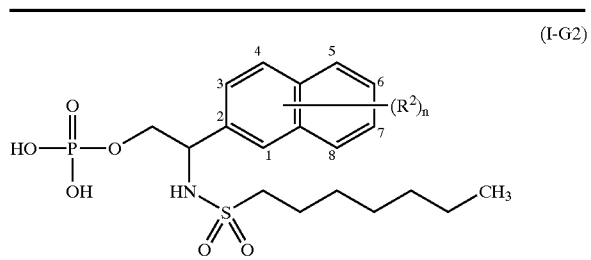

(I-G2)

| No. | $(R^2)_n$ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 1,3,4-tri-Me |
| 12 | 3,5,7-tri-Me |
| 13 | 1-OMe |
| 14 | 5-OMe |
| 15 | 1-OMe, 5,6-di-Me |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me, 6-CF$_3$ |
| 30 | 4-OH |
| 31 | 5-OH |
| 32 | 6-OH |
| 33 | 8-OH |

TABLE 37-continued

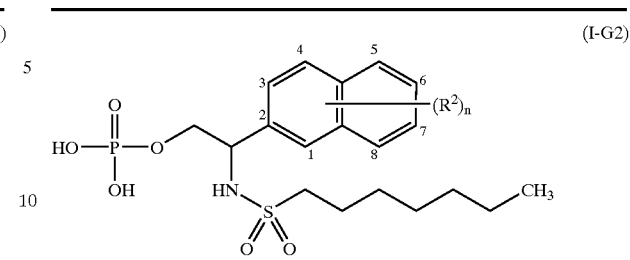

(I-G2)

| No. | $(R^2)_n$ |
|---|---|
| 34 | 3,4-di-Me, 6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 38

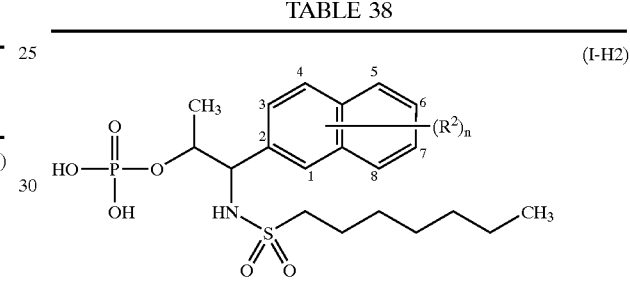

(I-H2)

| No. | $(R^2)_n$ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 1,3,4-tri-Me |
| 12 | 3,5,7-tri-Me |
| 13 | 1-OMe |
| 14 | 5-OMe |
| 15 | 1-OMe-5,6-di-Me |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me, 6-CF$_3$ |
| 30 | 4-OH |
| 31 | 5-OH |
| 32 | 6-OH |
| 33 | 8-OH |
| 34 | 3,4-di-Me, 6-OH |
| 35 | 4-CN |
| 36 | 4-NH$_2$ |
| 37 | 4-NHCOCH$_3$ |
| 38 | 4-COOH |

TABLE 38-continued (I-H2)

| No. | $(R^2)_n$ |
|---|---|
| 39 | 4-Ph |
| 40 | 4-(4-Py,) |

TABLE 39

(I-J2)

| No. | $(R^2)_n$ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 1,3,4-tri-Me |
| 12 | 3,5,7-tri-Me |
| 13 | 1-OMe |
| 14 | 5-OMe |
| 15 | 1-OMe-5,6-di-Me |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me, 6-CF$_3$ |
| 30 | 4-OH |
| 31 | 5-OH |
| 32 | 6-OH |
| 33 | 8-OH |
| 34 | 3,4-di-Me, 6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 40

(I-K2)

| No. | $(R^2)_n$ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 1,3,4-tri-Me |
| 12 | 3,5,7-tri-Me |
| 13 | 1-OMe |
| 14 | 5-OMe |
| 15 | 1-OMe, 5,6-di-Me |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me, 6-CF$_3$ |
| 30 | 4-OH |
| 31 | 5-OH |
| 32 | 6-OH |
| 33 | 8-OH |
| 34 | 3,4-di-Me, 6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 41

(I-L2)

| No. | $(R^2)_n$ |
|---|---|
| 1 | H |
| 2 | 1-Me |
| 3 | 3-Me |
| 4 | 4-Me |

TABLE 41-continued

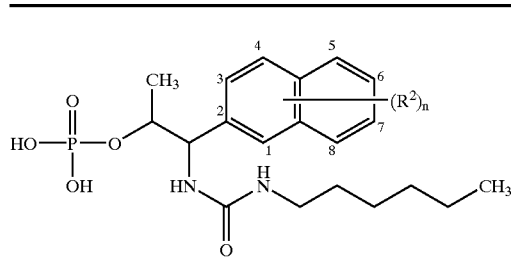

(I-L2)

| No. | $(R^2)_n$ |
|---|---|
| 5 | 5-Me |
| 6 | 6-Me |
| 7 | 7-Me |
| 8 | 8-Me |
| 9 | 3,4-di-Me |
| 10 | 4,6-di-Me |
| 11 | 1,3,4-tri-Me |
| 12 | 3,5,7-tri-Me |
| 13 | 1-OMe |
| 14 | 5-OMe |
| 15 | 1-OMe, 5,6-di-Me |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me, 6-CF$_3$ |
| 30 | 4-OH |
| 31 | 5-OH |
| 32 | 6-OH |
| 33 | 8-OH |
| 34 | 3,4-di-Me, 6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 42

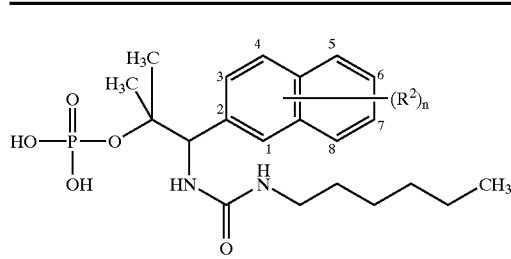

(I-M2)

| No. | $(R^2)_n$ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |

TABLE 42-continued

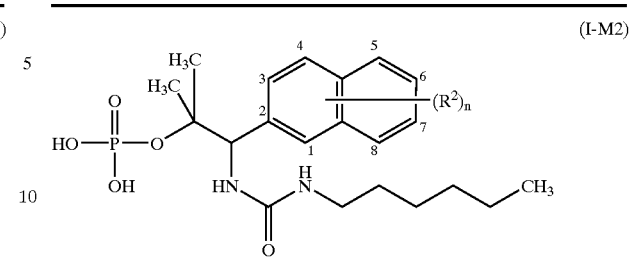

(I-M2)

| No. | $(R^2)_n$ |
|---|---|
| 9 | 3,4-di-Me |
| 10 | 4,6-di-Me |
| 11 | 1,3,4-tri-Me |
| 12 | 3,5,7-tri-Me |
| 13 | 1-OMe |
| 14 | 5-OMe |
| 15 | 1-OMe, 5,6-di-Me |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me, 6-CF$_3$ |
| 30 | 4-OH |
| 31 | 5-OH |
| 32 | 6-OH |
| 33 | 8-OH |
| 34 | 3,4-di-Me, 6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 43

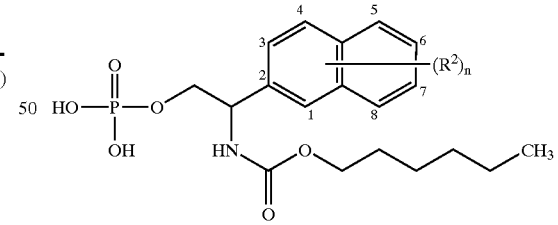

(I-N2)

| No. | $(R^2)_n$ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 1,3,4-tri-Me |
| 12 | 3,5,7-tri-Me |

TABLE 43-continued

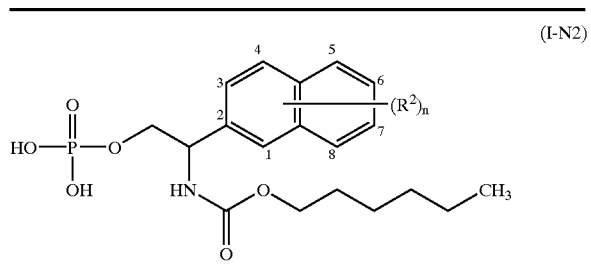
(I-N2)

| No. | $(R^2)_n$ |
|---|---|
| 13 | 1-OMe |
| 14 | 5-OMe |
| 15 | 1-OMe, 5,6-di-Me |
| 16 | 3-NO$_2$ |
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me, 6-CF$_3$ |
| 30 | 4-OH |
| 31 | 5-OH |
| 32 | 6-OH |
| 33 | 8-OH |
| 34 | 3,4-di-Me, 6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 44

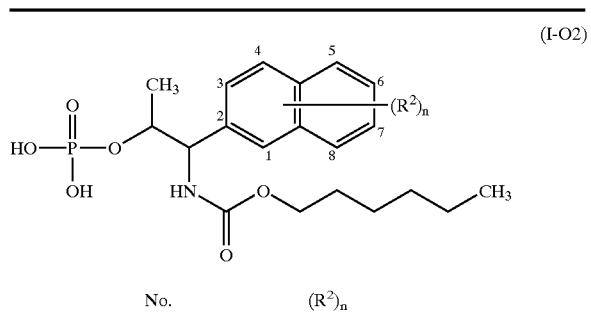
(I-O2)

| No. | $(R^2)_n$ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 1,3,4-tri-Me |
| 12 | 3,5,7-tri-Me |
| 13 | 1-OMe |
| 14 | 5-OMe |
| 15 | 1-OMe, 5,6-di-Me |
| 16 | 3-NO$_2$ |

TABLE 44-continued

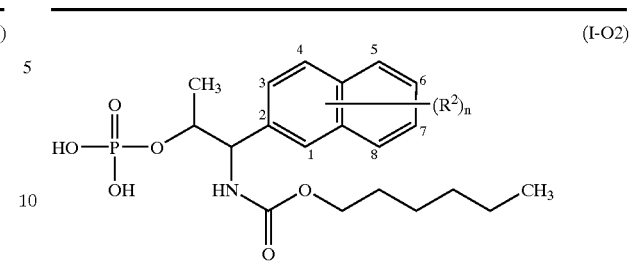
(I-O2)

| No. | $(R^2)_n$ |
|---|---|
| 17 | 4-NO$_2$ |
| 18 | 6-NO$_2$ |
| 19 | 3-F |
| 20 | 4-F |
| 21 | 3-Cl |
| 22 | 4-Cl |
| 23 | 3-Br |
| 24 | 4-Br |
| 25 | 4-I |
| 26 | 3-CF$_3$ |
| 27 | 4-CF$_3$ |
| 28 | 6-CF$_3$ |
| 29 | 3-Me, 6-CF$_3$ |
| 30 | 4-OH |
| 31 | 5-OH |
| 32 | 6-OH |
| 33 | 8-OH |
| 34 | 3,4-di-Me, 6-OH |
| 35 | 4-CN |
| 36 | 4-NH$_2$ |
| 37 | 4-NHCOCH$_3$ |
| 38 | 4-COOH |
| 39 | 4-Ph |
| 40 | 4-(4-Py) |

TABLE 45

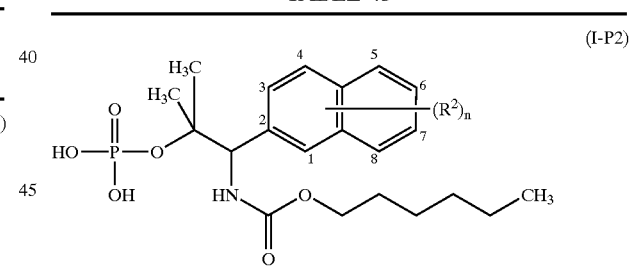
(I-P2)

| No. | $(R^2)_n$ |
|---|---|
| 1 | H |
| 2 | 1-Me |
| 3 | 3-Me |
| 4 | 4-Me |
| 5 | 5-Me |
| 6 | 6-Me |
| 7 | 7-Me |
| 8 | 8-Me |
| 9 | 3,4-di-Me |
| 10 | 4,6-di-Me |
| 11 | 1,3,4-tri-Me |
| 12 | 3,5,7-tri-Me |
| 13 | 1-OMe |
| 14 | 5-OMe |
| 15 | 1-OMe, 5,6-di-Me |
| 16 | 3-NO$_2$ |
| 17 | 4-NO$_2$ |
| 18 | 6-NO$_2$ |
| 19 | 3-F |
| 20 | 4-F |

TABLE 45-continued (I-P2)

| No. | $(R^2)_n$ |
|---|---|
| 21 | 3-Cl |
| 22 | 4-Cl |
| 23 | 3-Br |
| 24 | 4-Br |
| 25 | 4-I |
| 26 | 3-$CF_3$ |
| 27 | 4-$CF_3$ |
| 28 | 6-$CF_3$ |
| 29 | 3-Me, 6-$CF_3$ |
| 30 | 4-OH |
| 31 | 5-OH |
| 32 | 6-OH |
| 33 | 8-OH |
| 34 | 3,4-diMe, 6-OH |
| 35 | 4-CN |
| 36 | 4-$NH_2$ |
| 37 | 4-$NHCOCH_3$ |
| 38 | 4-COOH |
| 39 | 4-Ph |
| 40 | 4-(4-Py) |

TABLE 46

(I-A3)

| No. | T | $(R^2)_n$ |
|---|---|---|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-$NO_2$ |
| 8 | O | 3-Me, 5-$NO_2$ |
| 9 | O | 4-Me, 5-$NO_2$ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-$NO_2$ |
| 19 | S | 3-Me, 5-$NO_2$ |
| 20 | S | 4-Me, 5-$NO_2$ |
| 21 | S | 5-CN |
| 22 | S | 5-COOH |

TABLE 47

(I-B3)

| No. | T | $(R^2)_n$ |
|---|---|---|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-$NO_2$ |
| 8 | O | 3-Me, 5-$NO_2$ |
| 9 | O | 4-Me, 5-$NO_2$ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-$NO_2$ |
| 19 | S | 3-Me, 5-$NO_2$ |
| 20 | S | 4-Me, 5-$NO_2$ |
| 21 | S | 5-CN |
| 22 | S | 5-COOH |

TABLE 48

(I-C3)

| No. | T | $(R^2)_n$ |
|---|---|---|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-$NO_2$ |
| 8 | O | 3-Me, 5-$NO_2$ |
| 9 | O | 4-Me, 5-$NO_2$ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-$NO_2$ |
| 19 | S | 3-Me, 5-$NO_2$ |
| 20 | S | 4-Me, 5-$NO_2$ |
| 21 | S | 5-CN |
| 22 | S | 5-COOH |

TABLE 49

(I-D3)

| No. | T | (R²)ₙ |
|-----|---|-------|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-NO$_2$ |
| 8 | O | 3-Me, 5-NO$_2$ |
| 9 | O | 4-Me, 5-NO$_2$ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-NO$_2$ |
| 19 | S | 3-Me, 5-NO$_2$ |
| 20 | S | 4-Me, 5-NO$_2$ |
| 21 | S | 5-CN |
| 22 | S | 5-COOH |

TABLE 50

(I-E3)

| No. | T | (R²)ₙ |
|-----|---|-------|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-NO$_2$ |
| 8 | O | 3-Me, 5-NO$_2$ |
| 9 | O | 4-Me, 5-NO$_2$ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-NO$_2$ |
| 19 | S | 3-Me, 5-NO$_2$ |
| 20 | S | 4-Me, 5-NO$_2$ |
| 21 | S | 5-CN |
| 22 | S | 5-COOH |

TABLE 51

(I-F3)

| No. | T | (R²)ₙ |
|-----|---|-------|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-NO$_2$ |
| 8 | O | 3-Me, 5-NO$_2$ |
| 9 | O | 4-Me, 5-NO$_2$ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-NO$_2$ |
| 19 | S | 3-Me, 5-NO$_2$ |
| 20 | S | 4-Me, 5-NO$_2$ |
| 21 | S | 5-CN |
| 22 | S | 5-COOH |

TABLE 52

(I-G3)

| No. | T | (R²)ₙ |
|-----|---|-------|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-NO$_2$ |
| 8 | O | 3-Me, 5-NO$_2$ |
| 9 | O | 4-Me, 5-NO$_2$ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-NO$_2$ |
| 19 | S | 3-Me, 5-NO$_2$ |
| 20 | S | 4-Me, 5-NO$_2$ |
| 21 | S | 5-CN |
| 22 | S | 5-COOH |

TABLE 53

(I-H3)

[Structure: phosphate-O-CH(CH3)-CH(NH-SO2-heptyl)-thiophene(T)-(R²)n]

| No. | T | (R²)n |
|-----|---|-------|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-NO₂ |
| 8 | O | 3-Me, 5-NO₂ |
| 9 | O | 4-Me, 5-NO₂ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-NO₂ |
| 19 | S | 3-Me, 5-NO₂ |
| 20 | S | 4-Me, 5-NO₂ |
| 21 | S | 5-CN |
| 22 | S | 5-COOH |

TABLE 54

(I-J3)

[Structure: phosphate-O-C(CH3)2-CH(NH-SO2-heptyl)-thiophene(T)-(R²)n]

| No. | T | (R²)n |
|-----|---|-------|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-NO₂ |
| 8 | O | 3-Me, 5-NO₂ |
| 9 | O | 4-Me, 5-NO₂ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-NO₂ |
| 19 | S | 3-Me, 5-NO₂ |
| 20 | S | 4-Me, 5-NO₂ |
| 21 | S | 5-CN |
| 22 | S | 5-COOH |

TABLE 55

(I-K3)

[Structure: phosphate-O-CH2-CH(NH-C(=O)-NH-hexyl)-thiophene(T)-(R²)n]

| No. | T | (R²)n |
|-----|---|-------|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-NO₂ |
| 8 | O | 3-Me, 5-NO₂ |
| 9 | O | 4-Me, 5-NO₂ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-NO₂ |
| 19 | S | 3-Me, 5-NO₂ |
| 20 | S | 4-Me, 5-NO₂ |
| 21 | S | 5-CN |
| 22 | S | 5-COOH |

TABLE 56

(I-L3)

[Structure: phosphate-O-CH(CH3)-CH(NH-C(=O)-NH-hexyl)-thiophene(T)-(R²)n]

| No. | T | (R²)n |
|-----|---|-------|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-NO₂ |
| 8 | O | 3-Me, 5-NO₂ |
| 9 | O | 4-Me, 5-NO₂ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-NO₂ |
| 19 | S | 3-Me, 5-NO₂ |
| 20 | S | 4-Me, 5-NO₂ |
| 21 | S | 5-CN |
| 22 | S | 5-COOH |

TABLE 57

(I-M3)

| No. | T | (R²)ₙ |
|---|---|---|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-NO₂ |
| 8 | O | 3-Me, 5-NO₂ |
| 9 | O | 4-Me, 5-NO₂ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-NO₂ |
| 19 | S | 3-Me, 5-NO₂ |
| 20 | S | 4-Me, 5-NO₂ |
| 21 | S | 5-CN |
| 22 | S | 5-COOH |

TABLE 58

(I-N3)

| No. | T | (R²)ₙ |
|---|---|---|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-NO₂ |
| 8 | O | 3-Me, 5-NO₂ |
| 9 | O | 4-Me, 5-NO₂ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-NO₂ |
| 19 | S | 3-Me, 5-NO₂ |
| 20 | S | 4-Me, 5-NO₂ |
| 21 | S | 5-CN |
| 22 | S | 5-COOH |

TABLE 59

(I-O3)

| No. | T | (R²)ₙ |
|---|---|---|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-NO₂ |
| 8 | O | 3-Me, 5-NO₂ |
| 9 | O | 4-Me, 5-NO₂ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-NO₂ |
| 19 | S | 3-Me, 5-NO₂ |
| 20 | S | 4-Me, 5-NO₂ |
| 21 | S | 5-CN |
| 22 | S | 5-COOH |

TABLE 60

(I-P3)

| No. | T | (R²)ₙ |
|---|---|---|
| 1 | O | H |
| 2 | O | 3-Me |
| 3 | O | 4-Me |
| 4 | O | 5-Me |
| 5 | O | 3,4-di-Me |
| 6 | O | 3,5-di-Me |
| 7 | O | 5-NO₂ |
| 8 | O | 3-Me, 5-NO₂ |
| 9 | O | 4-Me, 5-NO₂ |
| 10 | O | 5-CN |
| 11 | O | 5-COOH |
| 12 | S | H |
| 13 | S | 3-Me |
| 14 | S | 4-Me |
| 15 | S | 5-Me |
| 16 | S | 3,4-di-Me |
| 17 | S | 3,5-di-Me |
| 18 | S | 5-NO₂ |
| 19 | S | 3-Me, 5-NO₂ |
| 20 | S | 4-Me, 5-NO₂ |
| 21 | S | 5-CN |
| 22 | S | 5-COOH |

TABLE 61

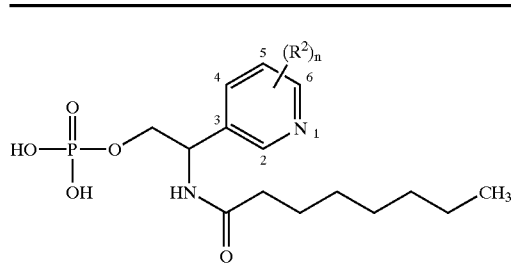
(I-A4)

| No. | (R²)n |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |
| 15 | 5-Me,4-OMe |
| 16 | 2-NO₂ |
| 17 | 5-NO₂ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-NO₂ |
| 27 | 4-Me,5-OH |
| 28 | 4-OH,5-NO₂ |
| 29 | 2-CN |
| 30 | 2-COOH |

TABLE 62

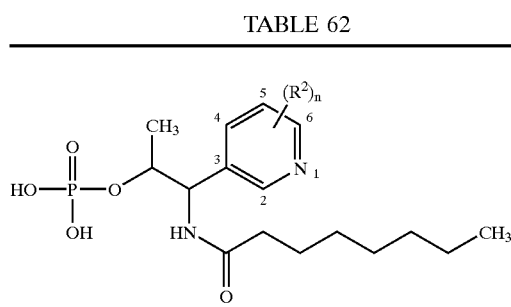
(I-B4)

| No. | (R²)n |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |

TABLE 62-continued

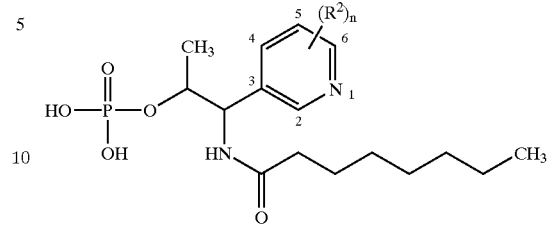
(I-B4)

| No. | (R²)n |
|---|---|
| 15 | 5-Me,4-OMe |
| 16 | 2-NO₂ |
| 17 | 5-NO₂ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-NO₂ |
| 27 | 4-Me,5-OH |
| 28 | 4-OH,5-NO₂ |
| 29 | 2-CN |
| 30 | 2-COOH |

TABLE 63

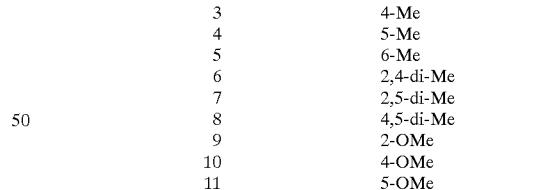
(I-C4)

| No. | (R²)n |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |
| 15 | 5-Me,4-OMe |
| 16 | 2-NO₂ |
| 17 | 5-NO₂ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-NO₂ |
| 27 | 4-Me,5-OH |
| 28 | 4-OH,5-NO₂ |

TABLE 63-continued
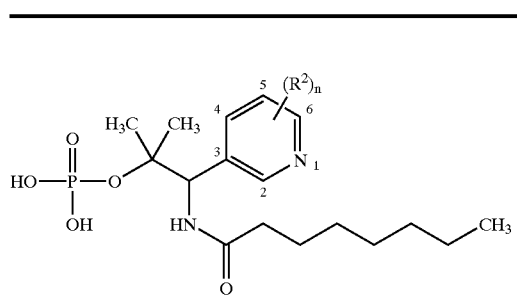
(I-C4)
| No. | $(R^2)_n$ |
|---|---|
| 29 | 2-CN |
| 30 | 2-COOH |
TABLE 64
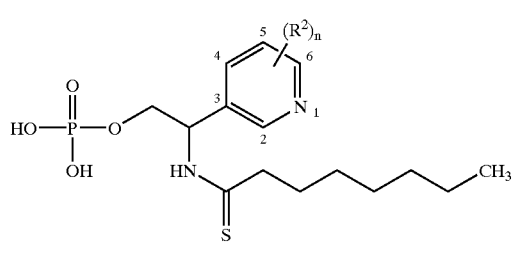
(I-D4)
| No. | $(R^2)_n$ |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |
| 15 | 5-Me,4-OMe |
| 16 | 2-NO$_2$ |
| 17 | 5-NO$_2$ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-NO$_2$ |
| 27 | 4-Me,5-OH |
| 28 | 4-OH,5-NO$_2$ |
| 29 | 2-CN |
| 30 | 2-COOH |
TABLE 65
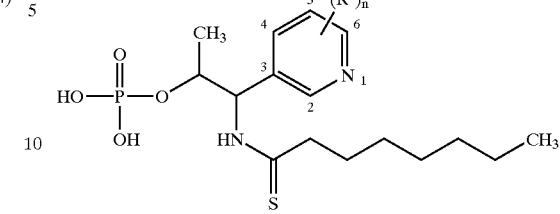
(I-E4)
| No. | $(R^2)_n$ |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |
| 15 | 5-Me,4-OMe |
| 16 | 2-NO$_2$ |
| 17 | 5-NO$_2$ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-NO$_2$ |
| 27 | 4-Me,5-OH |
| 28 | 4-OH,5-NO$_2$ |
| 29 | 2-CN |
| 30 | 2-COOH |
TABLE 66
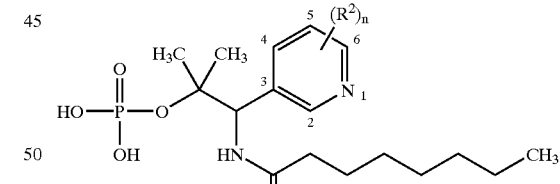
(I-F4)
| No. | $(R^2)_n$ |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |

TABLE 66-continued (I-F4)

| No. | (R²)ₙ |
|---|---|
| 15 | 5-Me,4-OMe |
| 16 | 2-NO₂ |
| 17 | 5-NO₂ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-NO₂ |
| 27 | 4-Me,5-OH |
| 28 | 4-OH,5-NO₂ |
| 29 | 2-CN |
| 30 | 2-COOH |

TABLE 67

(I-G4)

| No. | (R²)ₙ |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |
| 15 | 5-Me,4-OMe |
| 16 | 2-NO₂ |
| 17 | 5-NO₂ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-NO₂ |
| 27 | 4-Me,5-OH |
| 28 | 4-OH,5-NO₂ |

TABLE 67-continued (I-G4)

| No. | (R²)ₙ |
|---|---|
| 29 | 2-CN |
| 30 | 2-COOH |

TABLE 68

(I-H4)

| No. | (R²)ₙ |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |
| 15 | 5-Me,4-OMe |
| 16 | 2-NO₂ |
| 17 | 5-NO₂ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-NO₂ |
| 27 | 4-Me,5-OH |
| 28 | 4-OH,5-NO₂ |
| 29 | 2-CN |
| 30 | 2-COOH |

TABLE 69

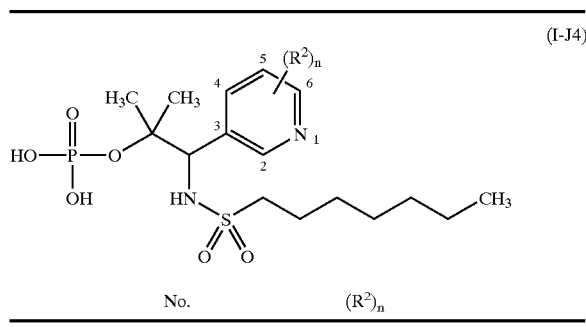

(I-J4)

| No. | $(R^2)_n$ |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |
| 15 | 5-Me,4-OMe |
| 16 | 2-$NO_2$ |
| 17 | 5-$NO_2$ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-$NO_2$ |
| 27 | 4-Me,5-OH |
| 28 | 4-OH,5-$NO_2$ |
| 29 | 2-CN |
| 30 | 2-COOH |

TABLE 70

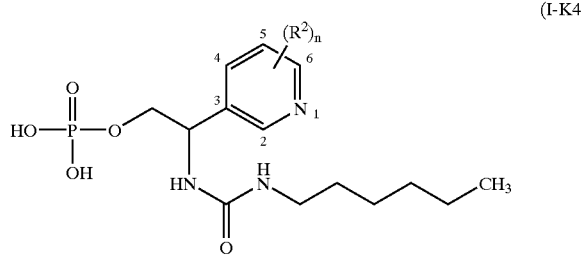

(I-K4)

| No. | $(R^2)_n$ |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |

TABLE 70-continued

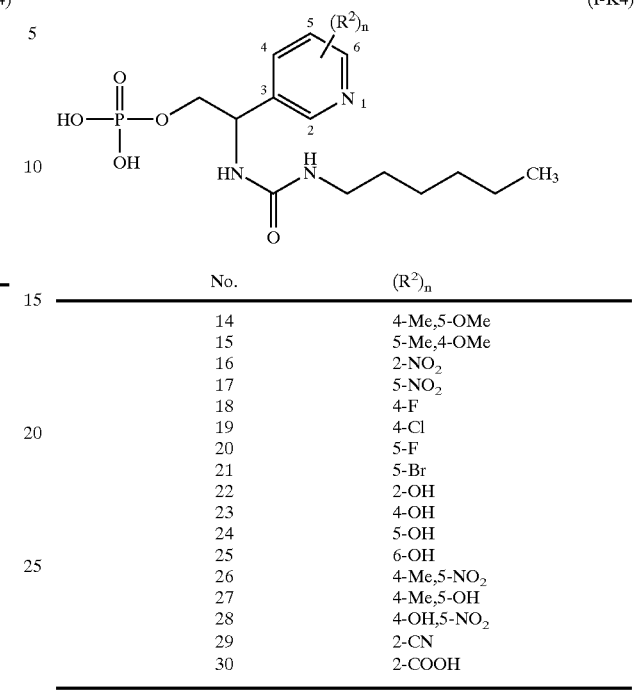

(I-K4)

| No. | $(R^2)_n$ |
|---|---|
| 14 | 4-Me,5-OMe |
| 15 | 5-Me,4-OMe |
| 16 | 2-$NO_2$ |
| 17 | 5-$NO_2$ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-$NO_2$ |
| 27 | 4-Me,5-OH |
| 28 | 4-OH,5-$NO_2$ |
| 29 | 2-CN |
| 30 | 2-COOH |

TABLE 71

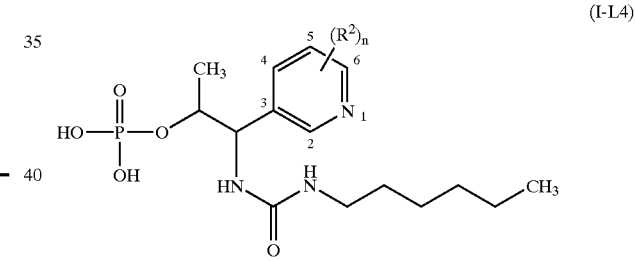

(I-L4)

| No. | $(R^2)_n$ |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |
| 15 | 5-Me,4-OMe |
| 16 | 2-$NO_2$ |
| 17 | 5-$NO_2$ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-$NO_2$ |

TABLE 71-continued

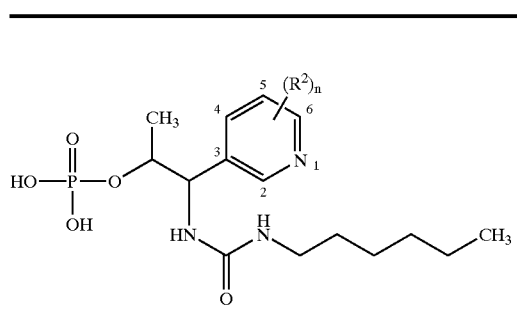
(I-L4)

| No. | $(R^2)_n$ |
|---|---|
| 27 | 4-Me,5-OH |
| 28 | 4-OH,5-NO$_2$ |
| 29 | 2-CN |
| 30 | 2-COOH |

TABLE 72

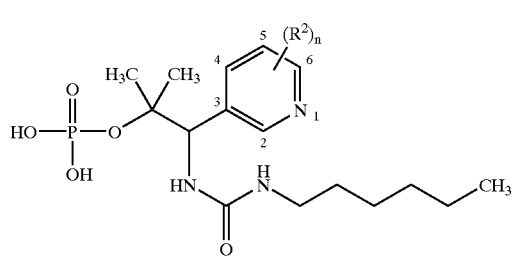
(I-M4)

| No. | $(R^2)_n$ |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |
| 15 | 5-Me,4-OMe |
| 16 | 2-NO$_2$ |
| 17 | 5-NO$_2$ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-NO$_2$ |
| 27 | 4-Me,5-OH |
| 28 | 4-OH,5-NO$_2$ |
| 29 | 2-CN |
| 30 | 2-COOH |

TABLE 73

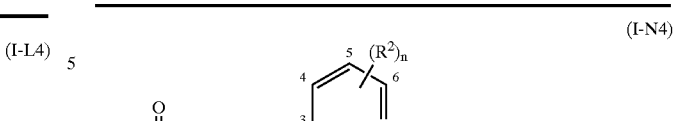
(I-N4)

| No. | $(R^2)_n$ |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |
| 15 | 5-Me,4-OMe |
| 16 | 2-NO$_2$ |
| 17 | 5-NO$_2$ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-NO$_2$ |
| 27 | 4-Me,5-OH |
| 28 | 4-OH,5-NO$_2$ |
| 29 | 2-CN |
| 30 | 2-COOH |

TABLE 74

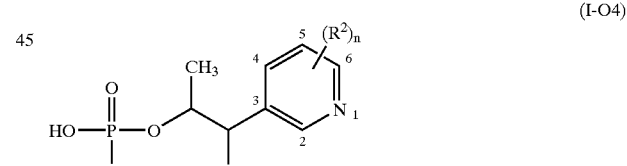
(I-O4)

| No. | $(R^2)_n$ |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |

TABLE 74-continued (I-O4)

| No. | (R²)ₙ |
|---|---|
| 15 | 5-Me,4-OMe |
| 16 | 2-NO₂ |
| 17 | 5-NO₂ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-NO₂ |
| 27 | 4-Me,5-OH |
| 28 | 4-OH,5-NO₂ |
| 29 | 2-CN |
| 30 | 2-COOH |

TABLE 75

(I-P4)

| No. | (R²)ₙ |
|---|---|
| 1 | H |
| 2 | 2-Me |
| 3 | 4-Me |
| 4 | 5-Me |
| 5 | 6-Me |
| 6 | 2,4-di-Me |
| 7 | 2,5-di-Me |
| 8 | 4,5-di-Me |
| 9 | 2-OMe |
| 10 | 4-OMe |
| 11 | 5-OMe |
| 12 | 6-OMe |
| 13 | 2-Me,5-OMe |
| 14 | 4-Me,5-OMe |
| 15 | 5-Me,4-OMe |
| 16 | 2-NO₂ |
| 17 | 5-NO₂ |
| 18 | 4-F |
| 19 | 4-Cl |
| 20 | 5-F |
| 21 | 5-Br |
| 22 | 2-OH |
| 23 | 4-OH |
| 24 | 5-OH |
| 25 | 6-OH |
| 26 | 4-Me,5-NO₂ |
| 27 | 4-Me,5-OH |
| 28 | 4-OH,5-NO₂ |

TABLE 75-continued (I-P4)

| No. | (R²)ₙ |
|---|---|
| 29 | 2-CN |
| 30 | 2-COOH |

TABLE 76

(I-A5)

| No. | (R²)ₙ |
|---|---|
| 1 | H |
| 2 | 3-Me |
| 3 | 3-OMe |
| 4 | 3-NO₂ |
| 5 | 3-F |
| 6 | 3-Cl |
| 7 | 3-OH |
| 8 | 3-CN |
| 9 | 3-COOH |
| 10 | 3-COOMe |
| 11 | 3-CONH₂ |
| 12 | 3-O—CH₂—OMe |
| 13 | 3-O—CH₂—COOEt |
| 14 | 3-CF₃ |
| 15 | 3-OCF₃ |
| 16 | 3-O—CH₂—Ph |
| 17 | 3-CH₂—OMe |
| 18 | 3-CH₂—COOEt |
| 19 | 3-O(CH₂)₂OH |
| 20 | 3-O(CH₂)₂NMe₂ |
| 21 | 3-O-CH(Me)₂ |
| 22 | 3-SMe |
| 23 | 3-SOMe |
| 24 | 3-SO₂Me |
| 25 | 3-NHSO₂Me |
| 26 | 3-NHCOMe |
| 27 | 3-NMe₂ |
| 28 | 3-NH₂ |
| 29 | 3-NHMe |
| 30 | 3-SCH₂OMe |
| 31 | 3-S(CH₂)₂OMe |
| 32 | 3-S(CH₂)₂COOEt |
| 33 | 3-S(CH₂)₂CONMe₂ |
| 34 | 3-CONMe₂ |
| 35 | 2,5-di-OMe |

TABLE 76-continued (I-A5)

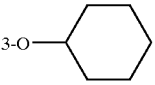

| No. | $(R^2)_n$ |
|---|---|
| 36 | 3-O-cyclohexyl 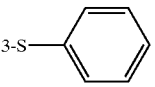 |
| 37 | 3-S-phenyl 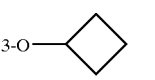 |
| 38 | 3-O-cyclobutyl 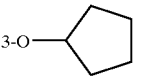 |
| 39 | 3-O-cyclopentyl 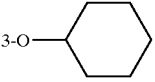 |
| 40 | 3-O-cyclohexyl 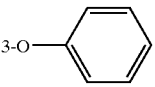 |
| 41 | 3-O-phenyl 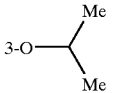 |

TABLE 77

(I-B5)

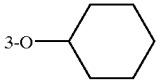

| No. | $(R^2)_n$ |
|---|---|
| 1 | H |
| 2 | 3-Me |
| 3 | 3-OMe |
| 4 | 3-NO$_2$ |
| 5 | 3-F |
| 6 | 3-Cl |
| 7 | 3-OH |
| 8 | 3-CN |
| 9 | 3-COOH |
| 10 | 3-COOMe |
| 11 | 3-CONH$_2$ |
| 12 | 3-O—CH$_2$—OMe |
| 13 | 3-O—CH$_2$—COOEt |
| 14 | 3-CF$_3$ |
| 15 | 3-OCF$_3$ |

TABLE 77-continued (I-B5)

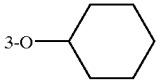

| No. | $(R^2)_n$ |
|---|---|
| 16 | 3-O—CH$_2$—Ph |
| 17 | 3-CH$_2$—OMe |
| 18 | 3-CH$_2$—COOEt |
| 19 | 3-O(CH$_2$)$_2$OH |
| 20 | 3-O(CH$_2$)$_2$NMe$_2$ |
| 21 | 3-O-CH(Me)$_2$ |
| 22 | 3-SMe |
| 23 | 3-SOMe |
| 24 | 3-SO$_2$Me |
| 25 | 3-NHSO$_2$Me |
| 26 | 3-NHCOMe |
| 27 | 3-NMe$_2$ |
| 28 | 3-NH$_2$ |
| 29 | 3-NHMe |
| 30 | 3-SCH$_2$OMe |
| 31 | 3-S(CH$_2$)$_2$OMe |
| 32 | 3-S(CH$_2$)$_2$COOEt |
| 33 | 3-S(CH$_2$)$_2$CONMe$_2$ |
| 34 | 3-CONMe$_2$ |
| 35 | 2,5-di-OMe |
| 36 | 3-O-cyclohexyl 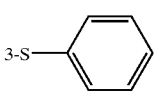 |
| 37 | 3-S-phenyl 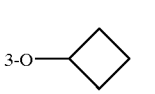 |
| 38 | 3-O-cyclobutyl 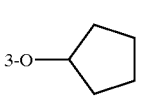 |
| 39 | 3-O-cyclopentyl 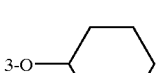 |
| 40 | 3-O-cyclohexyl |
| 41 | 3-O-phenyl 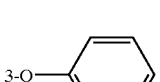 |

TABLE 78

(I-C5)

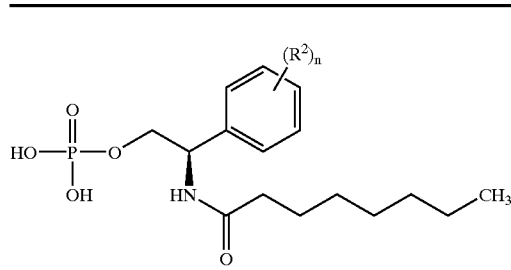

| No. | $(R^2)_n$ |
|---|---|
| 1 | H |
| 2 | 3-Me |
| 3 | 3-OMe |
| 4 | 3-NO$_2$ |
| 5 | 3-F |
| 6 | 3-Cl |
| 7 | 3-OH |
| 8 | 3-CN |
| 9 | 3-COOH |
| 10 | 3-COOMe |
| 11 | 3-CONH$_2$ |
| 12 | 3-O—CH$_2$—OMe |
| 13 | 3-O—CH$_2$—COOEt |
| 14 | 3-CF$_3$ |
| 15 | 3-OCF$_3$ |
| 16 | 3-O—CH$_2$—Ph |
| 17 | 3-CH$_2$—OMe |
| 18 | 3-CH$_2$—COOEt |
| 19 | 3-O(CH$_2$)$_2$OH |
| 20 | 3-O(CH$_2$)$_2$NMe$_2$ |
| 21 | 3-O—CHMe$_2$ |
| 22 | 3-SMe |
| 23 | 3-SOMe |
| 24 | 3-SO$_2$Me |
| 25 | 3-NHSO$_2$Me |
| 26 | 3-NHCOMe |
| 27 | 3-NMe$_2$ |
| 28 | 3-NH$_2$ |
| 29 | 3-NHMe |
| 30 | 3-SCH$_2$OMe |
| 31 | 3-S(CH$_2$)$_2$OMe |
| 32 | 3-S(CH$_2$)$_2$COOEt |
| 33 | 3-S(CH$_2$)$_2$CONMe$_2$ |
| 34 | 3-CONMe$_2$ |
| 35 | 2,5-di-OMe |
| 36 | 3-O-cyclohexyl |
| 37 | 3-S-phenyl |
| 38 | 3-O-cyclobutyl |
| 39 | 3-O-cyclopentyl |

TABLE 78-continued (I-C5)

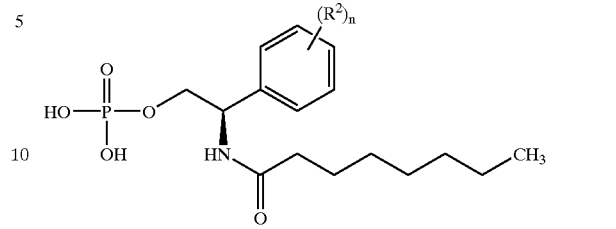

| No. | $(R^2)_n$ |
|---|---|
| 40 | 3-O-cyclohexyl |
| 41 | 3-O-phenyl |

TABLE 79

(I-D5)

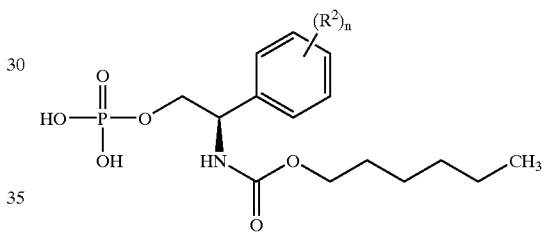

| No. | $(R^2)_n$ |
|---|---|
| 1 | H |
| 2 | 3-Me |
| 3 | 3-OMe |
| 4 | 3-NO$_2$ |
| 5 | 3-F |
| 6 | 3-Cl |
| 7 | 3-OH |
| 8 | 3-CN |
| 9 | 3-COOH |
| 10 | 3-COOMe |
| 11 | 3-CONH$_2$ |
| 12 | 3-O—CH$_2$—OMe |
| 13 | 3-O—CH$_2$—COOEt |
| 14 | 3-CF$_3$ |
| 15 | 3-OCF$_3$ |
| 16 | 3-O—CH$_2$—Ph |
| 17 | 3-CH$_2$—OMe |
| 18 | 3-CH$_2$—COOEt |
| 19 | 3-O(CH$_2$)$_2$OH |
| 20 | 3-O(CH$_2$)$_2$NMe$_2$ |
| 21 | 3-O—CHMe$_2$ |
| 22 | 3-SMe |
| 23 | 3-SOMe |
| 24 | 3-SO$_2$Me |
| 25 | 3-NHSO$_2$Me |
| 26 | 3-NHCOMe |
| 27 | 3-NMe$_2$ |
| 28 | 3-NH$_2$ |
| 29 | 3-NHMe |

TABLE 79-continued

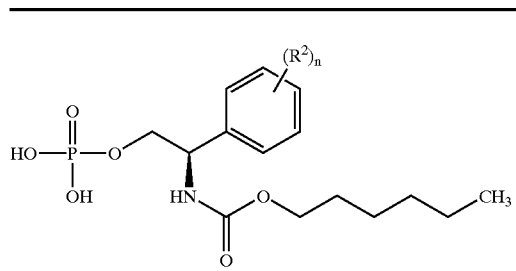

(I-D5)

| No. | $(R^2)_n$ |
|---|---|
| 30 | 3-SCH$_2$OMe |
| 31 | 3-S(CH$_2$)$_2$OMe |
| 32 | 3-S(CH$_2$)$_2$COOEt |
| 33 | 3-S(CH$_2$)$_2$CONMe$_2$ |
| 34 | 3-CONMe$_2$ |
| 35 | 2,5-di-OMe |
| 36 | 3-O-cyclohexyl |
| 37 | 3-S-phenyl |
| 38 | 3-O-cyclobutyl |
| 39 | 3-O-cyclopentyl |
| 40 | 3-O-cyclohexyl |
| 41 | 3-O-phenyl |

TABLE 80

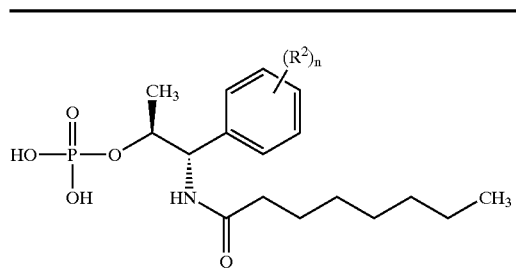

(I-E5)

| No. | $(R^2)_n$ |
|---|---|
| 1 | H |
| 2 | 3-Me |
| 3 | 3-OMe |
| 4 | 3-NO$_2$ |
| 5 | 3-F |
| 6 | 3-Cl |
| 7 | 3-OH |
| 8 | 3-CN |

TABLE 80-continued

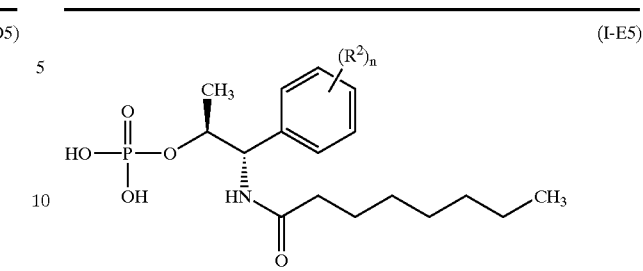

(I-E5)

| No. | $(R^2)_n$ |
|---|---|
| 9 | 3-COOH |
| 10 | 3-COOMe |
| 11 | 3-CONH$_2$ |
| 12 | 3-O—CH$_2$—OMe |
| 13 | 3-O—CH$_2$—COOEt |
| 14 | 3-CF$_3$ |
| 15 | 3-OCF$_3$ |
| 16 | 3-O—CH$_2$—Ph |
| 17 | 3-CH$_2$—OMe |
| 18 | 3-CH$_2$—COOEt |
| 19 | 3-O(CH$_2$)$_2$OH |
| 20 | 3-O(CH$_2$)$_2$NMe$_2$ |
| 21 | 3-O-CH(Me)$_2$ |
| 22 | 3-SMe |
| 23 | 3-SOMe |
| 24 | 3-SO$_2$Me |
| 25 | 3-NHSO$_2$Me |
| 26 | 3-NHCOMe |
| 27 | 3-NMe$_2$ |
| 28 | 3-NH$_2$ |
| 29 | 3-NHMe |
| 30 | 3-SCH$_2$OMe |
| 31 | 3-S(CH$_2$)$_2$OMe |
| 32 | 3-S(CH$_2$)$_2$COOEt |
| 33 | 3-S(CH$_2$)$_2$CONMe$_2$ |
| 34 | 3-CONMe$_2$ |
| 35 | 2,5-di-OMe |
| 36 | 3-O-cyclohexyl |
| 37 | 3-S-phenyl |
| 38 | 3-O-cyclobutyl |
| 39 | 3-O-cyclopentyl |
| 40 | 3-O-cyclohexyl |
| 41 | 3-O-phenyl |

TABLE 81

(I-F5)

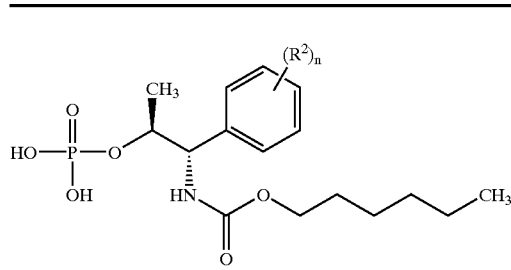

| No. | $(R^2)_n$ |
|---|---|
| 1 | H |
| 2 | 3-Me |
| 3 | 3-OMe |
| 4 | 3-$NO_2$ |
| 5 | 3-F |
| 6 | 3-Cl |
| 7 | 3-OH |
| 8 | 3-CN |
| 9 | 3-COOH |
| 10 | 3-COOMe |
| 11 | 3-$CONH_2$ |
| 12 | 3-O—$CH_2$—OMe |
| 13 | 3-O—$CH_2$—COOEt |
| 14 | 3-$CF_3$ |
| 15 | 3-$OCF_3$ |
| 16 | 3-O—$CH_2$—Ph |
| 17 | 3-$CH_2$—OMe |
| 18 | 3-$CH_2$—COOEt |
| 19 | 3-O$(CH_2)_2$OH |
| 20 | 3-O$(CH_2)_2NMe_2$ |
| 21 | 3-O—CH(Me)(Me) |
| 22 | 3-SMe |
| 23 | 3-SOMe |
| 24 | 3-$SO_2$Me |
| 25 | 3-$NHSO_2$Me |
| 26 | 3-NHCOMe |
| 27 | 3-$NMe_2$ |
| 28 | 3-$NH_2$ |
| 29 | 3-NHMe |
| 30 | 3-$SCH_2$OMe |
| 31 | 3-S$(CH_2)_2$OMe |
| 32 | 3-S$(CH_2)_2$COOEt |
| 33 | 3-S$(CH_2)_2CONMe_2$ |
| 34 | 3-$CONMe_2$ |
| 35 | 2,5-di-OMe |
| 36 | 3-O-cyclohexyl |
| 37 | 3-S-phenyl |
| 38 | 3-O-cyclobutyl |
| 39 | 3-O-cyclopentyl |

TABLE 81-continued (I-F5)

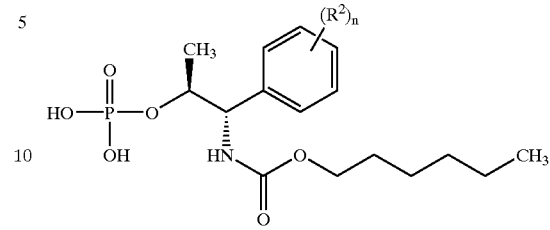

| No. | $(R^2)_n$ |
|---|---|
| 40 | 3-O-cyclohexyl |
| 41 | 3-O-phenyl |

TABLE 82

(I-G5)

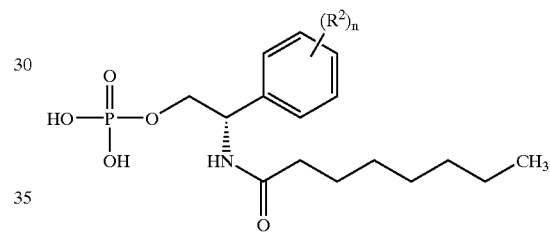

| No. | $(R^2)_n$ |
|---|---|
| 1 | H |
| 2 | 3-Me |
| 3 | 3-OMe |
| 4 | 3-$NO_2$ |
| 5 | 3-F |
| 6 | 3-Cl |
| 7 | 3-OH |
| 8 | 3-CN |
| 9 | 3-COOH |
| 10 | 3-COOMe |
| 11 | 3-$CONH_2$ |
| 12 | 3-O—$CH_2$—OMe |
| 13 | 3-O—$CH_2$—COOEt |
| 14 | 3-$CF_3$ |
| 15 | 3-$OCF_3$ |
| 16 | 3-O—$CH_2$—Ph |
| 17 | 3-$CH_2$—OMe |
| 18 | 3-$CH_2$—COOEt |
| 19 | 3-O$(CH_2)_2$OH |
| 20 | 3-O$(CH_2)_2NMe_2$ |
| 21 | 3-O—CH(Me)(Me) |
| 22 | 3-SMe |
| 23 | 3-SOMe |
| 24 | 3-$SO_2$Me |
| 25 | 3-$NHSO_2$Me |
| 26 | 3-NHCOMe |
| 27 | 3-$NMe_2$ |
| 28 | 3-$NH_2$ |
| 29 | 3-NHMe |

TABLE 82-continued

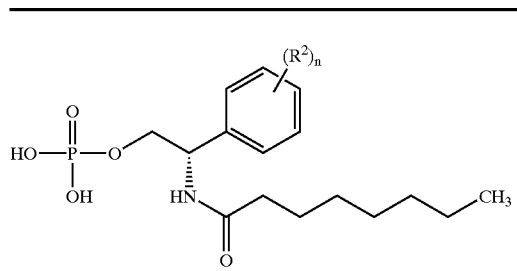

(I-G5)

| No. | $(R^2)_n$ |
|---|---|
| 30 | 3-SCH$_2$OMe |
| 31 | 3-S(CH$_2$)$_2$OMe |
| 32 | 3-S(CH$_2$)$_2$COOEt |
| 33 | 3-S(CH$_2$)$_2$CONMe$_2$ |
| 34 | 3-CONMe$_2$ |
| 35 | 2,5-di-OMe |
| 36 | 3-O—cyclohexyl |
| 37 | 3-S—phenyl |
| 38 | 3-O—cyclobutyl |
| 39 | 3-O—cyclopentyl |
| 40 | 3-O—cyclohexyl |
| 41 | 3-O—phenyl |

TABLE 83

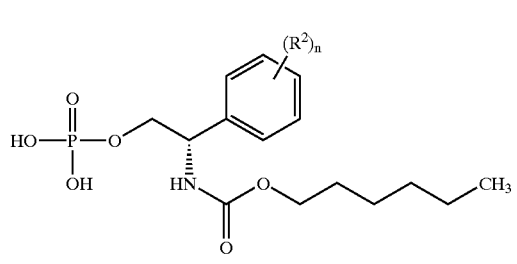

(I-H5)

| No. | $(R^2)_n$ |
|---|---|
| 1 | H |
| 2 | 3-Me |
| 3 | 3-OMe |
| 4 | 3-NO$_2$ |
| 5 | 3-F |
| 6 | 3-Cl |
| 7 | 3-OH |
| 8 | 3-CN |

TABLE 83-continued

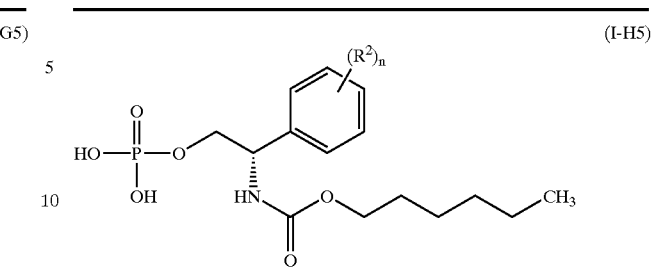

(I-H5)

| No. | $(R^2)_n$ |
|---|---|
| 9 | 3-COOH |
| 10 | 3-COOMe |
| 11 | 3-CONH$_2$ |
| 12 | 3-O—CH$_2$—OMe |
| 13 | 3-O—CH$_2$—COOEt |
| 14 | 3-CF$_3$ |
| 15 | 3-OCF$_3$ |
| 16 | 3-O—CH$_2$—Ph |
| 17 | 3-CH$_2$—OMe |
| 18 | 3-CH$_2$—COOEt |
| 19 | 3-O(CH$_2$)$_2$OH |
| 20 | 3-O(CH$_2$)$_2$NMe$_2$ |
| 21 | 3-O—CH(Me)$_2$ |
| 22 | 3-SMe |
| 23 | 3-SOMe |
| 24 | 3-SO$_2$Me |
| 25 | 3-NHSO$_2$Me |
| 26 | 3-NHCOMe |
| 27 | 3-NMe$_2$ |
| 28 | 3-NH$_2$ |
| 29 | 3-NHMe |
| 30 | 3-SCH$_2$OMe |
| 31 | 3-S(CH$_2$)$_2$OMe |
| 32 | 3-S(CH$_2$)$_2$COOEt |
| 33 | 3-S(CH$_2$)$_2$CONMe$_2$ |
| 34 | 3-CONMe$_2$ |
| 35 | 2,5-di-OMe |
| 36 | 3-O—cyclohexyl |
| 37 | 3-S—phenyl |
| 38 | 3-O—cyclobutyl |
| 39 | 3-O—cyclopentyl |
| 40 | 3-O—cyclohexyl |
| 41 | 3-O—phenyl |

TABLE 84

(I-J5)

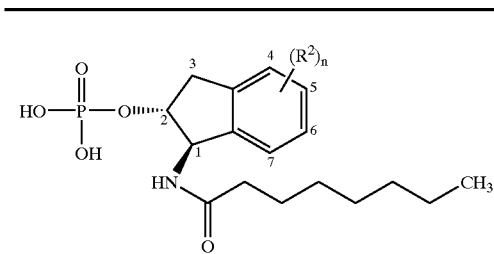

| No. | (R²)ₙ |
|---|---|
| 1 | H |
| 2 | 4-Me |
| 3 | 4-OMe |
| 4 | 4-NO₂ |
| 5 | 4-F |
| 6 | 4-Cl |
| 7 | 4-OH |
| 8 | 4-CN |
| 9 | 4-COOH |
| 10 | 4-COOMe |
| 11 | 4-CONH₂ |
| 12 | 4-O—CH₂—OMe |
| 13 | 4-O—CH₂—COOEt |
| 14 | 4-CF₃ |
| 15 | 4-OCF₃ |
| 16 | 4-O—CH₂—Ph |
| 17 | 4-CH₂—OMe |
| 18 | 4-CH₂—COOEt |
| 19 | 4-O(CH₂)₂OH |
| 20 | 4-O(CH₂)₂NMe₂ |
| 21 | 4-O—CH(Me)Me |
| 22 | 4-SMe |
| 23 | 4-SOMe |
| 24 | 4-SO₂Me |
| 25 | 4-NHSO₂Me |
| 26 | 4-NHCOMe |
| 27 | 4-NMe₂ |
| 28 | 4-NH₂ |
| 29 | 4-NHMe |
| 30 | 4-SCH₂OMe |
| 31 | 4-S(CH₂)₂OMe |
| 32 | 4-S(CH₂)₂COOEt |
| 33 | 4-S(CH₂)₂CONMe₂ |
| 34 | 4-CONMe₂ |
| 35 | 4,7-di-OMe |
| 36 | 4-S-cyclohexyl |
| 37 | 4-S-phenyl |
| 38 | 4-O-cyclobutyl |
| 39 | 4-O-cyclopentyl |
| 40 | 4-O-cyclopentyl |

TABLE 84-continued (I-J5)

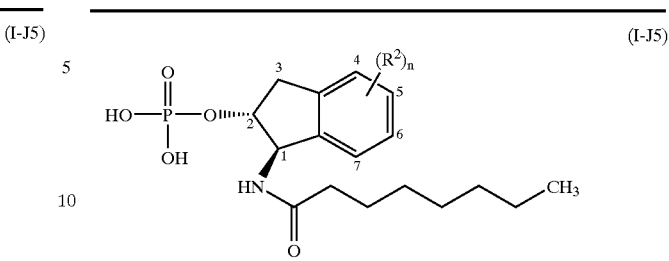

| No. | (R²)ₙ |
|---|---|
| 41 | 4-O-phenyl |

TABLE 85

(I-K5)

| No. | (R²)ₙ |
|---|---|
| 1 | H |
| 2 | 4-Me |
| 3 | 4-OMe |
| 4 | 4-NO₂ |
| 5 | 4-F |
| 6 | 4-Cl |
| 7 | 4-OH |
| 8 | 4-CN |
| 9 | 4-COOH |
| 10 | 4-COOMe |
| 11 | 4-CONH₂ |
| 12 | 4-O—CH₂—OMe |
| 13 | 4-O—CH₂—COOEt |
| 14 | 4-CF₃ |
| 15 | 4-OCF₃ |
| 16 | 4-O—CH₂—Ph |
| 17 | 4-CH₂—OMe |
| 18 | 4-CH₂—COOEt |
| 19 | 4-O(CH₂)₂OH |
| 20 | 4-O(CH₂)₂NMe₂ |
| 21 | 4-O—CH(Me)Me |
| 22 | 4-SMe |
| 23 | 4-SOMe |
| 24 | 4-SO₂Me |
| 25 | 4-NHSO₂Me |
| 26 | 4-NHCOMe |
| 27 | 4-NMe₂ |
| 28 | 4-NH₂ |
| 29 | 4-NHMe |
| 30 | 4-SCH₂OMe |
| 31 | 4-S(CH₂)₂OMe |
| 32 | 4-S(CH₂)₂COOEt |
| 33 | 4-S(CH₂)₂CONMe₂ |
| 34 | 4-CONMe₂ |

TABLE 85-continued

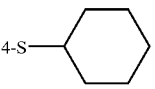

(I-K5)

| No. | (R²)ₙ |
|---|---|
| 35 | 4,7-di-OMe |
| 36 | 4-S-cyclohexyl |
| 37 | 4-S-phenyl |
| 38 | 4-O-cyclobutyl |
| 39 | 4-O-cyclopentyl |
| 40 | 4-O-cyclopentyl |
| 41 | 4-O-phenyl |

TABLE 86

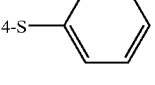

(I-L5)

| No. | (R²)ₙ |
|---|---|
| 1 | H |
| 2 | 5-Me |
| 3 | 5-OMe |
| 4 | 5-NO₂ |
| 5 | 5-F |
| 6 | 5-Cl |
| 7 | 5-OH |
| 8 | 5-CN |
| 9 | 5-COOH |
| 10 | 5-COOMe |
| 11 | 5-CONH₂ |
| 12 | 5-O—CH₂—OMe |
| 13 | 5-O—CH₂—COOEt |
| 14 | 5-CF₃ |
| 15 | 5-OCF₃ |

TABLE 86-continued

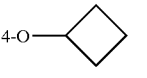

(I-L5)

| No. | (R²)ₙ |
|---|---|
| 16 | 5-O—CH₂—Ph |
| 17 | 5-CH₂—OMe |
| 18 | 5-CH₂—COOEt |
| 19 | 5-O(CH₂)₂OH |
| 20 | 5-O(CH₂)₂NMe₂ |
| 21 | 5-O—CH(Me)₂ |
| 22 | 5-SMe |
| 23 | 5-SOMe |
| 24 | 5-SO₂Me |
| 25 | 5-NHSO₂Me |
| 26 | 5-NHCOMe |
| 27 | 5-NMe₂ |
| 28 | 5-NH₂ |
| 29 | 5-NHMe |
| 30 | 5-SCH₂OMe |
| 31 | 5-S(CH₂)₂OMe |
| 32 | 5-S(CH₂)₂COOEt |
| 33 | 5-S(CH₂)₂CONMe₂ |
| 34 | 5-CONMe₂ |
| 35 | 5,7-di-OMe |
| 36 | 5-S-cyclohexyl |
| 37 | 5-S-phenyl |
| 38 | 5-O-cyclobutyl |
| 39 | 5-O-cyclopentyl |
| 40 | 5-O-cyclohexyl |
| 41 | 5-O-phenyl |

TABLE 87

(I-M5)

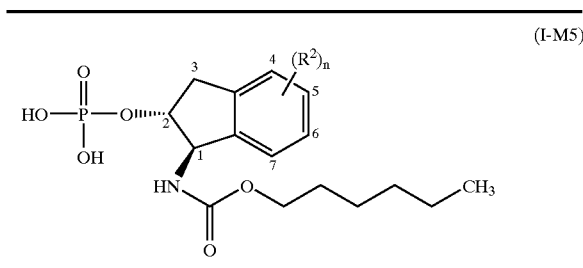

| No. | $(R^2)_n$ |
|---|---|
| 1 | H |
| 2 | 5-Me |
| 3 | 5-OMe |
| 4 | 5-NO$_2$ |
| 5 | 5-F |
| 6 | 5-Cl |
| 7 | 5-OH |
| 8 | 5-CN |
| 9 | 5-COOH |
| 10 | 5-COOMe |
| 11 | 5-CONH$_2$ |
| 12 | 5-O—CH$_2$—OMe |
| 13 | 5-O—CH$_2$—COOEt |
| 14 | 5-CF$_3$ |
| 15 | 5-OCF$_3$ |
| 16 | 5-O—CH$_2$—Ph |
| 17 | 5-CH$_2$—OMe |
| 18 | 5-CH$_2$—COOEt |
| 19 | 5-O(CH$_2$)$_2$OH |
| 20 | 5-O(CH$_2$)$_2$NMe$_2$ |
| 21 | 5-O—CH(Me)$_2$ |
| 22 | 5-SMe |
| 23 | 5-SOMe |
| 24 | 5-SO$_2$Me |
| 25 | 5-NHSO$_2$Me |
| 26 | 5-NHCOMe |
| 27 | 5-NMe$_2$ |
| 28 | 5-NH$_2$ |
| 29 | 5-NHMe |
| 30 | 5-SCH$_2$OMe |
| 31 | 5-S(CH$_2$)$_2$OMe |
| 32 | 5-S(CH$_2$)$_2$COOEt |
| 33 | 5-S(CH$_2$)$_2$CONMe$_2$ |
| 34 | 5-CONMe$_2$ |
| 35 | 5,7-di-OMe |
| 36 | 5-S-cyclohexyl |
| 37 | 5-S-phenyl |
| 38 | 5-O-cyclobutyl |
| 39 | 5-O-cyclopentyl |
| 40 | 5-O-cyclohexyl |

TABLE 87-continued (I-M5)

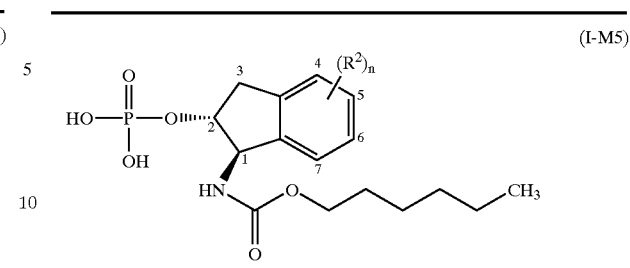

| No. | $(R^2)_n$ |
|---|---|
| 41 | 5-O-phenyl |

TABLE 88

(I-N5)

| No. | $(R^2)_n$ |
|---|---|
| 1 | H |
| 2 | 6-Me |
| 3 | 6-OMe |
| 4 | 6-NO$_2$ |
| 5 | 6-F |
| 6 | 6-Cl |
| 7 | 6-OH |
| 8 | 6-CN |
| 9 | 6-COOH |
| 10 | 6-COOMe |
| 11 | 6-CONH$_2$ |
| 12 | 6-O—CH$_2$—OMe |
| 13 | 6-O—CH$_2$—COOEt |
| 14 | 6-CF$_3$ |
| 15 | 6-OCF$_3$ |
| 16 | 6-O—CH$_2$—Ph |
| 17 | 6-CH$_2$—OMe |
| 18 | 6-CH$_2$—COOEt |
| 19 | 6-O(CH$_2$)$_2$OH |
| 20 | 6-O(CH$_2$)$_2$NMe$_2$ |
| 21 | 6-O—CH(Me)$_2$ |
| 22 | 6-SMe |
| 23 | 6-SOMe |
| 24 | 6-SO$_2$Me |
| 25 | 6-NHSO$_2$Me |
| 26 | 6-NHCOMe |
| 27 | 6-NMe$_2$ |
| 28 | 6-NH$_2$ |
| 29 | 6-NHMe |
| 30 | 6-SCH$_2$OMe |
| 31 | 6-S(CH$_2$)$_2$OMe |
| 32 | 6-S(CH$_2$)$_2$COOEt |
| 33 | 6-S(CH$_2$)$_2$CONMe$_2$ |
| 34 | 6-CONMe$_2$ |

TABLE 88-continued (I-N5)

[Structure: indane with phosphate at position 2, HN-C(=O)-heptyl at position 1, (R²)ₙ on aromatic ring]

| No. | (R²)ₙ |
|---|---|
| 35 | 4,6-di-OMe |
| 36 | 6-S-cyclohexyl |
| 37 | 6-S-phenyl |
| 38 | 6-O-cyclobutyl |
| 39 | 6-O-cyclopentyl |
| 40 | 6-O-cyclohexyl |
| 41 | 6-O-phenyl |

TABLE 89

(I-O5)

[Structure: indane with phosphate at position 2, HN-C(=O)-O-hexyl carbamate at position 1, (R²)ₙ on aromatic ring]

| No. | (R²)ₙ |
|---|---|
| 1 | H |
| 2 | 6-Me |
| 3 | 6-OMe |
| 4 | 6-NO₂ |
| 5 | 6-F |
| 6 | 6-Cl |
| 7 | 6-OH |
| 8 | 6-CN |
| 9 | 6-COOH |
| 10 | 6-COOMe |
| 11 | 6-CONH₂ |
| 12 | 6-O—CH₂—OMe |
| 13 | 6-O—CH₂—COOEt |
| 14 | 6-CF₃ |
| 15 | 6-OCF₃ |

TABLE 89-continued (I-O5)

| No. | (R²)ₙ |
|---|---|
| 16 | 6-O—CH₂—Ph |
| 17 | 6-CH₂—OMe |
| 18 | 6-CH₂—COOEt |
| 19 | 6-O(CH₂)₂OH |
| 20 | 6-O(CH₂)₂NMe₂ |
| 21 | 6-O-CH(Me)₂ |
| 22 | 6-SMe |
| 23 | 6-SOMe |
| 24 | 6-SO₂Me |
| 25 | 6-NHSO₂Me |
| 26 | 6-NHCOMe |
| 27 | 6-NMe₂ |
| 28 | 6-NH₂ |
| 29 | 6-NHMe |
| 30 | 6-SCH₂OMe |
| 31 | 6-S(CH₂)₂OMe |
| 32 | 6-S(CH₂)₂COOEt |
| 33 | 6-S(CH₂)₂CONMe₂ |
| 34 | 6-CONMe₂ |
| 35 | 4,6-di-OMe |
| 36 | 6-S-cyclohexyl |
| 37 | 6-S-phenyl |
| 38 | 6-O-cyclobutyl |
| 39 | 6-O-cyclopentyl |
| 40 | 6-O-cyclohexyl |
| 41 | 6-O-phenyl |

Unless otherwise specified, all isomers are included in the present invention. For example, alkyl, alkoxy, alkylthio, alkenyl, alkynyl and alkylene include straight and branched isomers. Isomers in the double bonds, rings, fused rings (E, Z, cis, trans isomers), isomers generated by the existence of asymmetric carbon atom(s) (R, S isomers, α, β isomers, enantiomers, diastereomers), optically active isomers having optically rotatory power (D, L, d, l isomers, +, − isomers), polar isomers separated by chromatography (more polar, less polar isomers), equilibrium compounds, arbitrary ratios of these compounds, racemic mixtures are all included in the present invention. Optically active isomers of formula (I) in the present invention may be obtained by general methods of optically separation (for example, separation by gas chromatography or high performance liquid chromatography, separation by crystallization as diastereomeric salts or clathrates, separation by prior crystallization etc.) or may be prepared by general methods of asymmetric synthesis.

[Salt]

The compounds of formula (I) of the present invention may be converted into the corresponding salts by conventional method. Non-toxic and water-soluble salts are preferred. Suitable salts, for example, include: salts of alkali metals (e.g. potassium, sodium, etc.), salts of alkaline earth metals (e.g. calcium, magnesium, etc.), ammonium salts, salts of pharmaceutically acceptable organic amines (e.g. tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, etc.). Salts of alkali metals are preferably.

The compounds of formula (I) of the present invention and salts thereof may be converted into the corresponding hydrates by conventional means.

[Processes for the Preparation of the Compound of the Present Invention]

The compounds of formula (I) of the present invention may be prepared by following, described in example or known methods.

(1) In the compounds of the formula (I), the compounds in which all of $R^1$ and $R^2$ do not contain carboxyl, hydroxy or amino, and all of $R^3$ and $R^4$ do not contain hydroxy, that is the compounds of the formula (IA)

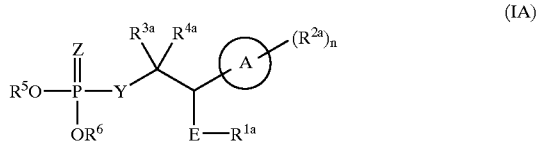

(IA)

wherein $R^{1a}$ and $R^{2a}$ are the same meaning as $R^1$ and $R^2$ respectively, provided that, when at least one of $R^1$ and $R^2$ represent contain carboxyl, hydroxy or amino, then each carboxyl, hydroxy or amino is protected by protective group, $R^{3a}$ and $R^{4a}$ are the same meaning as $R^3$ and $R^4$ respectively, provided that, when at least one of $R^3$ and $R^4$ represent contain hydroxy, then the hydroxy is protected by protective group, and the other symbols are the same meaning as hereinbefore defined may be prepared by following method (1-1), (1-2) or (1-3).

(1-1) In the compounds of the formula (IA), the compounds in which all of $R^5$ and $R^6$ do not represent a hydrogen atom, that is the compounds of the formula (IA-1)

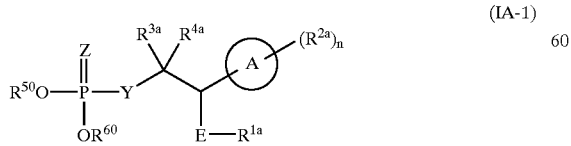

(IA-1)

wherein $R^{50}$ and $R^{60}$ each, independently, is C1–8 alkyl, phenyl, C1–4 alkyl substituted by phenyl, C1–4 alkyl substituted by trihalomethyl or C1–4 alkyl substituted by cyano, may be prepared by reacting the formula (X-1)

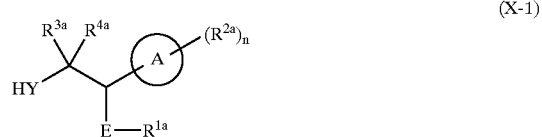

(X-1)

wherein all symbols are the same meaning as hereinbefore defined with the compound of the formula (X-2)

(X-2)

wherein X is a halogen atom or hydroxy, and the other symbols are the same meaning as hereinbefore defined.

The reaction of the compound of the formula (X-1) with the compound of the formula (X-2) is known per se, for example, when X is a halogen atom, then the reaction may be carried out in the presence of a tertiary amine (pyridine, triethylamine, dimethylaniline or dimethylaminopyridine, etc.) in an organic solvent (chloroform, methylene chloride, diethyl ether or tetrahydrofuran, etc.), at a temperature of from 0° C. to 40° C. When X is hydroxy, then the reaction may be carried out in the presence of an azo compound (diethyl azodicarboxylate, diisopropyl azodicarboxylate, 1,1'-(azodicarbonyl)dipiperidine, 1,1'-azobis(N,N-dimethylformamide), etc.) and a phosphine compound (triphenylphosphine, tributylphosphine, trimethylphosphine, etc.) in an inert organic solvent (methylene chloride, diethyl ether, tetrahydrofuran, acetone, benzene, toluene, etc.), at a temperature of from 0° C. to 60° C.

In the compounds of the formula (IA-1), the compounds in which all of $R^{1a}$ and $R^{2a}$ do not contain —S— or —S(O)—, that is the compounds of the formula (IA-1-X)

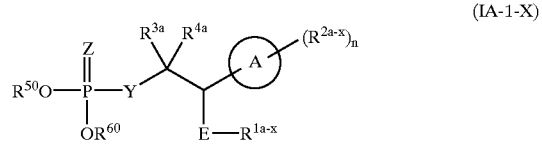

(IA-1-X)

wherein $R^{1a\text{-}x}$ and $R^{2a\text{-}x}$ are the same meaning as $R^{1a}$ and $R^{2a}$, with the proviso that, all of $R^{1a}$ and $R^{2a}$ do not contain —S— and —S(O)—, and other symbols are the same meaning as hereinbefore defined may be prepared by reacting the compound of the formula (X-1-X),

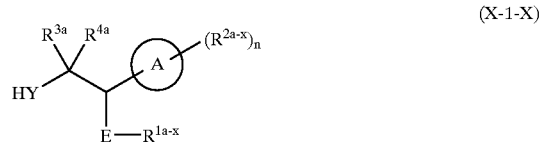

(X-1-X)

wherein all symbols are the same meaning as hereinbefore defined which in the compound of the formula (X-1), all of $R^{1a}$ and $R^{2a}$ do not contain —S— and —S(O)— with the compound of the formula (X-3)

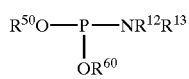 (X-3)

wherein $R^{12}$ and $R^{13}$ each, independently, is C1–8 alkyl, and the other symbols are the same meaning as hereinbefore defined followed by oxidation.

The reaction of the compound of the formula (X-1-X) with the compound of the formula (X-3) may be carried out in the presence of tetrazole in an inert organic solvent (acetonitrile, tetrahydrofuran, diethyl ether, methylene chloride, chloroform, etc.), at a temperature of from 0° C. to 40° C.

Above-mentioned oxidation may be carried out in a solvent (acetonitrile, methylene chloride, water, etc.) in the presence of oxidant (3-chloroperoxybenzoic acid, iodine, hydrogen peroxide, t-butyl hydroperoxide, 3H-1,2-benzothiol-3-one 1,1-dioxide, etc.) at a temperature of from 0° C. to 40° C.

(1-2) In the compounds of the formula (IA), in which $R^5$ and $R^6$ are a hydrogen atom, that is the compounds of the formula (IA-2)

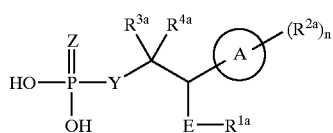 (IA-2)

wherein all symbols are the same meaning as hereinbefore defined may be prepared by subjecting to a deprotection reaction of the protective group for phosphoric acid.

The deprotection reaction of the protective group for phosphoric acid is known per se, for example, (a) Elimination of C1–2 alkyl may be carried out in an organic solvent (chloroform, etc.) in the presence of trimethylsilyl halide (trimethylsilyl chloride, trimethylsilyl bromide or trimethylsilyl iodide, etc.) in the presence or absence of alkali metal iodide (sodium iodide or potassium iodide, etc.) at a temperature of from 0° C. to 40° C.

(b) Elimination of phenyl may be carried out under an atmosphere of hydrogen, in an organic solvent (methanol, ethanol or tetrahydrofuran, etc.) or without a solvent in the presence of catalyst (platinum dioxide, etc.), and in the presence or absence of organic acid (acetic acid, etc.) or inorganic acid (hydrochloric acid, etc.) for 24 hours to 3 days at a temperature of from 0° C. to 50° C.

(c) Elimination of benzyl may be carried out under an atmosphere of hydrogen, in an organic solvent (methanol, ethanol, tetrahydrofuran, pyridine or acetic acid, etc.) in the presence of catalyst (palladium-carbon, palladium black or palladium hydroxide, etc.) at a temperature of from 0° C. to 50° C.

(d) Elimination of 2,2,2-trichloroethyl may be carried out in an organic solvent (methanol, ethanol or tetrahydrofuran, etc.) or without a solvent, using zinc powder and organic acid (acetic acid, etc.) or inorganic acid (hydrochloric acid, etc.) at a temperature of from 0° C. to 50° C.

The compounds in which $R^{1a}$ represent contains alkenyl or alkynyl ay be prepared by subjecting to a deprotection reaction that above-mentioned method (a) or (d).

The compound in which $R^{1a}$ dose not contain alkenyl or alkynyl may be prepared by subjecting to a deprotection reaction that above-mentioned method from (a) to (d). With the proviso that, when $Cyc^1$ and/or A ring represented by $R^1$ is carbocyclic aryl or heterocyclic aryl, then the compound may be prepared by subjecting to a deprotection reaction that above-mentioned method (a) or (c)–(d), and when nitro is containing in $R^1$ or $R^2$, then the compound may be prepared by subjecting to a deprotection reaction that above-mentioned method (a) or (d).

(1-3) In the compounds of the formula (IA), the compounds in which one of $R^5$ or $R^6$ is a hydrogen atom and the other is not a hydrogen atom, that is the compounds of the formula (IA-3)

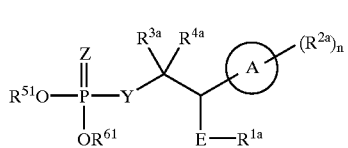 (IA-3)

wherein one of $R^{51}$ or $R^{61}$ is a hydrogen atom and the other is C1–8 alkyl, phenyl, C1–4 alkyl substituted by phenyl, C1–4 alkyl substituted by trihalomethyl or C1–4 alkyl substituted by cyano, and the other symbols are the same meaning as hereinbefore defined may be prepared by following method (1-3-a) or (1-3-b).

(1-3-a) The compound of the formula (IA-3) may be prepared by subjecting to a deprotection reaction of the protective group for phosphoric acid of the compound of the formula (IA-1) hereinbefore described.

This deprotection reaction of the protective group for phosphoric acid may be carried out under some condition hereinafter described, and depends on the protective group, for example, (1) in organic solvent (diethyl ether, methanol, tetrahydrofuran or dioxane, etc.) using hydroxide of alkali metal (sodium hydroxide or potassium hydroxide, etc.) or an aqueous solution thereof or a mixture thereof at a temperature of from 0° C. to 40° C., (2) in organic solvent (tetrahydrofuran or pyridine, etc.), using t-butylamine or tetrabutylammonium hydroxide at a temperature of from 0° C. to 100° C., or (3) in organic solvent (2-ethoxyethanol or acetone, etc.), using lithium halide (lithium chloride or lithium bromide, etc.) under reflux condition.

(1-3-b) In the compounds of formula (IA-3), the compounds in which one of $R^{51}$ or $R^{61}$ is a hydrogen and the other is phenyl, $R^{1a}$ does not contain alkenyl or alkynyl, that is the compounds of the formula (IA-3-B)

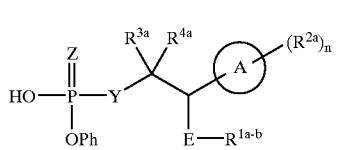 (IA-3-B)

wherein Ph is phenyl, $R^{1a-b}$ is the same meaning as $R^{1a}$, provided that, $R^{1a}$ does not contain alkenyl or alkynyl, and the other symbols are the same meaning as hereinbefore defined may be prepared by subjecting to a deprotection reaction of the protective group for phosphoric acid of the compound of the formula (IA-1-B)

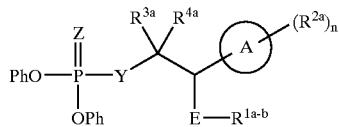

(IA-1-B)

wherein all symbols are the same meaning as hereinbefore defined.

The elimination reaction of protective group for phosphoric acid may be carried out under an atmosphere of hydrogen, in an organic solvent (methanol, ethanol, tetrahydrofuran, etc.) or without a solvent in the presence of catalyst (platinum dioxide, etc.), in the presence or absence of organic acid (acetic acid, etc.) or inorganic acid (hydrochloric acid, etc.) for 1–3 hours at a temperature of from 0° C. to 50° C.

(I-4) In the compound of formula (IA), the compounds in which one of $R^{1a}$ or $R^{2a}$ represent contains —S(O)— or —S(O)$_2$—, that is the compounds of the formula (IA-4)

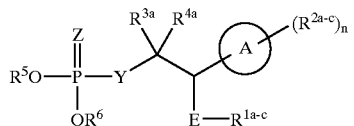

(IA-4)

wherein $R^{1a-c}$ and $R^{2a-c}$ are the same meaning as $R^{1a}$ and $R^{2a}$, respectively, provided that, one of $R^{1a}$ or $R^{2a}$ represent contains —S(O)— or —S(O)$_2$—, and the other symbols are the same meaning as hereinbefore defined may be prepared by oxidation among the compound of formula (IA-1), (IA-2) or (IA-3) hereinbefore described, the compounds in which one of $R^{1a}$ or $R^{2a}$ represent contains —S—, that is the compounds of the formula (IA-5).

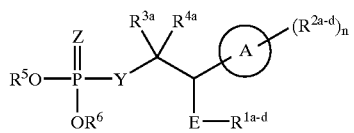

(IA-5)

wherein $R^{1a-d}$ and $R^{2a-d}$ are the same meaning as $R^{1a}$ and $R^{2a}$, respectively, provided that, one of $R^{1a}$ or $R^{2a}$ represent contains —S—, and the other symbols are the same meaning as hereinbefore defined.

The oxidation is known per se, and may be carried out, for example, in suitable organic solvent (methylene chloride, chloroform, benzene, hexane, t-butylalcohol, etc.) in the presence of oxidant (hydrogen peroxide, sodium periodate, acyl nitrites, sodium perborate, a peroxide (for example, 3-chloroperbenzoic acid or peroxiacetic acid, etc.), potassium peroxomonosulfate, potassium permanganate, chromic acid, etc.) at a temperature of from 20° C. to 60° C.

Above-mentioned the compounds of the formula (X-1) may be prepared by the method described in the following reaction scheme 1.

In the scheme, all symbols are the same meaning as hereinbefore defined, and all reaction may be carried out as the methods hereinafter described in (1A-1-a), (1A-1-b), (1A-1-c), (1A-1-d-1), (1A-1-d-2), (1A-1-e) and (1A-1-f).

Reaction Scheme 1

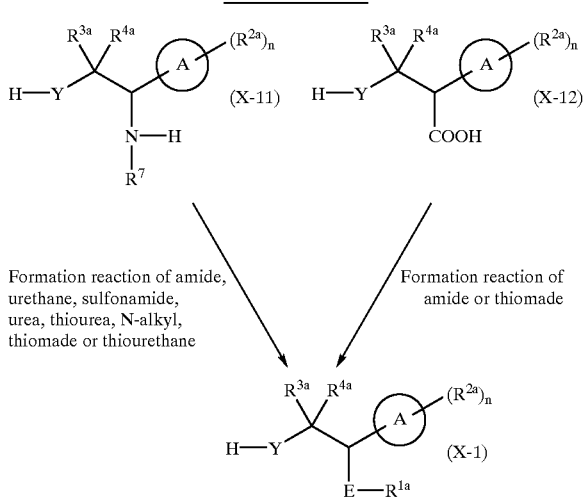

In the compounds of the formula (IA-1), the compounds in which E is not —CONR$^7$— or —CSNR$^7$—, i.e. —NR$^7$CO—, —NR$^7$SO$_2$—, —NR$^7$CONR$^8$—, —NR$^7$COO—, —NR$^7$CS—, —NR$^7$CSNR$^8$—, —NR$^7$CS—O— or —NR$^7$— may be prepared by the method described in the following (1A-1-a), (1A-1-b), (1A-1-c), (1A-1-d-1), (1A-1-d-2), (1A-1-e) or (1A-1-f.

(1A-1-a) In the compounds of the formula (IA-1), the compounds in which E is —NR$^7$CO—, that is the compounds of the formula (IA-1-A)

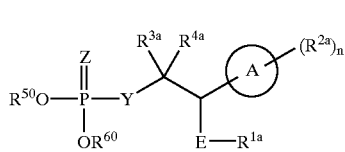

(IA-1-A)

wherein $E^1$ is —NR$^7$CO—, the other symbols are the same meaning as hereinbefore defined may be prepared by amidation of the compound of the formula (X-5)

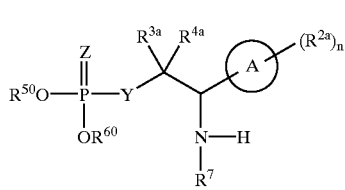

(X-5)

wherein all symbols are the same meaning as hereinbefore defined with the compound of the formula (X-6A)

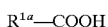

(X-6A)

wherein all symbols are the same meaning as hereinbefore defined.

The amidation is known per se and can be carried out by methods for example:
1) using an acid halide,
2) using a mixed acid anhydride,
3) using a condensing agent (EDC, DCC, etc.), etc.

These methods are explained as follows.
1) The method using an acid halide may be carried out, for example, by reacting a carboxylic acid with an acid halide (oxalyl chloride or thionyl chloride, etc.) in an inert organic solvent (chloroform, methylene chloride, diethyl ether or tetrahydrofuran, etc.) or without a solvent at from −20° C. to the reflux temperature of the solvent, and then by reacting the acid halide obtained with a corresponding amine in the presence of a tertiary amine (pyridine, triethylamine, dimethylaniline or dimethylaminopyridine, etc.) in an inert organic solvent (chloroform, methylene chloride, diethyl ether or tetrahydrofuran, etc.), at a temperature of from 0° C. to 40° C.

Besides, the reaction may be carried out in an organic solvent (dioxane, tetrahydrofuran, etc.), using aqueous solution of hydroxide or carbonate of alkali metal (an aqueous solution of sodium bicarbonate, an aqueous solution of sodium hydroxide, etc.) with acid halide at a temperature of from 0° C. to 40° C.

2) The method using a mixed acid anhydride may be carried out, for example, by reacting a carboxylic acid and an acid halide (pivaloyl chloride, tosyl chloride or mesyl chloride, etc.) or an acid derivative (ethyl chloroformate or isobutyl chloroformate, etc.) in the presence of a tertiary amine (pyridine, triethylamine, dimethylaniline or dimethylaminopyridine, etc.) in an inert organic solvent (chloroform, methylene chloride, diethyl ether or tetrahydrofuran, etc.) or without a solvent at a temperature of from 0° C. to 40° C., and then by reacting the mixture of acid anhydride obtained with a corresponding amine in an inert organic solvent (chloroform, methylene chloride, diethyl ether or tetrahydrofuran, etc.), at a temperature of from 0° C. to 40° C.

3) The method using a condensing agent may be carried out, for example, by reacting a carboxylic acid with a corresponding amine using a condensing agent (1,3-dicyclohexyl carbodiimide (DCC), 1-ethyl-3-[3-(dimethylamino)propyl]carbodiimide (EDC), 1,1′-carbonyldiimidazole (CDI) or 2-chloro-1-methylpyridinium iodide, etc.) in the presence or absence of a tertiary amine (pyridine, triethylamine, dimethylaniline or dimethylaminopyridine, etc.) in an inert organic solvent (chloroform, methylene chloride, dimethyl formamide, diethyl ether or tetrahydrofuran, etc.) or without a solvent, in the presence or absence of 1-hydroxybenztriazole (HOBt) at a temperature of from 0° C. to 40° C.

These reactions 1), 2) and 3) hereinbefore described may be preferably carried out in an atmosphere of inert gas (argon or nitrogen , etc.) under anhydrous conditions.

(1A-1-b) In the compounds of the formula (IA-1), the compounds in which E is —NR$^7$COO—, that is the compounds of the formula (IA-1-B)

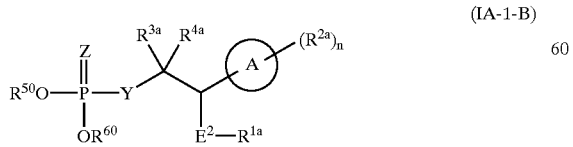

(IA-1-B)

wherein E$^2$ is —NR$^7$COO—, the other symbols are the same meaning as hereinbefore defined may be prepared by reaction for forming urethane of the compounds of the formula (X-5) with the compounds of the formula (X-6B)

$R^{1a}$—OCO—$X^1$ (X-6B)

wherein X$^1$ is a halogen atom, the other symbols are the same meaning as hereinbefore defined.

The reaction for forming urethane of the compounds of (X-5) with the compounds of the formula (X-6B) may be carried out as the same methods which above-mentioned 1) using an acid halide of amidation.

(1A-1-c) In the compounds of the formula (I), the compounds in which E is —NR$^7$SO$_2$—, that is the compounds of the formula (IA-1-C)

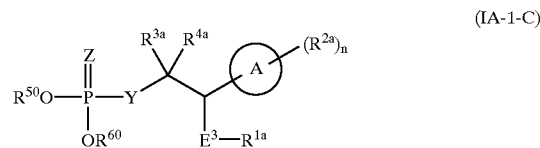

(IA-1-C)

wherein E$^3$ is —NR$^7$SO$_2$—, the other symbols are the same meaning as hereinbefore defined may be prepared by sulfonamidation of the compounds of the formula (X-5) hereinbefore described with the compounds of the formula (X-6C)

$R^{1a}$—SO$_2$Cl (X-6C)

wherein all symbols are the same meaning as hereinbefore defined.

The sulfonamidation is known per se and can be carried out, for example, using sulfonyl halide in the presence of a tertiary amine (pyridine, triethylamine, dimethylaniline or dimethylaminopyridine, etc.) in an inert organic solvent (chloroform, methylene chloride, diethyl ether or tetrahydrofuran, etc.) at a temperature of from 0° C. to 40° C.

(1A-1-d-1) In the compounds of the formula (I), the compounds in which E is —NR$^7$CONR$^8$— or —NR$^7$CSNR$^8$—, that is the compounds of the formula (IA-1-D-1)

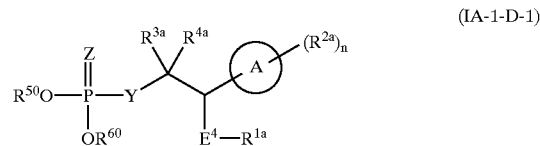

(IA-1-D-1)

wherein E$^4$ is —NR$^7$CONR$^8$— or —NR$^7$CSNR$^8$—, the other symbols are the same meaning as hereinbefore defined may be prepared by reacting the compounds of the formula (X-5) hereinbefore described with the compounds of the formula (X-6D-A)

$R^{1a}$—NHR$^8$ (X-6D-A)

wherein all symbols are the same meaning as hereinbefore defined and the compound of the formula (X-6D-B)

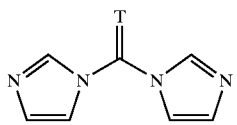
(X-6D-B)

wherein T is an oxygen atom or a sulfur atom.

The reaction using the compounds of the formulae (X-5), (X-6D-A) and (X(-6D-B) can be carried out by known method, for example, in an organic solvent (N,N-dimethylformamide, methylene chloride or tetrahydrofuran, etc.) in the presence or absence of an amine (triethylamine, pyridine, dimethylaniline or dimethylaminopyridine, etc.) at a temperature of from 0° C. to 80° C.

(1A-1-d-2) In the compounds of the formula (I), the compounds in which E is —NR$^7$CONR$^8$—, that is the compounds of the formula (IA-1-D-2)

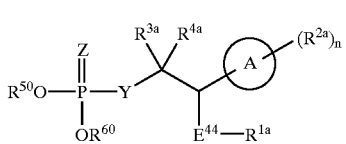
(IA-1-D-2)

wherein E$^{44}$ is —NR$^7$CONR$^8$—, the other symbols are the same meaning as hereinbefore defined may be prepared by reacting the compounds of the formula (X-5) hereinbefore described with the compounds of the formula (X-6D-C)

R$^{1a}$—N=C=O          (X-6D-C)

wherein all symbols are the same meaning as hereinbefore defined or the compounds of the formula (X-6D-D)

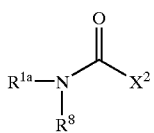
(X-6D-D)

wherein X$^2$ is a halogen atom, the other symbols are the same meaning as hereinbefore defined.

The reaction of the compounds of the formula (X-5) and (X-6D-C), or the reaction of the compounds of the formula (X-5) and (X-6D-D) are known per se, and can be carried out, for example, in an organic solvent (acetone, chloroform, methylene chloride, benxene or tetrahydrofuran, etc.) in the presence or absence of a tertiary amine (triethylamine, pyridine, dimethylaniline, dimethylaminopyridine, etc.) at a temperature of from 0° C. to 80° C., or as the same methods which above-mentioned 1) using an acid halide of amidation.

(1A-1-e) In the compounds of the formula (I), the compounds in which E is —NR$^7$—, that is the compounds of the formula (IA-1-E)

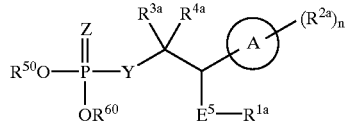
(IA-1-E)

wherein E$^5$ is —NR$^7$—, the other symbols are the same meaning as hereinbefore defined may be prepared by reacting the compounds of the formula (X-5) hereinbefore described with the compounds of the formula (X-6E)

X$^3$—R$^{1a}$          (X-6E)

wherein X$^3$ is a halogen atom or hydroxy, the other symbols are the same meaning as hereinbefore defined.

The reaction of the compounds of the formula (X-5) with the compounds of the formula (X-6E) is N-alkylation or corresponding one. For example, when X$^3$ is a halogen atom, then the reaction may be carded out in an organic solvent (N,N-dimethylformamide or tetrahydrofuran, etc.) in the presence of a base (sodium hydride, butyl lithium, lithium diisopropylamide, etc.) at a temperature of from 0° C. to 80° C. And when X$^3$ is hydroxy, then the reaction may be carried out in an organic solvent (methylene chloride, diethyl ether, tetrahydrofuran, acetone, benzene, toluene, etc.) in the presence of an azo compound (diethyl azodicarboxylate, diisopropyl azodicarboxylate, 1,1'-(azodicarbonyl)dipiperidine, 1,1'-azobis(N,N-dimethylformamide), etc.) and a phosphine compound (triphenylphosphine, tributylphosphine, trimethylphosphine, etc.) at a temperature of from 0° C. to 60° C.

(1A-1-f) In the compounds of the formula (I), the compounds in which E is —NR$^7$CS—, —NR$^7$CS—O— or —NR$^7$CSNR$^8$—, that is the compounds of the formula (IA-1-F)

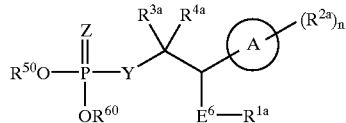
(IA-1-F)

wherein E$^6$ is —NR$^7$CS—, —NR$^7$CS—O— or —NR$^7$CSNR$^8$—, the other symbols are the same meaning as hereinbefore defined may be prepared by reacting the compounds of the formula (IA-1-A), (IA-1-B) or (IA-1-D-2) hereinbefore described, that is the compounds of the formula (IA-1-FF)

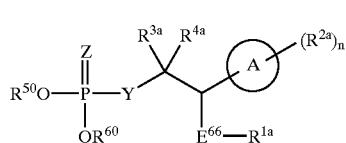
(IA-1-FF)

wherein $E^{66}$ is —$NR^7CO$—, —$NR^7COO$— or —$NR^7CONR^8$—, the other symbols are the ame meaning as hereinbefore defined
with Lawesson's Reagent of the formula (X-6F)

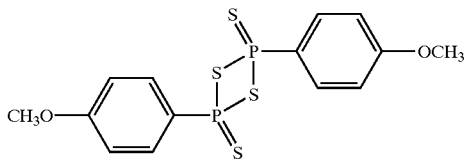

(X-6F)

The reaction using Lawesson's Reagent is known per se, and can be carried out in an organic solvent (dioxane, benzene, toluene or xylene, etc.), using Lawesson's reagent at a temperature of from 20° C. to 150° C. This reaction may be preferably carried out in an atmosphere of inert gas (argon or nitrogen, etc.) under anhydrous conditions.

(2) In the compounds of the formula (I), the compounds in which at least one of $R^1$, $R^2$, $R^3$ or $R^4$ represent contains carboxyl, hydroxy or amino, that is the compound of the formula (IB)

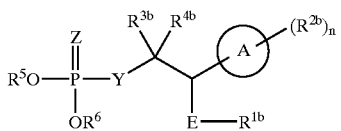

(IB)

wherein $R^{1b}$, $R^{2b}$, $R^{3b}$ or $R^{4b}$ is the same meaning as $R^1$, $R^2$, $R^3$ or $R^4$, respectively, provided that, at least one of them is a group containing carboxyl, hydroxy or amino may be prepared by the method described in the following (2-1), (2-2) or (2-3).

(2-1) In the compounds of the formula (IB), the compounds in which all of $R^5$ and $R^6$ is hydrogen atom, that is the compounds of the formula (IB-1)

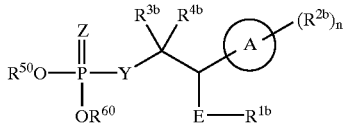

(IB-1)

wherein all symbols are the same meaning as hereinbefore defined may be prepared by subjecting to a deprotection reaction a compound, among the compound of the formula (IA-1), which contains at least one protected carboxyl, hydroxy or amino, i.e. the compound of the formula (IA-1-Y)

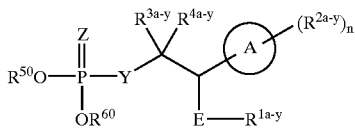

(IA-1-Y)

wherein $R^{1a-y}$, $R^{2a-y}$, $R^{3a-y}$ and $R^{4a-y}$ is the same meaning as $R^{1a}$, $R^{2a}$, $R^{3a}$ and $R^{4a}$, provided that, at least one of them represent contains protected carboxyl, hydroxy or amino, the other symbols are the same meaning as hereinbefore defined.

Each deprotection reaction of protective group for phosphoric acid, carboxyl, hydroxy or amino is known well and means a comprehensive deprotection reaction easily understood by those skilled in the art, for example, alkali hydrolysis, deprotection reaction under acidic condition, deprotection reaction by hydrogenation or deprotection reaction of a group containing silyl. The desired compounds of the present invention can be easily prepared by these reactions.

Each deprotection reaction of protective group for phosphoric acid, carboxyl, hydroxy or amino are explained.

As should be easily understood by those skilled in the art, for example, methyl, ethyl, t-butyl and benzyl are included in the protective groups for carboxyl, but other groups that can be easily and selectively eliminated may also be used instead. For example, the groups described in T. W. Greene, Protective Groups in Organic Synthesis, Wiley, New York, 1991 may be used.

For example, methoxymethyl, tetrahydropyranyl, t-butyldimethylsilyl, acetyl and benzyl are included in the protective groups for hydroxy, but other groups that can be easily and selectively eliminated may also be used instead. For example, the groups described in T. W. Greene, Protective Groups in Organic Synthesis, Wiley, New York, 1991 may be used.

For example, benzyloxycarbonyl, t-butoxycarbonyl and trifluoroacetyl are included in the protective groups for amino but other groups that can be easily and selectively eliminated may also be used instead. For example, the groups described in T. W. Greene, Protective Groups in Organic Synthesis, Wiley, New York, 1991 may be used.

Deprotection reaction by alkali hydrolysis is known, for example, it is carried out in an organic solvent (methanol, tetrahydrofuran, dioxane, etc.) using hydroxide of alkali metal (sodium hydroxide, potassium hydroxide, lithium hydroxide, etc.), hydroxide of alkaline earth metal (barium hydroxide, calcium hydroxide, etc.) or carbonate (sodium carbonate, potassium carbonate, etc.) or an aqueous solution thereof or a mixture thereof at a temperature of from 0° C. to 40° C.

Deprotection reaction under acidic conditions is known, for example, it is carried out in an organic solvent (methylene chloride, chloroform, dioxane, ethyl acetate, anisole, etc.), in organic acid (acetic acid, trifluoroacetic acid, methanesulfonic acid, trimethylsilyl iodide etc.) or inorganic acid (hydrochloric acid, sulfuric acid, etc.) or a mixture thereof (hydrobromic acid-acetic acid etc.) at a temperature of from 0° C. to 100° C.

Deprotection reaction by hydrogenation is known, for example, it is carried out in an inert solvent [ether (e.g. tetrahydrofuran, dioxane, dimethoxyethane, diethyl ether, etc.), alcohol (e.g. methanol, ethanol, etc.), benzene (e.g. benzene, toluene, etc.), ketone (e.g. acetone, methylethylketone, etc.), nitrile (e.g. acetonitrile etc.), amide (e.g. dimethylformamide etc.), water, ethyl acetate, acetic acid or a mixture of two or more thereof], in the presence of hydrogenating catalyst (e.g. palladium-carbon, palladium black, palladium hydroxide, platinum dioxide, Raney-nickel, etc.) under normal atmosphere or suppressed atmosphere of hydrogen or in the presence of ammonium formate, at a temperature of from 0° C. to 200° C.

Deprotection reaction of silyl group is known, for example, it is carried out in a water-soluble organic solvent (tetrahydrofuran, acetonitrile, etc.), using tetrabutylammonium fluoride at a temperature of from 0° C. to 40° C.

(2-2) In the compounds of the formula (IB), the compound in which all of $R^5$ and $R^6$ are hydrogen atom, that is the compound of the formula (IB-2)

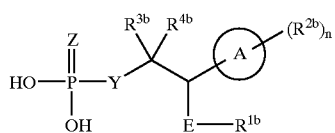
(IB-2)

wherein all symbols are the same meaning as hereinbefore defined may be prepared by subjecting to a deprotection reaction a compound, among the compound of the formula (IA-2) hereinbefore described, which contains at least one protected carboxyl, hydroxy or amino, i.e. the compound of the formula (IA-2-Y)

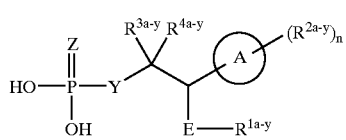
(IA-2-Y)

all symbols are the same meaning as hereinbefore defined.

The deprotection reaction is carried out as the same method hereinbefore described.

(2-3) In the compounds of the formula (IB), the compounds in which one of $R^5$ and $R^6$ is a hydrogen atom, and the other is not a hydrogen atom, that is the compounds of the formula (IB-3)

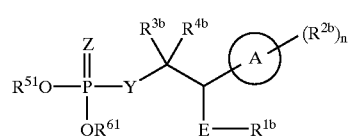
(IB-3)

wherein all symbols are the same meaning as hereinbefore defined may be prepared by subjecting to a deprotection reaction a compound, among the compound of the formula (IA-3) hereinbefore described, which contains at least one protected carboxyl, hydroxy or amino, i.e. the compound of the formula (IA-3-Y)

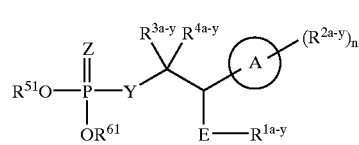
(IA-3-Y)

all symbols are the same meaning as hereinbefore defined.

The deprotection reaction is carried out as the same method hereinbefore described.

The compounds of the formula (X-5) may be prepared by the method described in the following reaction scheme 2.

In the scheme, $X^4$ is a halogen atom or hydroxy, Q is a protective group for amino, the other symbols are the same meaning as hereinbefore defined.

Reaction Scheme 2

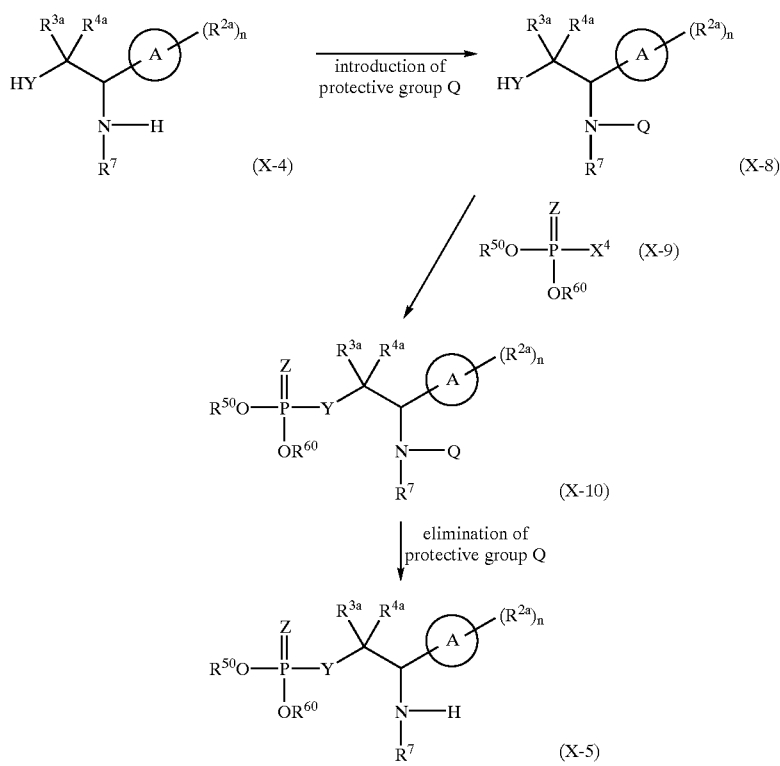

In the reaction scheme 2, the compounds in which $R^{2a}$ does not contain —S— or —S(O)—, among the compound of the formula (X-10), that is the compounds of the formula (X-10-A)

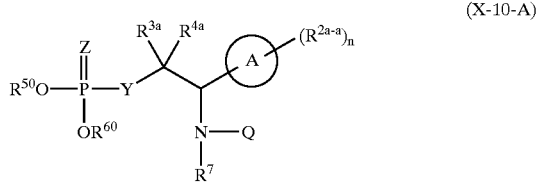

(X-10-A)

wherein $R^{2a-a}$ is the same meaning as $R^{2a}$, provided that its does not contain —S— or —S(O)—, the other symbols are the same meaning as hereinbefore defined.

In the scheme, all symbols are the same meaning as hereinbefore defined.

Reaction Scheme 3

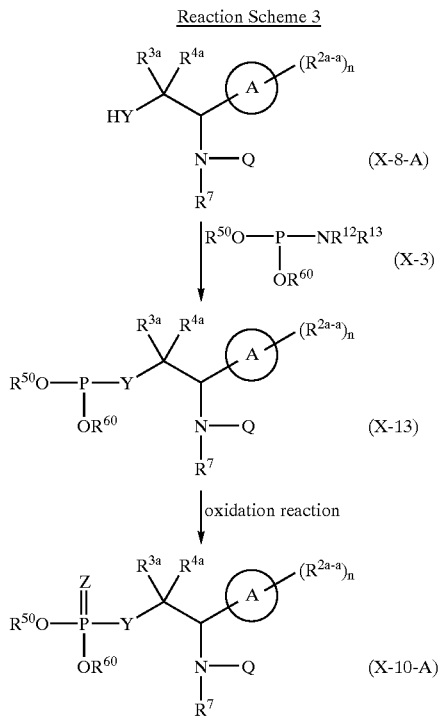

In each reaction described in the present specification, reaction products may be purified by conventional techniques. For example, purification may be carried out by distillation at atmospheric or reduced pressure, by high performance liquid chromatography, thin layer chromatography or column chromatography using silica gel or magnesium silicate, by washing or by recrystallization, etc. Purification may be carried out after each reaction, or after a series of reactions.

The starting materials and agents in the present invention are known per se (commercially available), or may be prepared by conventional method.

For example, in the compound of the formula (X-8), 2-amino-2-phenylethanol ((R)-(−)-2-phenyl glycinol, (S)-(+)-2-phenyl glycinol) is known as CAS No. 56613-80-0 (R form) and 20989-17-7(S form), and (1R,2S)-(+)-cis-1-amino-2-indanol and (1S,2R)-(−)-cis-1-amino-2-indanol are known as CAS No. 136030-00-7 and 126456-43-7, respectively.

Besides, 2-amino-2-phenyl-1,1-propanoethanol may be prepared according to the method described in the literature (Larry R. Kpepski et al., SYNTHESIS, 301,(1986)) from cyclobutanone as a starting material.

(1S,2R)-1-methyl-2-phenylethanol, (1R,2S)-1-methyl-2-phenylethanol, (1R,2R)-1-methyl-2-phenylethanol, and (1S, 2S)-1-methyl-2-phenylethanol may be prepared according to the method described in the literatures ( K. Barry Sharpless et al., Tetrahedron Lett. 37(19), 3219(1996), von Vladimir Prelog et.al., Helvetica Chimca Acta 66(7), 2274, (1983), Christian R. Noe et.al., Monatsh Chem., 122(4), 283(1991)).

Pharmacological Activities

Because of having a TNFα production inhibitory effect, the compounds represented by general formula (I) are useful as preventives and/or remedies of various diseases induced by inflammatory cytokines including TNFα (example for rheumatoid arthritis, ulcerative colitis, Crohn's disease, hepatitis, sepsis, hemorrhagic shock, multiple sclerosis, cerebral infarction, diabetes, interstitial pneumonia, uveitis, pain, glomerulonephritis, HIV-associated diseases, cachexia, myocardial infarction, chronic heart failure, oral aphtha, Hansen's disease, infection, etc.). It has been confirmed that the compounds of the present invention of the formula (I) possess a TNFα production inhibitory effect by the following experimental results.

(i) Measure of TNFα Production Inhibitory Activity

Measure of TNFα production inhibitory activity was prepared according to procedures described previously (Kazuo Ohuchi, SEIBUTSUKAGAKUJIKKENKOZA, 12, 707 (1994) Hirokawa, Tokyo). Female mice (BALB/c, 7 weeks) were injected with test compounds via intravenous administration and with LPS (100 μg/mouse) (Bacto W. E. coli 055:B5; DIFCO Lab.) via in traperitoneal administration. At 90 minutes after LPS challenge, blood with heparin was obtained from abdominal aorta, and serum was stored at −80° C. Serum level of TNFα was determined by mouse cytokine ELISA kit (Genzyme). Inhibition and 50% effective dose ($ED_{50}$) of test compounds were calculated as 100% of the difference of serum level of TNFα between in control and in LPS. $ED_{50}$ of some compounds produced by the following examples were 0.01–100 mg/kg. For examples, $ED_{50}$ of (2R)-2-phenyl-2-(N-octanoylamino) ethylphosphate.2Na (the compound of example 8) was 2.6 mg/kg.

Toxicity

The toxicity of the compounds of the present invention is very low and therefore the compounds may be considered safe for pharmaceutical use.

Application for Pharmaceuticals

Because of having a TNFα production inhibitory effect, the compounds represented by general formula (I) are useful as preventives and/or remedies for rheumatoid arthritis, ulcerative colits, Crohn's disease, hepatitis, sepsis, hemorrhagic shock, multiple sclerosis, cerebral infarction, diabetes, interstitial pneumonia, uveitis, pain, glomerulonephritis, HIV-associated diseases, cachexia, myocardial infarction, chronic heart failure, oral aphtha, Hansen's disease, infection, etc.

For the purpose above described, the compounds of formula (I) of the present invention and non-toxic salts thereof, acid addition salts thereof and hydrates thereof may normally be administered systemically or locally, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 1000 mg, by oral administration, up to several times per day, and between 0.1 mg and 100 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

The compounds of the present invention may be administered as inner solid compositions or inner liquid compositions for oral administration, or as injections, liniments or suppositories etc. for parenteral administration.

Inner solid compositions for oral administration include compressed tablets, pills, capsules, dispersible powders and granules etc. Capsules contain hard capsules and soft capsules.

In such inner solid compositions, one or more of the active compound(s) is or are, admixed with at least one inert diluent (lactose, mannitol, glucose, microcrystalline cellulose, starch etc.), connecting agents (hydroxypropyl cellulose, polyvinylpyrrolidone, magnesium metasilicate aluminate etc.), disintegrating agents (cellulose calcium glycolate etc.), lubricating agents (magnesium stearate etc.), stabilizing agents, assisting agents for dissolving (glutamic acid, asparaginic acid etc.) etc. to prepare pharmaceuticals by known methods. The pharmaceuticals may, if desired, be coated with material such as sugar, gelatin, hydroxypropyl cellulose or hydroxypropyl cellulose phthalate etc., or be coated with two or more films. And further, coating may include containment within capsules of absorbable materials such as gelatin.

Inner liquid compositions for oral administration include pharmaceutically-acceptable water-agents, suspensions, emulsions, syrups and elixirs etc. In such liquid compositions, one or more of the active compound(s) is or are comprised in inert diluent(s) commonly used in the art (purified water, ethanol or mixture thereof etc.). Besides inert diluents, such compositions may also comprise adjuvants such as wetting agents, suspending agents, emulsifying agents, sweetening agents, flavouring agents, perfuming agents, preserving agents and buffer agents etc.

Injections for parenteral administration include solutions, suspensions and emulsions and solid injections which are dissolved or suspended in solvent when it is used. One or more active compound(s) is or are dissolved, suspended or emulsified in a solvent when such compositions are used. Aqueous solutions or suspensions include distilled water for injection and physiological salt solution, plant oil, propylene glycol, polyethylene glycol and alcohol such as ethanol etc., and mixture thereof. Such compositions may comprise additional diluents such as stabilizing agent, assisting agents for dissolving (glutamic acid, asparaginic acid, POLYSOL-BATE80 (registered trade mark) etc.), suspending agents, emulsifying agents, dispersing agents, buffer agents, preserving agents etc. They may be sterilized for example, by filtration through a bacteria-retaining filter, by incorporation of sterilizing agents in the compositions or by irradiation. They may also be manufactured in the form of sterile solid compositions and which can be dissolved in sterile water or some other sterile diluent for injection immediately before use.

Other compositions for parenteral administration include liquids for external use, ointments, endermic liniments, aerosols, spray compositions, suppositories and pessaries for vaginal administration etc. which comprise one or more of the active compound(s) and may be prepared by known methods.

Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. No. 2,868,691 or 3,095,355 may be used.

BEST MODE FOR CARRYING OUT THE INVENTION

REFERENCE EXAMPLE AND EXAMPLE

The following reference examples and examples illustrate the present invention, but do not limit the present invention.

The solvents in the parentheses show the developing or eluting solvents and the ratios of the solvents used are by volume in chromatographic separations or TLC.

Reference Example 1

(2R)-2-t-Butoxycarbonylamino-2-phenylethanol

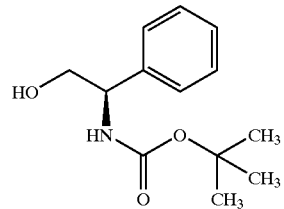

To a solution of (2R)-2-amino-2-phenylethanol (5.0 g) in chloroform (50 ml) was added di-t-butyl-dicarbonate (9.55 g), the mixture was stirred for 1 hour at room temperature. The solvent was evaprated and the obtained solid was washed with a mixture of hexane-diethyl ether to give the title compound (8.43 g) having the following physical data.

TLC: Rf 0.35 (Ethyl acetate:Hexane=1:1).

Example 1

Diphenyl-(2R)-2-t-butoxycarbonylamino-2-phenylethylphosphate

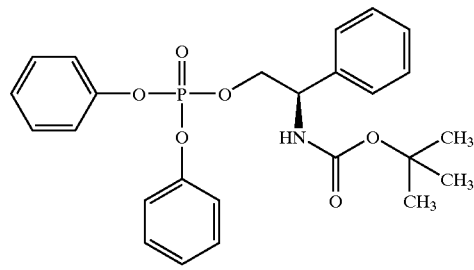

To a solution of the compound prepared in reference example 1 (3.04 g) in pyridine (20 ml) was added dropwise a solution of diphenylphosphoryl chloride (4.12 g) in pyridine (20 ml) under cooling with ice, and the mixture was stirred for 30 minutes at 0° C. The reaction mixture was poured into 1N hydrochloric acid under cooling with ice and then extracted with ethyl acetate. The organic layer was washed with water and a saturated aqueous solution of sodium chloride, successively, dried over anhydrous magnesium sulfate and concentrated. The obtained solid was washed with a mixture of hexane ethyl acetate (hexane:ethyl acetate=3:1) to give the compound (4.47 g) of the present invention having the following physical data.

TLC: Rf 0.70(Hexane:Ethyl acetate=1:1);

NMR(CDCl$_3$): δ7.40–7.05(m, 15H), 5.40–5.15(br, 1H), 5.08–4.85(br, 1H), 4.54–4.32(m, 2H), 1.41(s, 9H).

Reference Example 2

Diphenyl-(2R)-2-amino-2-phenylethylphosphate Trifluoroacetate

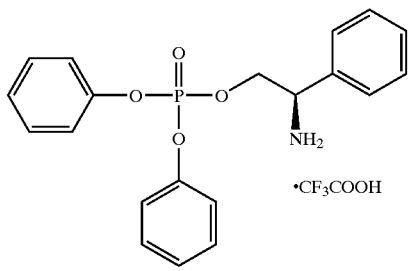

To a solution of the compound prepared in example 1 (1.1 g) in methylene chloride (10 ml) was added anisole (2 ml) and trifluoroactic acid (5 ml) and the mixture was stirred for 1 hour at room temperature. The excess trifluoroacetic acid was removed as the toluene azeotrope and the residue was dried under reduced pressure to give the crude product of the title compound. The obtained crude product was used the next reaction without further purification.

Example 2

Diphenyl-(2R)-2-N-octanoylamino-2-phenylethylphosphate

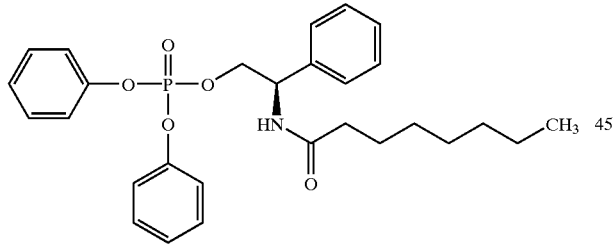

To a solution of the crude product prepared in reference example 2 in methylene chloride (5 ml) was added dropwise a solution of octanoyl chloride (707 mg) in methylene chloride (5 ml) under cooling with ice. Pyridine (0.76 ml) was added and the mixture was stirred for 30 minutes at 0° C. To the reaction mixture was added methanol (2 ml) and then the mixture was poured into 1N hydrochloric acid and extracted with ethyl acetate. The organic layer was washed with water and a saturated aqueous solution of sodium chloride, successively, dried over anhydrous magnesium sulfate and concentrated to give the crude product of the present invention having the following physical data. The obtained crude product was used the next reaction without further purification.

TLC: Rf 0.50 (Hexane:Ethyl acetate=1:1).

Example 3

Phenyl-(2R)-2-octanoylamino-2-phenylethylphosphate

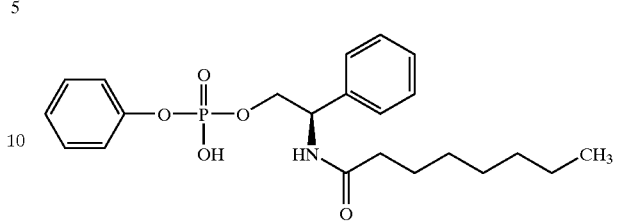

To a solution of the crude product prepared in example 2 in acetic acid (10 ml) was added platinum oxide hydrate (1.26 g) under an atmosphere of argon, and the atmosphere was replaced with hydrogen. The reaction mixture was stirred for 3 hours under an atmosphere of hydrogen. The reaction mixture was filtered and the filtrate was concentarated. The residue was purified by column chromatography on silica gel (chloroform:methanol:water=10:1:0→65:25:4) to give the title compound (129 mg) having the following physical data.

TLC: Rf 0.38(Chloroform:Methanol:Water=65:25:4);

NMR(CD$_3$OD): δ7.40–6.98(m, 10H), 5.15(t, J=7 Hz, 1H), 4.23–3.95(m, 2H), 2.21(t, J=7.5 Hz, 2H), 1.68–1.45(m, 2H), 1.27(s, 8H), 0.88(t, J=6.5 Hz, 3H).

Example 4

(2R)-2-octanoylamino-2-cyclohexylethylphosphate

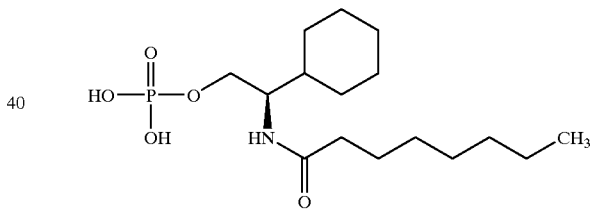

To a solution of the crude product prepared in example 2 in acetic acid (5 ml) was added platinum oxide hydrate (250 mg) under an atmosphere of argon, and the atmosphere was replaced with hydrogen. The reaction mixture was stirred for 2 days under an atmosphere of hydrogen. The catalyst was filtered off and the mother liquid was concentrated. The residue was purified by column chromatography on silica gel (chloroform:methanol:water=65:35:8). To the obtained compound was added 1N hydrochloric acid and then the mixture was extracted with ethyl acetate. The organic layer was washed with water and a saturated aqueous solution of sodium chloride, successively, dried over anhydrous magnesium sulfate and concentrated. The obtained oil was solidified with diethyl ether and dried under reduced pressure to give the compound (35 mg) of the present invention having the following physical data.

TLC: Rf 0.47(n-Butanol:Acetic acid:Water=4:1:1);

NMR(CDCl$_3$+CD$_3$OD): δ4.04–3.94(m, 2H), 3.90–3.78 (m, 1H), 2.21(t, J=7.5 Hz, 2H), 1.83–1.43(m, 8H), 1.38–0.95 (m)and 0.88(t, J=6.5 Hz)total 16H.

Example 5

Bis(2,2,2-trichloroethyl)-(2R)-2-t-butoxycarbonylamino-2-phenylethylphosphate

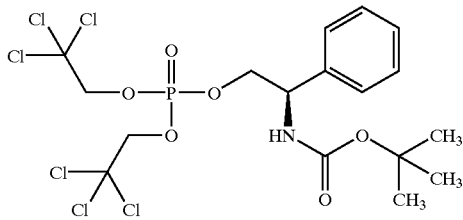

To a solution of the compound prepared in reference example 1 (3.64 g) in pyridine (30 ml) was added a solution of bis(2,2,2-trichloroethyl)phosphoryl chloride (6.99 g) in pyridine (10 ml) under cooling with ice, and the mixture was stirred for 15 miniutes at 0° C. The mixture was diluted with ethyl acetate. The organic layer was washed with 1N hydrochloric acid, water and a saturated aqueous solution of sodium chloride, successively, dried over anhydrous magnesium sulfate and concentrated. The residue was purified by column chromatography on silica gel (hexane:ethyl acetate=4:1) to give the compound (6.66 g) of the present invention having the following physical data.

TLC: Rf 0.85(Ethyl acetate:Hexane=1:1);

NMR(CD$_3$OD): δ7.40–7.25(m, 5H), 5.06–4.94(m, 1H), 4.68–4.56(m, 4H), 4.48–4.26(m, 2H), 1.44(s, 9H).

Example 6

Bis(2,2,2-trichloroethyl)-(2R)-2-octanoylamino-2-phenylethylphosphate

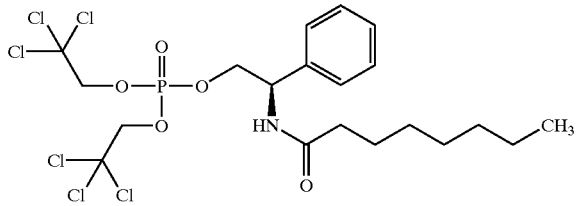

The crude product of the present invention having the following physical data was obtained by the same procedure as a series of reactions of Reference example 2→Example 2 using the compound prepared in Example 5. The obtained crude product was used the next reaction without further purification.

TLC: Rf 0.70(Ethyl acetate:Hexane=1:1).

Example 7

(2R)-2-Octanoylamino-2-phenylethylphosphate

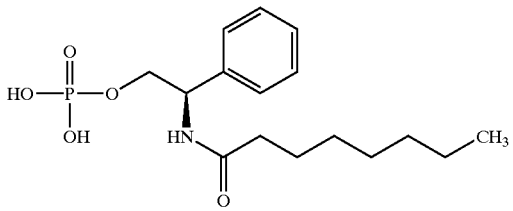

To a solution of the crude product prepared in example 6 in acetic acid (5 ml) was added zinc powder (1.7 g) and the mixture was stirred for 16 hours at room temperature. The reaction mixture was filtered. The residue was washed with acetic acid and the mother liquid was combined with the above-mentioned filtrate. The solvent was removed as the toluene azeotrope. To the obtained oil was added 1N hydrochloric acid and ethyl acetate, and then extracted. The organic layer was washed with 1N hydrochloric acid, water and a saturated aqueous solution of sodium chloride, successively, dried over anhydrous magnesium sulfate and concentrated. The residue was purified by column chromatography on silica gel (chloroform:methanol:water=10:1:0= 65:25:1→65:25:2). Further the obtained compound was purified by column chromatography on silica gel (chloroform:methanol:water=30:1:0→10:1:0.1→65:25:4). To the obtained white powder was added 1N hydrochloric acid and ethyl acetate and then extracted. The organic layer was washed with water and a saturated aqueous solution of sodium chloride, successively, dried over anhydrous magnesium sulfate and concentrated. The residue was lyophilized from a mixture of water-dioxane to give the compound (260 mg) of the present invention having the following physical data.

TLC: Rf 0.31(Chloroform:Methanol:Water=65:25:4);

NMR(CD$_3$OD): δ7.40–7.20(m, 5H), 5.18(dd, J=7.4, 5.6 Hz, 1H), 4.20–4.05(m, 2H), 2.26(t, J=7 Hz, 2H), 1.80–1.50 (m, 2H), 1.40–1.10(m, 8H), 0.89(t, J=7 Hz, 3H).

Example 7(1)~Example 7(4)

The compounds of the present invention having the following physical data were obtained by the same procedure as a series of reactions of Reference example 1→Example 5→Reference example 2→Example 2→Example 7, using corresponding aminoalcohol derivatives instead of (2R)-2-amino-2-phenylethanol.

Example 7(1)

(2S)-2-Octanoylamino-2-phenylethylphosphate

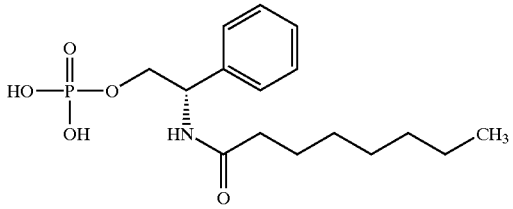

TLC: Rf 0.33(Chloroform:Methanol:Water=65:25:4);

NMR(CD$_3$OD): δ7.40–7.20(m, 5H), 5.19(dd, J=7.5, 5.7 Hz, 1H), 4.20–4.05(m, 2H), 2.26(t, J=7.5 Hz, 2H), 1.61 (quint, J=7.5 Hz, 2H), 1.40–1.20(m, 8H), 0.89(t, J=6.6 Hz, 3H).

Example 7(2)

1-Methyl-2-nonanoylamino-2-phenylethylphosphate

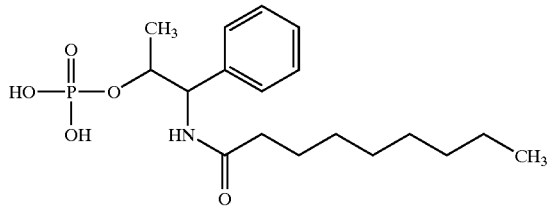

TLC: Rf 0.38(Chloroform:Methanol:Water=65:25:4);

NMR(CD$_3$OD): δ7.40–7.20(m, 5H), 5.40–4.98(m, 1H), 4.72–4.62(m, 1H), 2.26(t, J=7.2 Hz, 2H), 1.66–1.54(m, 2H), 1.38–1.20(m)and 1.21(d, J=6.3 Hz)total 13H, 0.89(t, J=7.2 Hz, 3H).

Example 7(3)

1-Methyl-2-octanoylamino-2-phenylethylphosphate

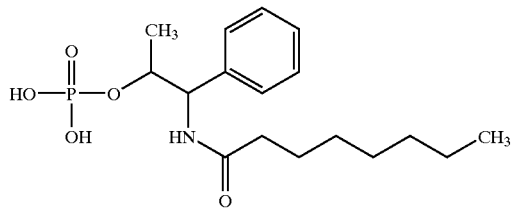

TLC: Rf 0.42(Chloroform:Methanol:Water=65:25:4);

NMR(CD$_3$OD): δ7.40–7.20(m, 5H), 5.03(d, J=4.4 Hz, 1H), 4.80–4.50(m, 1H), 2.27(t, J=7 Hz, 2H), 1.70–1.50(m, 2H), 1.40–1.18(m)and 1.21(d, J=6.2 Hz)total 11H, 0.88(t, J=6.6 Hz, 3H).

Example 7(4)

2-Octanoylamino-2-phenyl-1,1-propanoethylphosphate

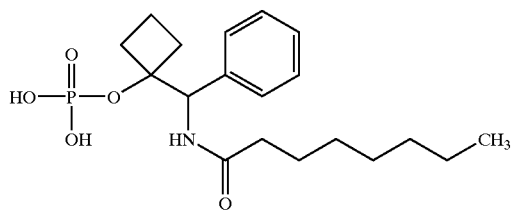

TLC: Rf 0.44(Chloroform:Methanol:Water=65:25:4);

NMR(CD$_3$OD): δ7.45–7.38(m, 2H), 7.35–7.20(m, 3H), 5.15(d, J=2.4 Hz, 1H), 2.88(q, J=12 Hz, 1H), 2.45(q, J=12 Hz, 1H), 2.32–2.14(m)and 2.27(t, J=6 Hz)total 4H, 1.94–1.80(m, 1H), 1.78–1.52(m, 3H), 1.40–1.16(m, 8H), 0.88(t, J=6.6 Hz, 3H).

Example 8

(2R)-2-Octanoylamino-2-phenylethylphosphate Disodium Salt

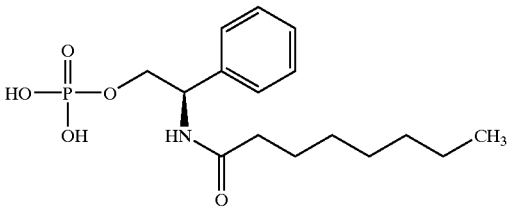

To a solution of the compound prepared in example 7 (784 mg) in ethanol (50 ml) was added 1N aqueous solution of sodium hydroxide and the mixture was stirred for 10 minutes at room temperature, and then concentrated. To the reaction mixture was added ethanol and then the mixture was concentrated (twice). The residue was solidified with diethyl ether to give the compound (780 mg) of the present invention having the following physical data.

TLC: Rf 0.37(Chloroform:Methanol:Water=65:25:4);

NMR(CD$_3$OD): δ7.34(d, J=7.0 Hz, 2H), 7.26(t, J=7.0 Hz, 2H), 7.17(t, J=7.0 Hz, 1H), 4.95–4.80(m, 1H), 4.04–3.56(m, 2H), 2.40–2.18(m, 2H), 1.70–1.50(m, 2H), 1.40–1.20(m, 8H), 0.89(t, J=6.3 Hz, 3H).

Example 8(1)–Example 8(2)

The compounds of the present invention having the following physical data were obtained by the same procedure as Example 8, using the compounds prepared in Example 7(3) or Example 7(1)

Example 8(1)

1-Methyl-2-octanoylamino-2-phenylethylphosphate Disodium Salt

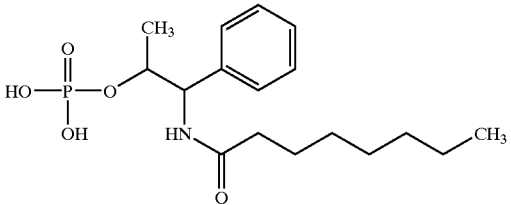

TLC: Rf 0.43(Chloroform:Methanol:Water=65:25:4);

NMR(CD$_3$OD): δ7.45–7.40(m, 2H), 7.25–7.10(m, 3H), 4.63–4.58(m, 2H), 2.34–2.18(m, 2H), 1.60–1.50(m, 2H), 1.38–1.10(m, 8H), 1.03(d, J=6.3 Hz, 3H), 0.87(t, J=6.6 Hz, 3H).

Example 8(2)

(2S)-2-Octanoylamino-2-phenylethylphosphate Disodium Salt

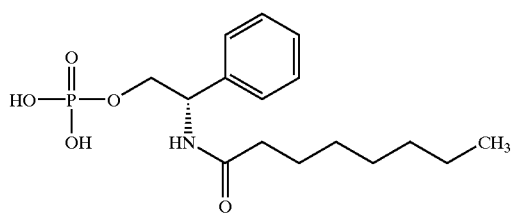

TLC: Rf 0.40(Chloroform:Methanol:Water=65:25:4);

NMR(CD$_3$OD): δ7.36–7.31(m, 2H), 7.30–7.24(m, 2H), 7.22–7.13(m, 1H), 4.93–4.80(m, 1H), 4.05–3.85(m, 2H), 2.38–2.18(m, 2H), 1.66–1.52(m, 2H), 1.40–1.20(m, 8H), 0.89(brt, J=6.6 Hz, 3H).

Example 9(1)–Example 9(4)

The compounds of the present invention having the following physical data were obtained by the same procedure as a series of reactions of Reference example 1→Example 5→Reference example 2→Example 2→Example 7→Example 8, using corresponding aminoalcohol derivatives instead of (2R)-2-phenylethanol.

Example 9(1)

(1S,2R)-1-Methyl-2-octanoylamino-2-phenylethylphosphate Disodium Salt

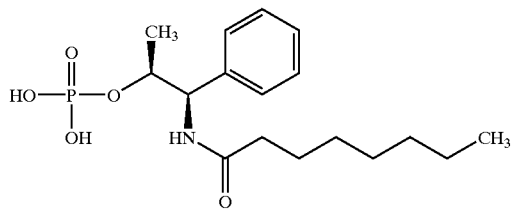

TLC: Rf 0.20(Chloroform:Methanol:Water=65:25:4);

NMR(CD$_3$OD): δ7.44(brd, J=6.6 Hz, 2H), 7.26–7.10(m, 3H), 4.60(m, 2H), 2.35–2.18(m, 2H), 1.54(m, 2H), 1.25(m, 8H), 1.04(d, J=6 Hz, 3H), 0.84(t, J=6.3 Hz, 3H).

Example 9(2)

(1R,2S)-1-Methyl-2-octanoylamino-2-phenylethylphosphate Disodium Salt

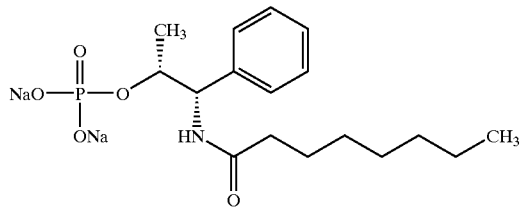

TLC: Rf 0.23(Chloroform:Methanol:Water=65:25:4);

NMR(CD$_3$OD): δ7.44(d, J=6.9 Hz, 2H), 7.28–7.12(m, 3H), 4.61 (m, 2H), 2.35–2.18(m, 2H), 1.55(m, 2H), 1.25(m, 8H), 1.04(d, J=6.3 Hz, 3H), 0.87(t, J=6.3 Hz, 3H).

Example 9(3)

(1R,2R)-1-Methyl-2-octanoylamino-2-phenylethylphosphate Disodium Salt

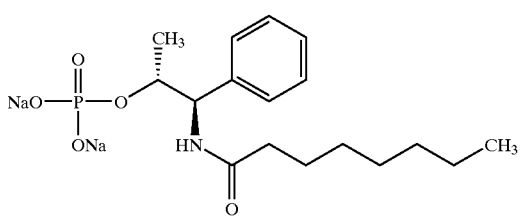

TLC: Rf 0.24(Chloroform:Methanol:Water=65:25:4);

NMR(CD$_3$OD): δ7.35(brd, J=7.2 Hz, 2H), 7.26(brt, J=7.2 Hz, 2H), 7.18(m, 1H), 4.40–4.24(m, 2H), 2.38–2.10(m, 2H), 1.55(m, 2H), 1.35–1.10(m, 8H), 1.05(d, J=5.7 Hz, 3H), 0.87(t, J=6.6 Hz, 3H).

Example 9(4)

(1S,2S)-1-Methyl-2-octanoylamino-2-phenylethylphosphate Disodium Salt

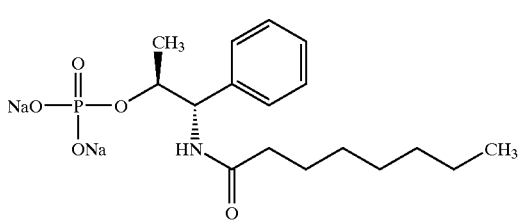

TLC: Rf 0.43(Chloroform:Methanol:Water=65:35:8);

NMR(CD$_3$OD): δ7.40–7.30(m, 2H), 7.30–7.15(m, 3H), 4.41–4.25(m, 2H), 2.38–2.15(m, 2H), 1.63–1.45(m, 2H), 1.38–1.12(m, 8H), 1.06(d, J=6.0 Hz, 3H), 0.87(t, J=6.8 Hz, 3H).

Example 10

Dibenzyl-(1R,2R)-1-octanoylaminoindan-2-ylphosphate

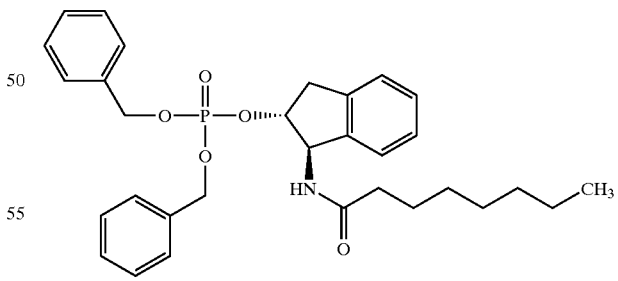

(1R,2S)-1-(N-octanoylamino)indan-2-ol (1.10 g), which is obtained by the same procedure as a series of reactions of example 2, using (1R,2S)-1-aminoindan-2-ol, triphenylphosphine (1.26 g) and dibenzyl phosphate (1.33 g) were dissolved in tetrahydrofuran (12 ml) and the mixture was cooled at 0° C. To the mixure was added dropwise diethyl azodicarboxylate (40% solution in toluene) and the mixture was stirred for 24 hours at room temperature. The reaction mixture was concentrated and the residue was purified by column chromatography on silica gel (hexane:ethyl acetate=3:1→2:1). Further the obtained compound was purified by column chromatography on silica gel (hexane:ethyl acetate=5:1→4:1) to give the compound (260 mg) of the present invention having the following physical data.

TLC: Rf 0.55(Methylene chloride:Methanol=19:1);

NMR(CDCl₃): δ7.40–7.15(m, 14H), 5.89(d, J=8.1 Hz, 1H), 5.53(dd, J=8.1, 7.5 Hz, 1H), 5.10–5.01(m, 4H), 4.92(m, 1H), 3.22(dd, J=15.6, 6.9 Hz, 1H), 3.01(dd, J=15.6, 7.8 Hz, 1H), 2.17(dd, J=8.1, 7.2 Hz, 2H), 1.80-1.55(m, 2H), 1.40–1.20(m, 8H), 0.87(t, J=6.9 Hz, 3H).

Example 11

(1R,2R)-1-Octanoylaminoindan-2-ylphosphate

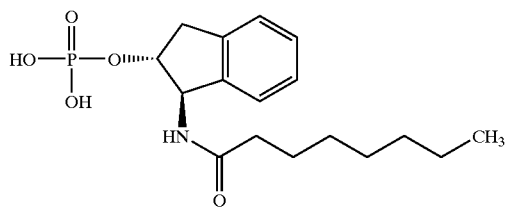

To a solution of the compound prepared in example 10 (245 mg) was added 10% palladium-carbon (30 mg) and the mixture was stirred for 2 hours under an atmosphere of hydrogen. The reaction mixture was filtered and then the filtrate was concentrated. The obtained crystal was washed with diethyl ether to give the compound (133 mg) of the present invention having the following physical data.

TLC: Rf 0.29(Chloroform:Methanol:Water=65:25:4);

NMR(CD₃OD): δ7.30–7.10(m, 4H), 5.39(d, J=5.8 Hz, 1H), 4.85(m, 1H), 3.40(dd, J=16.0, 7.0 Hz, 1H), 3.04(dd, J=16.0, 6.4 Hz, 1H), 2.26(t, J=7.2 Hz, 2H), 1.75–1.55(m, 2H), 1.50–1.20(m, 8H), 0.90(t, J=7.0 Hz, 3H).

Example 12

(1R,2R)-1-Octanoylaminoindan-2-ylphosphate Disodium Salt

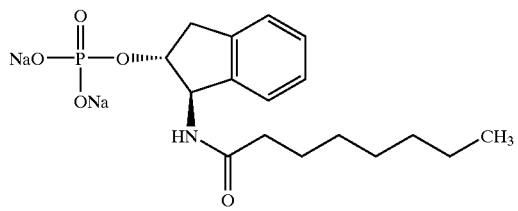

The compound of the present invention having the following physical data was obtained by the same procedure as Example 8, using the compound prepared in Example 11.

TLC: Rf 0.29(Chloroform:Methanol:Water=65:25:4);

NMR(CD₃OD): δ7.14(m, 4H), 5.16(d, J=7.6 Hz, 1H), 4.67(ddd, J=8.0, 7.6, 7.0 Hz, 1H), 3.41(dd, J=15.8, 7.0 Hz, 1H), 2.94(dd, J=15.8, 8.0 Hz, 1H), 2.25(m, 2H), 1.68(m, 2H), 1.45–1.20(m, 8H), 0.89(m, 3H).

Example 13

(1R,2S)-1-Octanoylaminoindan-2-ylphosphate Disodium Salt

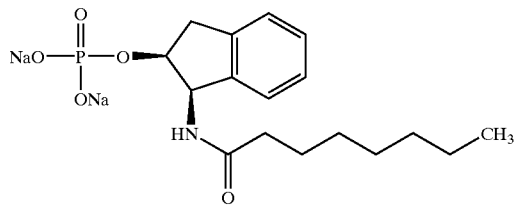

The compound of the present invention having the following physical data was obtained by the same procedure as a series of reactions of Example 2→Example 5→Example 7→Example 8, using (1R,2S)-1-aminoindan-2-ol instead of the compound prepared in Reference example 2.

TLC: Rf 0.29(Chloroform:Methanol:Water=65:25:4);

NMR(CD₃OD): δ7.25–7.05(m, 4H), 5.27(d, J=4.8 Hz, 1H), 5.01(m, 1H), 3.35(m, 1H), 3.03(dd, J=16.4, 4.4 Hz, 1H), 2.50–2.25(m, 2H), 1.70(m, 2H), 1.50–1.20(m, 8H), 0.90(m, 3H).

Reference Example 3

(2R)-2-(5-Phenylpentanoylamino)-2-phenylethanol

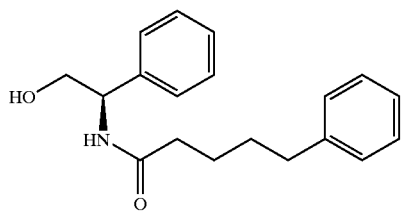

To a solution of 5-phenylpentanoic acid (1.25 g) and hydroxybenzotriazole (1.18 g) in N,N'-dimethylformamide (25 ml) was added 1-ethyl-3-(3-dimethylaminopropyl) carbodiimide hydrochloride (1.74 g) at 0° C. and the mixture was stirred for 1 hour. To the mixture was added (2R)-2-amino-2-phenylethanol (960 mg) and the mixture was stirred for 2 hours at room temperature. The reaction mixture was poured into water (150 ml) and then extracted with ethyl acetate. The organic layer was washed with 2N hydrochloric acid, 2N aqueous solution of sodium hydroxide and a saturated aqueous solution of sodium chloride, successively, dried over anhydrous magnesium sulfate and concentrated under reduced pressure. The obtained crystal was washed with diethy ether to give the title compound (1.09 g) having the following physical data.

TLC: Rf 0.35(Methylene chloride:Methanol=19:1).

Example 14

Dibenzyl-(2R)-2-(5-phenylpentanoylamino)-2-phenylethylphosphate

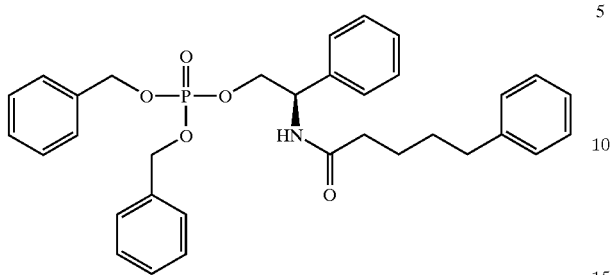

To a solution of the compound prepared in Reference example 3 (594 mg) in tetrahydrofuran (20 ml) was added dropwise n-butyl lithium (1.54M solution in hexane)(1.3 ml) at −78° C., and the mixture was stirred for 5 minutes. To the mixture was added dibenzyl phosphorochloridate (1M solution in tetrahydrofuran) (3 ml) and the mixture was stirred for 2 hours at −78° C. To the reaction mixture was added a saturated aqueous solution of sodium bicarbonate (10 ml) and water (10 ml), and the mixture was allowed to raise to room temperature and then extraced with ethyl acetate. The organic layer was washed with 1N aqueous solution of sodium hydroxide, 1N hydrochloric acid and a saturated aqueous solution of sodium chloride, successively, dried over anhydrous magnesium sulfate, and concentrated. The residue was purified by column chromatography on silica gel (hexane:ethyl acetate=1:1) to give the compound (597 mg) of the present invention having the following physical data.

TLC: Rf 0.25(Hexane:Ethyl acetate=1:1);

NMR(CDCl$_3$): δ7.40–7.10(m, 20H), 6.65(d, J=7.6 Hz, 1H), 5.20(m, 1H), 4.95(d, J=8.4 Hz, 2H), 4.90(dd, J=8.4, 2.6 Hz, 2H), 4.18(dd, J=8.6, 5.0 Hz, 2H), 2.58(brt, J=7.0 Hz, 2H), 2.19(brt, J 7.0 Hz, 2H), 1.80–1.50(m, 4H).

Example 15

(2R)-2-(5-Phenylpentanoylamino)-2-phenylethylphosphate Disodium Salt

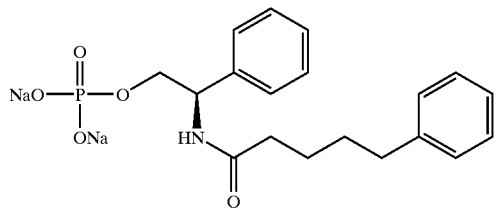

The compound of the present invention having the following physical data was obtained by the same procedure as a series of reactions of Example 11→Example 8, using the compound prepared in Example 14 instead of the compound prepared in Example 11.

TLC: Rf 0.21(Chloroform:Methanol:Water=65:25:4);

NMR(CD$_3$OD): δ7.32(d, J=7.5 Hz, 2H), 7.25–7.10(m, 8H), 4.85(m, 1H), 3.95(m, 2H), 2.59(brt, J=5.7 Hz, 2H), 2.38–2.25(m, 2H), 1.62(m, 4H).

Example 15(1)~Example 15(3)

The compounds of the present invention having the following physical data were obtained by the same procedure as a series of reactions of Reference example 3→Example 14→Example 11→Example 8, using corresponding carboxylic acid instead of 5-phenylpentanoic acid and corresponding aminoalcohol instead of (2R)-2-amino-2-phenylethanol.

Example 15(1)

(2R)-2-Nonanoylamino-2-phenylethylphosphate Disodium Salt

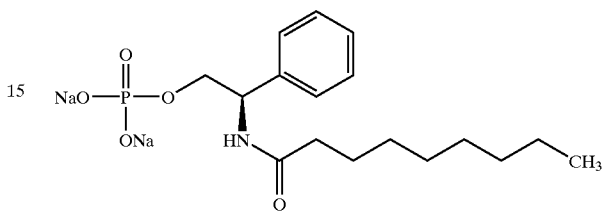

TLC: Rf 0.24(Chloroform:Methanol:Water=65:35:8);

NMR(CD$_3$OD): δ7.36–7.13(m, 5H), 4.80(m, 1H), 3.96 (m, 2H), 2.29(m, 2H), 1.59(m, 2H), 1.40–1.15(m, 10H), 0.88(brt, J=7.0 Hz, 3H).

Example 15(2)

(2R)-2-Decanoylamino-2-phenylethylphosphate Disodium Salt

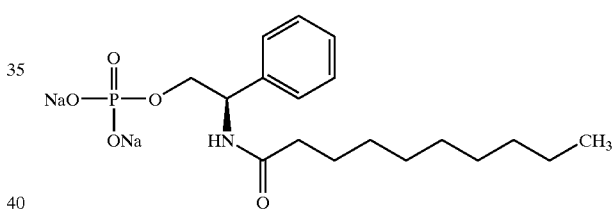

TLC: Rf 0.25(Chloroform:Methanol:Water=65:35:8);

NMR(CD$_3$OD): δ7.36–7.13(m, 5H), 4.80(m, 1H), 3.96 (m, 2H), 2.29(m, 2H), 1.59(m, 2H), 1.40–1.20(m, 12H), 0.88(brt, J=7.0 Hz, 3H).

Example 15(3)

(2R)-2-Undecanoylamino-2-phenylethylphosphate Disodium Salt

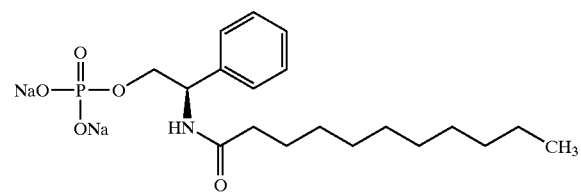

TLC: Rf 0.27(Chloroform:Methanol:Water=65:35:8);

NMR(CD$_3$OD): δ7.36–7.16(m, 5H), 4.80(m, 1H), 3.96 (m, 2H), 2.29(m, 2H), 1.58(m, 2H), 1.40–1.15(m, 14H), 0.88(brt, J=6.4 Hz, 3H).

Example 15(4)

2-Heptylaminocarbonyl-2-phenylethylphosphate Disodium Salt

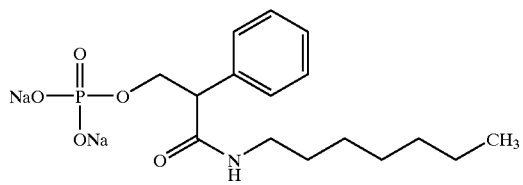

The compound of the present invention having the following physical data was obtained by the same procedure as a series of reactions of Reference example 3→Example 14→Example 11→Example 8, using 3-hydroxy-2-phenylpropionic acid instead of 5-phenylpentanoic acid and N-heptylamine instead of (2R)-2-amino-2-phenylethanol.

TLC: Rf 0.41(Chloroform:Methanol:Water=65:35:8);

NMR(CD$_3$OD): δ7.42–7.33(m, 2H), 7.33–7.15(m, 3H), 4.28(ddd, J=9.9, 9.9, 7.5 Hz, 1H), 4.03(ddd, J=9.9, 6.3, 5.1 Hz, 1H), 3.87(dd, J=9.9, 5.1 Hz, 1H), 3.24(td, J=13.4, 7.5 Hz, 1H), 3.10(td, J=13.4, 7.1 Hz, 1H), 1.60–1.40(m, 2H), 1.40–1.15(m, 8H), 0.87(t, J=6.8 Hz, 3H).

Example 16(1)~Example 16(16)

The compounds of the present invention having the following physical data were obtained by the same procedure as a series of reactions of Example 2→Example 14→Example 11→Example 8, using (2R)-2-amino-2-phenylethanol instead of the compound prepared in Reference example 2 and corresponding compound instead of octanoyl chloride.

Example 16(1)

(2R)-2-Propionylamino-2-phenylethylphosphate Disodium Salt

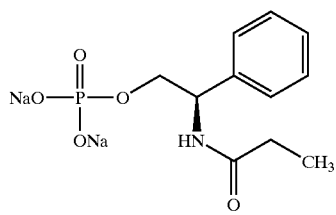

TLC: Rf 0.10(Chloroform:Methanol:Water=65:25:4);

NMR(CD$_3$OD): δ7.40–7.15(m, 5H), 4.85(m, 1H), 3.95 (m, 2H), 2.30(q, J=7.6 Hz, 2H), 1.11(t, J=7.6 Hz, 3H).

Example 16(2)

(2R)-2-Butyrylamino-2-phenylethylphosphate Disodium Salt

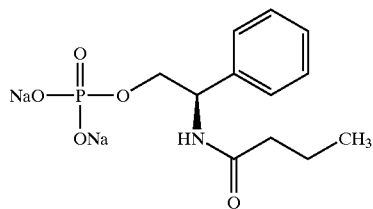

TLC: Rf 0.12(Chloroform:Methanol:Water=65:25:4);

NMR(CD$_3$OD): δ7.40–7.15(m, 5H), 4.85(m, 1H), 3.96 (m, 2H), 2.26(m, 2H), 1.63(ddq, J=7.2, 7.2, 7.2 Hz, 2H), 0.93(t, J=7.2 Hz, 3H).

Example 16(3)

(2R)-2-Pentanoylamino-2-phenylethylphosphate Disodium Salt

TLC: Rf 0.15(Chloroform:Methanol:Water=65:25:4);

NMR(CD$_3$OD): δ7.40–7.15(m, 5H), 4.90(m, 1H), 3.95 (m, 2H), 2.29(m, 2H), 1.59(m, 2H), 1.33(m, 2H), 0.91(t, J=7.2 Hz, 3H).

Example 16(4)

(2R)-2-Hexanoylamino-2-phenylethylphosphate Disodium Salt

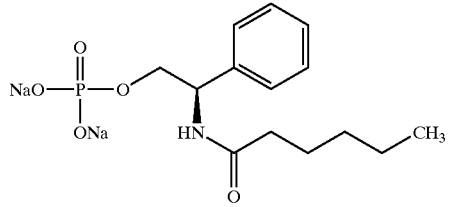

TLC: Rf 0.15(Chloroform:Methanol:Water=65:25:4);

NMR(CD$_3$OD): δ7.40–7.10(m, 5H), 4.90(m, 1H), 3.95 (m, 2H), 2.33(ddd, J=14.0, 7.2, 7.2 Hz, 1H), 2.23(ddd, J=14.0, 7.2, 7.2 Hz, 1H), 1.60(m, 2H), 1.31(m, 4H), 0.89(brt, J=7.2 Hz, 3H).

Example 16(5)

(2R)-2-Heptanoylamino-2-phenylethylphosphate Disodium Salt

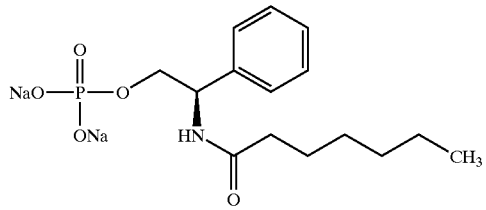

TLC: Rf 0.16(Chloroform:Methanol:Water=65:25:4);

NMR(CD$_3$OD): δ7.40–7.10(m, 5H), 4.90(m, 1H), 3.95 (m,2H), 2.33(ddd, J=14.0, 7.2, 7.2 Hz, 1H), 2.23(ddd, J=14.0, 7.2, 7.2 Hz, 1H), 1.60(m, 2H), 1.31(m, 6H), 0.88(brt, J=7.2 Hz, 3H).

Example 16(6)

(2R)-2-Cyclopropylcarbonylamino-2-phenylethylphosphate Disodium Salt

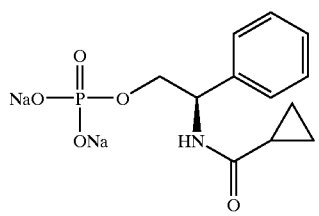

TLC: Rf 0.55(Chloroform:Methanol:Water=65:35:8);

NMR(CD$_3$OD): δ7.35(d, J=7.5 Hz, 2H), 7.26(t, J=7.5 Hz, 2H), 7.17(t, J=7.5 Hz, 1H), 4.60(m, 1H), 3.62(m, 2H), 1.43(m, 1H), 0.37(m, 4H).

Example 16(7)

(2R)-2-t-Butylcarbonylamino-2-phenylethylphosphate Disodium Salt

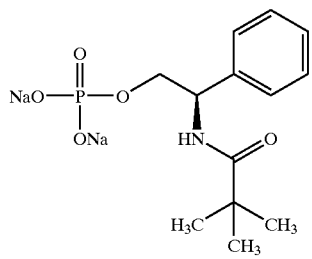

TLC: Rf 0.45(Chloroform:Methanol:Water=65:35:8);

NMR(CD$_3$OD): δ7.33(d, J=7.5 Hz, 2H), 7.26(t, J=7.5 Hz, 2H), 7.16(t, J=7.5 Hz, 1H), 4.63(m, 1H), 3.98(t, J=6.3 Hz, 2H), 1.23(s, 9H).

Example 16(8)

(2R)-2-Acetylamino-2-phenylethylphosphate Disodium Salt

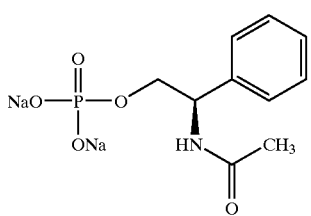

TLC: Rf 0.23(Chloroform:Methanol:Water=65:35:8);

NMR(CD$_3$OD): δ7.40–7.15(m, 5H), 4.85(m, 1H), 3.96 (m, 2H), 2.00(s, 3H).

Example 16(9)

(2R)-2-Ethoxycarbonylamino-2-phenylethylphosphate Disodium Salt

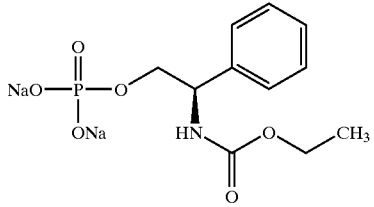

TLC: Rf 0.26(Chloroform:Methanol:Water=65:35:8);

NMR(CD$_3$OD): δ7.36–7.15(m, 5H), 4.72(dd, J=8.4, 3.6 Hz, 1H), 4.03–3.81(m, 4H), 1.19(brt, J=6.6 Hz, 3H).

Example 16(10)

(2R)-2-(N-Methyl-N-octanoylamino)-2-phenylethylphosphate Disodium Salt

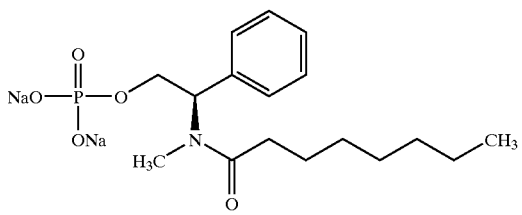

TLC: Rf 0.23(Chloroform:Methanol:Water=65:25:4);

NMR(CD$_3$OD): δ7.34–7.20(m, 5H), 5.94(dd, J=9.0, 6.0 Hz, 0.55 H), 5.32(dd, J=9.0, 5.1 Hz, 0.45 H), 4.41–4.1 3(m, 2H), 2.93(s, 1.65H), 2.88(s, 1.35H), 2.60–2.35(m, 2H), 1.60(m, 2H), 1.45–1.20(m, 8H), 0.89(m, 3H).

Example 16(11)

(2R)-2-Hexyloxycarbonylamino-2-phenylethylphosphate Disodium Salt

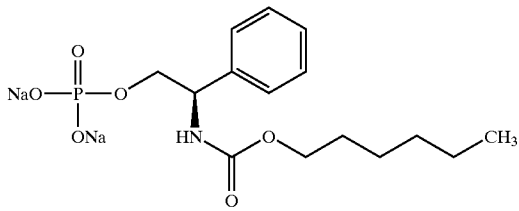

TLC: Rf 0.16(Chloroform:Methanol:Water=65:25:4);

NMR(CD$_3$OD): δ7.36–7.14(m, 5H), 4.70(m, 1H), 3.97–3.78(m, 4H), 1.65–1.10(m, 8H), 0.88(m, 3H).

Example 16(12)

(2R)-2-(2,2-Dimethyloctanoylamino)-2-phenylethylphosphate Disodium Salt

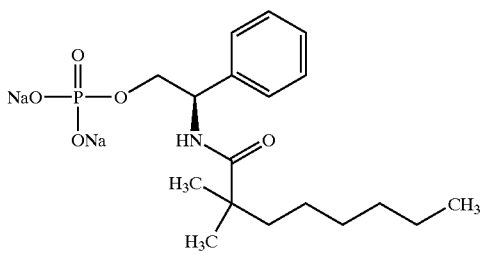

TLC: Rf 0.18(Chloroform:Methanol:Water=65:25:4);

NMR(CD$_3$OD): δ7.36–7.14(m, 5H), 4.85(m, 1H), 3.97 (brt, J=6.2 Hz, 2H), 1.53–1.46(m, 2H), 1.40–1.00(m, 8H), 1.25(s, 3H), 1.14(s, 3H), 0.86(brt, J=6.6 Hz, 3H).

Example 16(13)

(2R)-2-(2,2-Propanooctanoylamino)-2-phenylethylphosphate Disodium Salt

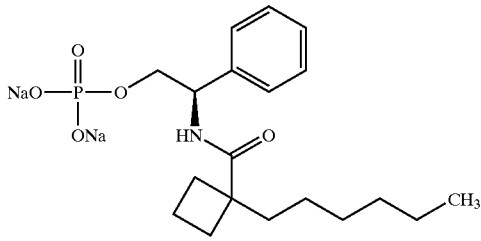

TLC: Rf 0.18(Chloroform:Methanol:Water=65:25:4);

NMR(CD$_3$OD): δ7.38–7.16(m, 5H), 4.90(m, 1H), 3.97 (brt, J=6.2 Hz, 2H), 2.60–2.30(m, 2H), 2.05–1.65(m, 6H), 1.35–1.00(m, 8H), 0.86(brt, J=6.6 Hz, 3H).

Example 16(14)

(2R)-2-(2-methyloctanoylamino)-2-phenylethylphosphate Disodium Salt (Less Polar Isomer)

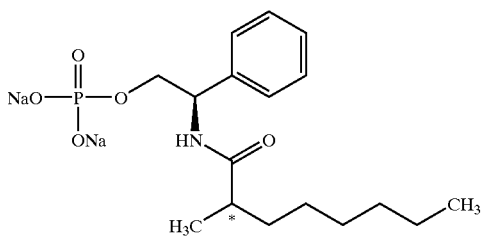

Though the absolute configuration of * is not determined, it is single isomer (less polar isomer). Besides, this compound corresponds to the diastereomer of the compound prepared in Example 16(15).

TLC: Rf 0.25(Chloroform:Methanol:Water=65:25:4);

NMR(CD$_3$OD): δ7.34(brd, J=6.9 Hz, 2H), 7.25(brt, J=7.2 Hz, 2H), 7.16(m, 1H), 4.85(m, 1H), 4.03–3.88(m, 2H), 2.44(m, 1H), 1.60(m, 1H), 1.40–1.20(m, 9H), 1.10(d, J=6.9 Hz, 3H), 0.88(brt, J=6.6 Hz, 3H).

Example 16(15)

(2R)-2-(2-methyloctanoylamino)-2-phenylethylphosphate Disodium Salt (More Polar Isomer)

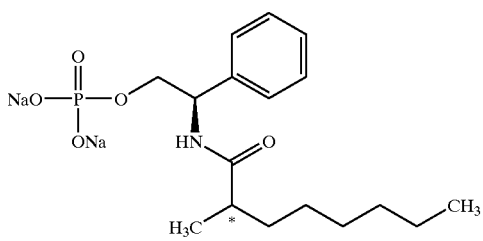

Though the absolute configuration of * is not determined, it is single isomer (more polar isomer). Besides, this compound corresponds to the diastereomer of the compound prepared in Example 16(14).

TLC: Rf 0.20(Chloroform:Methanol:Water=65:25:4);

NMR(CD$_3$OD): δ7.36(brd, J=7.2 Hz, 2H), 7.25(brt, J=7.2 Hz, 2H), 7.17(m, 1H), 4.85(m, 1H), 4.00–3.90(m, 2H), 2.48(m, 1H), 1.55(m, 1H), 1.40–1.15(m, 9H), 1.08(d, J=6.6 Hz, 3H), 0.88(brt, J=6.6 Hz, 3H).

Example 16(16)

(2R)-2-Benzoylamino-2-phenylethylphosphate Disodium Salt

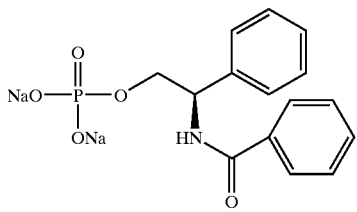

TLC: Rf 0.21(Chloroform:Methanol:Water=65:35:8);

NMR(CD$_3$OD): δ8.00(dd, J=8.0, 2.0 Hz, 2H), 7.50–7.39 (m, 5H), 7.32–7.15(m, 3H), 5.10(brt, J=8.4 Hz, 1H), 4.08(m, 2H).

Example 16(17)

(2R)-2-t-Butoxycarbonylamino-2-phenylethylphosphate Disodium Salt

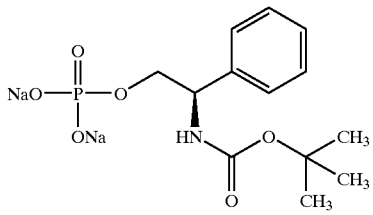

The compound of the present invention having the following physical data was obtained by the same procedure as a series of reactions of Example 14→Example 11→Example 8, using the compound prepared in Reference example 1.

TLC: Rf 0.46(Chloroform:Methanol:Water=65:35:8);

NMR(CD$_3$OD): δ7.35(d, J=7.5 Hz, 2H), 7.21(t, J=7.5 Hz, 2H), 7.18(t, J=7.5 Hz, 1H), 4.66(br, 1H), 4.00–3.76(m, 2H), 1.39(s, 9H).

Reference Example 4

(2R)-2-Octylsulfonylamino-2-phenylethanol

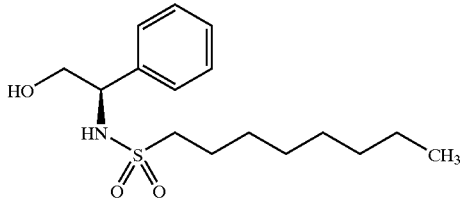

To a solution of (2R)-2-amino-2-phenylethanol (960 mg) in methylene chloride (30 ml) was added triethylamine (2.0 ml) and the mixture was cooled to −78° C. To the mixture was added dropwise chlorotrimethylsilane (0.90 ml), the mixture was stirred for 3 hours at −78° C. and then stirred for 1 hour at 0° C. The reaction mixture was cooled to −78° C. again. To the mixture was added dropwise 1-octanesulfonyl chloride (1.4 ml) and the mixture was stirred for 2 hours at −78° C. and then stirred for 15 hours at 0° C. The reaction mixture was diluted with ethyl acetate and then washed with 1N hydrochloric acid, a saturated aqueous solution of sodium bicarbonate and a saturated aqueous solution of sodium chloride, successively, dried over anhydrous magnesium sulfate and concentrated. The residue was purified by column chromatography on silica gel (hexane:ethyl acetate=2:1→3:2) to give the title compound (1.70 g) having the following physical data.

TLC: Rf 0.50(Methylene chloride:Methanol=19:1).

Example 17

(2R)-2-Octylsulfonylamino-2-phenylethylphosphate Disodium Salt

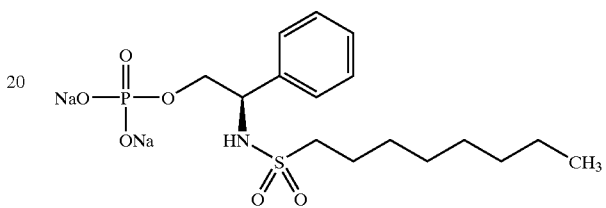

The compound of the present invention having the following physical data was obtained by the same procedure as a series of reactions of Example 14→Example 11→Example 8, using the compound prepared in Reference example 4 instead of the compound prepared in Reference example 3.

TLC: Rf 0.25(Chloroform:Methanol:Water=65:35:8);

NMR(CD$_3$OD): δ7.45–7.23(m, 5H), 4.57(dd, J=7.4, 5.6 Hz, 1H), 3.92(m, 2H), 2.77(m, 2H), 1.65(m, 2H), 1.40–1.10 (m, 10H), 0.88(brt, J=7.0 Hz, 3H).

Reference Example 5

(2R)-2-(N'-Hexylureido)-2-phenylethanol

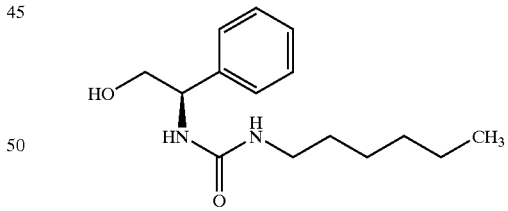

(2R)-2-amino-2-phenylethanol (960 mg) was dissolved in methylene chloride (20 ml) and cooled to 0° C. To the mixture was added hexyl isocyanate (1.0 ml) and the mixture was stirred for 30 minutes at 0° C. and then stirred for 1 hour at room temperature. The solution was washed with 1N hydrochloric acid and a saturated aqueous solution of sodium chloride, successively, dried and concentrated under reduced pressure. The obtained crystal was washed with diethyl ether to give the title compound (930 mg) having the following physical data.

TLC: Rf 0.30(Methylene chloride:Methanol=19:1).

Example 18

(2R)-2-(N'-Hexylureido)-2-phenylethylphosphate Disodium Salt

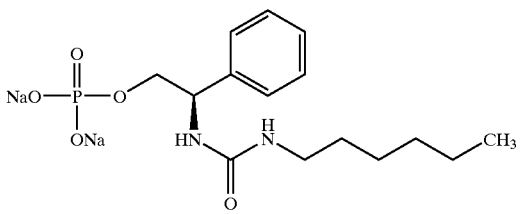

The compound of the present invention having the following physical data was obtained by the same procedure as a series of reactions of Example 14→Example 11→Example 8, using the compound prepared in Reference example 5.

TLC: Rf 0.23(Chloroform:Methanol:Water=65:35:8);

NMR(CD$_3$OD): δ7.37–7.11(m, 5H), 4.73(dd, J=8.0, 4.0 Hz, 1H), 4.03–3.80(m, 2H), 3.05(t, J=6.8 Hz, 2H), 1.50–1.20 (m, 8H), 0.88(brt, J=7.0 Hz, 3H).

Example 19~Example 19(50)

The compounds of the present invention having the following physical data were obtained by the same procedure as a series of reactions of Reference example 3→Example 14→Example 11→Example 8, using corresponding carboxylic acid instead of 5-phenylpentanoic acid and (2R)-2-amino-2-phenylethanol or corresponding aminoalcohol.

Example 19

(2R)-2-Phenyl-2-(4-propyloxybutanoyl)aminoethylphosphate Disodium Salt

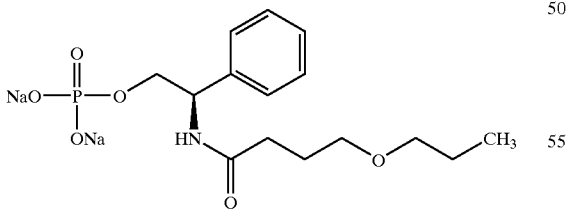

TLC: Rf 0.28(Chloroform:Methanol:Water=65:35:8);

NMR(CD$_3$OD): δ7.40–7.10(m, 5H), 5.02–4.85(m, 1H), 4.10–3.90(m, 2H), 3.42(t, J=6.5 Hz, 2H), 3.36(t, J=6.8 Hz, 2H), 2.50–2.20(m, 2H), 1.98–1.78(m, 2H), 1.70–1.45(m, 2H), 0.91(t, J=7.5 Hz, 3H).

Example 19(1)

(2R)-2-(6-Methoxyhexanoyl)amino-2-phenylethylphosphate Disodium Salt

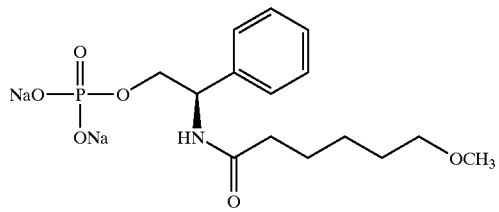

TLC: Rf 0.26(Chloroform:Methanol:Water=65:35:8);

NMR(CD$_3$OD): δ7.40–7.14(m, 5H), 4.98–4.82(m, 1H), 4.02–3.85(m, 2H), 3.37(t, J=6.5 Hz, 2H), 3.30(s, 3H), 2.40–2.20(m, 2H), 1.70–1.50(m, 4H), 1.50–1.30(m, 2H).

Example 19(2)

(2R)-2-Phenyl-2-(2-propylvaleryl)aminoethylphosphate Disodium Salt

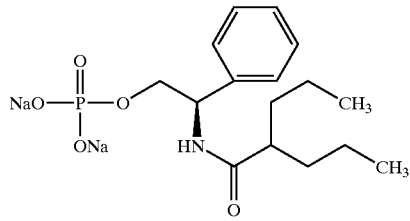

TLC: Rf 0.31(Chloroform:Methanol:Water=65:35:8);

NMR(CD$_3$OD): δ7.40–7.10(m, 5H), 5.00–4.78(m, 1H), 4.05–3.90(m, 2H), 2.50–2.30(m, 1H), 1.70–1.10(m, 8H), 0.90(t, J=6.8 Hz, 3H), 0.87(t, J=6.8 Hz, 3H).

Example 19(3)

(2R)-2-(2-Pentyloxyacetyl)amino-2-phenylethylphosphate Disodium Salt

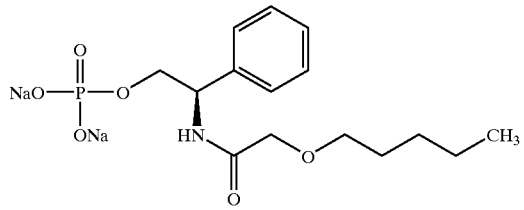

TLC: Rf 0.18(Chloroform:Methanol:Water=65:25:4);

NMR(CD$_3$OD): δ7.36(d, J=7.5 Hz, 2H), 7.30–7.19(m, 3H), 5.03(dd, J=8.1, 4.5 Hz, 1H), 4.03(d, J=16.5 Hz, 1H), 4.00(m, 2H), 3.95(d, J=16.5 Hz, 1H), 3.50(t, J=6.9 Hz, 2H), 1.70–1.55(m, 2H), 1.50–1.30(m, 4H), 0.90(brt, J=6.0 Hz, 3H).

Example 19(4)

(2R)-2-(5-Ethoxyvaleryl)amino-2-phenylethylphosphate Disodium Salt

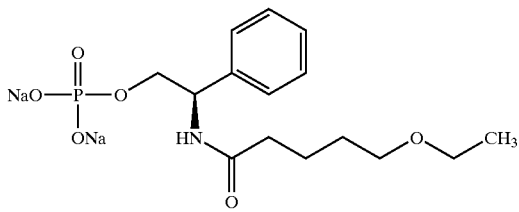

TLC: Rf 0.13(Chloroform:Methanol:Water=65:25:4);

NMR(CD$_3$OD): δ7.36(d, J=7.5 Hz, 2H), 7.30–7.15(m, 3H), 4.90(m, 1H), 3.95(m, 2H), 3.45(q, J=7.2 Hz, 2H), 3.41(t, J=6.0 Hz, 2H), 2.31 (m, 2H), 1.70–1.50(m, 4H), 1.15(t, J=7.2 Hz, 3H).

Example 19(5)

(1S,2R)-2-Heptanoylamino-1-methyl-2-phenylethylphosphate Disodium Salt

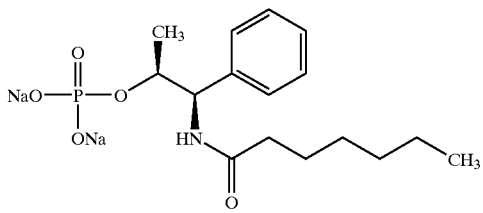

TLC: Rf 0.44(Chloroform:Methanol:Water=65:35:8);

NMR(CD$_3$OD): δ7.43(d, J=6.9 Hz, 2H), 7.28–7.13(m, 3H), 4.63(m, 2H), 2.25(m, 2H), 1.58(m, 2H), 1.26(m, 6H), 1.04(d, J=6.3 Hz, 3H), 0.87(t, J=6.0 Hz, 3H).

Example 19(6)

(1S,2R)-1-Methyl-2-nonanoylamino-2-phenylethylphosphate Disodium Salt

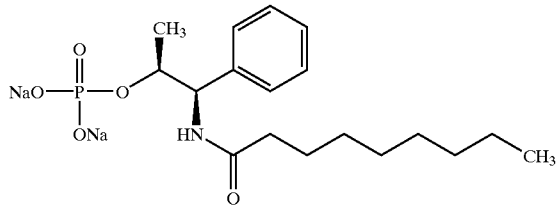

TLC: Rf 0.47(Chloroform:Methanol:Water=65:35:8);

NMR(CD$_3$OD): δ7.43(brd, J=6.9 Hz, 2H), 7.27–7.13(m, 3H), 4.63(m, 2H), 2.25(m, 2H), 1.58(m, 2H), 1.25(m, 10H), 1.04(d, J=6.6 Hz, 3H), 0.88(t, J=6.0 Hz, 3H).

Example 19(7)

2-(4-Methoxyphenyl)-2-octanoylaminoethylphosphate Disodium Salt

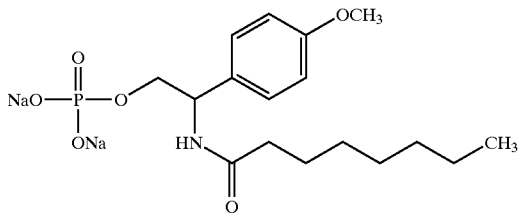

TLC: Rf 0.28(Chloroform:Methanol:Water=65:35:8);

NMR(CD$_3$OD): δ7.26(d, J=8.7 Hz, 2H), 6.82(d, J=8.7 Hz, 2H), 4.92–4.80(m, 1H), 4.00–3.85(m, 1H), 3.75(s, 3H), 2.38–2.18(m, 2H), 1.68–1.50(m, 2H), 1.40–1.20(m, 8H), 0.89(t, J=6.5 Hz, 3H).

Example 19(8)

2-(3-Methoxyphenyl)-2-octanoylaminoethylphosphate Disodium Salt

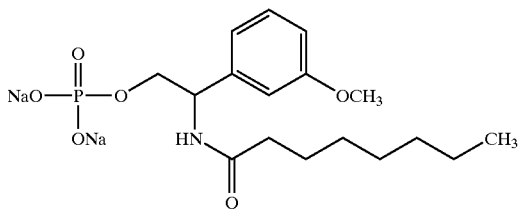

TLC: Rf 0.28(Chloroform:Methanol:Water=65:35:8);

NMR(CD$_3$OD): δ7.18(dd, J=8.1, 8.1 Hz, 1H), 6.95–6.88 (m, 2H), 6.78–6.72(m, 1H), 4.95–4.80(m, 1H), 4.02–3.85 (m, 2H), 3.77(s, 3H), 2.40–2.20(m, 2H), 1.70–1.50(m, 2H), 1.40–1.20(m, 8H), 0.89(t, J=6.3 Hz, 3H).

Example 19(9)

2-(2-Methoxyphenyl)-2-octanoylaminoethylphosphate Disodium Salt

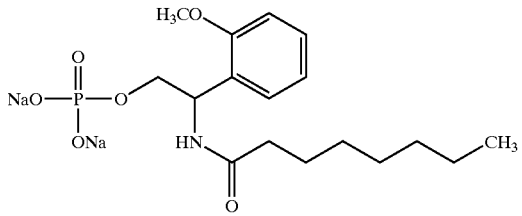

TLC: Rf 0.28(Chloroform:Methanol:Water=65:35:8);

NMR(CD$_3$OD): δ7.26(d, J=7.5 Hz, 1H), 7.17(dd, J=7.5, 7.5 Hz, 1H), 6.90(d, J=7.5 Hz, 1H), 6.85(dd, J=7.5, 7.5 Hz, 1H), 5.29(dd, J=7.8, 3.6 Hz, 1H), 4.08–3.95(m, 1H), 3.95–3.80(m, 4H), 2.40–2.20(m, 2H), 1.70–1.50(m, 2H), 1.40–1.20(m, 8H), 0.89(t, J=6.6 Hz, 3H).

Example 19(10)

2-(2-Methylphenyl)-2-octanoylaminoethylphosphate Disodium Salt

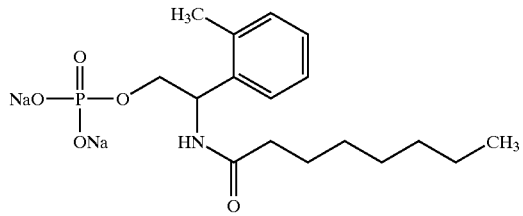

TLC: Rf 0.33(Chloroform:Methanol:Water=65:35:8);

NMR(CD$_3$OD): δ7.33–7.28(m, 1H), 7.13–7.05(m, 3H), 5.12(t, J=6.3 Hz, 1H), 3.87(t like, J=6.3 Hz, 2H), 2.43(s, 3H), 2.36–2.17(m, 2H), 1.64–1.52(m, 2H), 1.33–1.22(m, 8H), 0.88(br.t, J=6.6 Hz, 3H).

Example 19(11)

2-(3-Methylphenyl)-2-octanoylaminoethylphosphate Disodium Salt

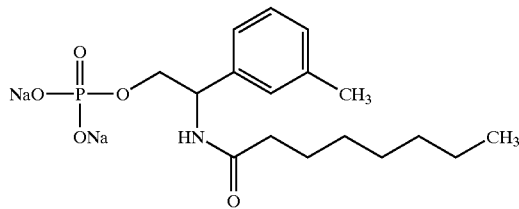

TLC: Rf 0.33(Chloroform:Methanol:Water=65:35:8);

NMR(CD$_3$OD): δ7.17–7.10(m, 3H), 7.04–6.90(m, 1H), 4.85(dd, J=6.3, 4.5 Hz, 1H), 4.00–3.86(m, 2H), 2.38–2.18(m, 2H), 2.92(s, 3H), 1.68–1.52(m, 2H), 1.38–1.20(m, 8H), 0.88(br.t, J=6.3 Hz, 3H).

Example 19(12)

2-(4-Methylphenyl)-2-octanoylaminoethylphosphate Disodium Salt

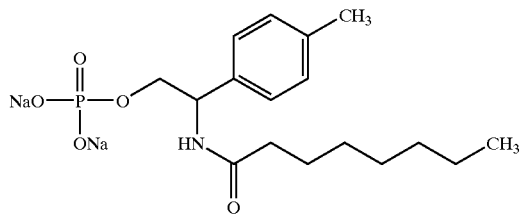

TLC: Rf 0.30(Chloroform:Methanol:Water=65:35:8);

NMR(CD$_3$OD): δ7.22(d, J=8.1 Hz, 2H), 7.08(d, J=8.1 Hz, 2H), 4.90–4.85(m, 1H), 3.99–3.86(m, 2H), 2.36–2.17(m, 2H), 2.27(s, 3H), 1.67–1.52(m, 2H), 1.38–1.24(m, 8H), 0.93–0.86(m, 3H).

Example 19(13)

2-(Naphthalen-1-yl)-2-octanoylaminoethylphosphate Disodium Salt

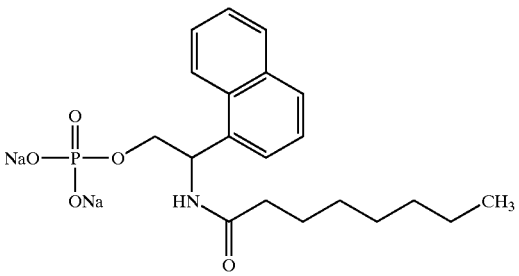

TLC: Rf 0.33(Chloroform:Methanol:Water=65:35:8);

NMR(CD$_3$OD): δ8.21(d, J=8.4 Hz, 1H), 7.88–7.76(m, 2H), 7.59–7.41(m, 4H), 5.95(dd, J=7.5 Hz, 4.5 Hz, 1H), 4.31–4.23(m, 1H), 4.14–4.06(m, 1H), 2.37–2.22(m, 2H), 1.68–1.55(m, 2H), 1.29–1.26(m, 8H), 0.89–0.85(m, 3H).

Example 19(14)

2-(naphthalen-2-yl)-2-octanoylaminoethylphosphate Disodium Salt

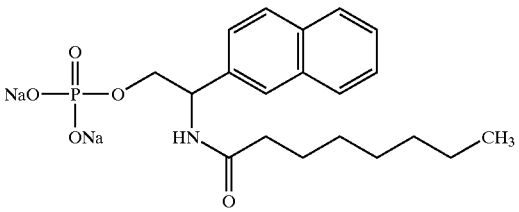

TLC: Rf 0.28(Chloroform:Methanol:Water=65:35:8);

NMR(CD$_3$OD) δ7.80–7.75(m, 4H), 7.50(dd, J=6.9 Hz, 1.5 Hz, 1H), 7.45–7.37(m, 2H), 5.06(dd, J=7.2 Hz, 3.6 Hz, 1H), 4.15–3.98(m, 2H), 2.43–2.23(m, 2H), 1.68–1.57(m, 2H), 1.31–1.26(m, 8H), 0.88–0.84(m, 3H).

Example 19(15)

2-(1,3-Dioxaindan-5-yl)-2-octanoylaminoethylphosphate Disodium Salt

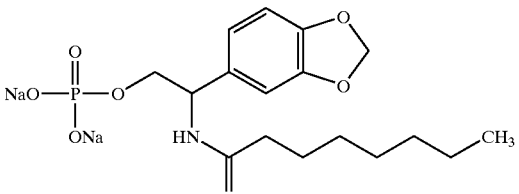

TLC: Rf 0.35(Chloroform:Methanol:Water=65:35:8);

NMR(CD$_3$OD): δ6.86(d, J=1.4 Hz, 1H), 6.81 (dd, J=8.2, 1.4 Hz, 1H), 6.70(d, J=8.2 Hz, 1H), 5.87(s, 2H), 4.80(dd, J=7.6, 4.8 Hz, 1H), 4.00–3.81(m, 2H), 2.38–2.14(m, 2H), 1.70–1.50(m, 2H), 1.35–1.20(m, 8H), 0.95–0.83(m, 3H).

Example 19(16)

2-Octanoylamino-2-(thiophen-2-yl)ethylphosphate Disodium Salt

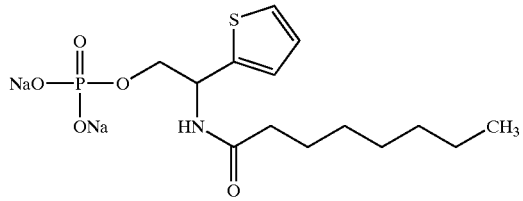

TLC: Rf 0.33(Chloroform:Methanol:Water=65:35:8);

NMR(CD$_3$OD): δ7.20(dd, J=5.0, 1.4 Hz, 1H), 7.03(br.d, J=3.4 Hz, 1H), 6.91(dd, J=50, 3.4 Hz, 1H), 5.22(dd, J=7.4, 4.8 Hz, 1H), 4.15–3.97(m, 2H), 2.38–2.13(m, 2H), 1.70–1.50(m, 2H), 1.40–1.20(m, 8H), 0.93–0.82(m, 3H).

Example 19(17)

2-Octanoylamino-2-(4-trifluoromethylphenyl)ethylphosphate Disodium Salt

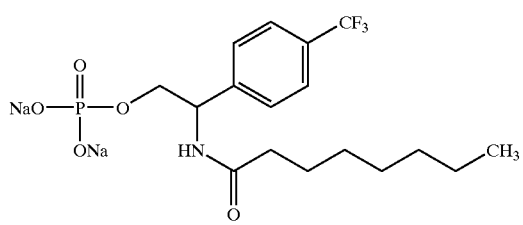

TLC: Rf 0.48(Chloroform:Methanol:Water=65:35:8);

NMR(CD$_3$OD): δ7.60(d, J=8.4 Hz, 2H), 7.54(d, J=8.4 Hz, 2H), 5.12–5.09(m, 1H), 4.13–4.04(m, 2H), 2.30–2.25(m, 2H), 1.66–1.53(m, 2H), 1.38–1.21(m, 8H), 0.92–0.85(m, 3H).

Example 19(18)

2-Octanoylamino-2-(2-trifluoromethylphenyl)ethylphosphate Disodium Salt

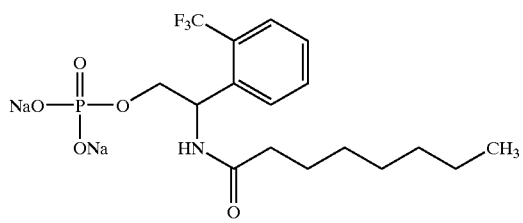

TLC: Rf 0.50(Chloroform:Methanol:Water=65:35:8);

NMR(CD$_3$OD): δ7.67(t, J=8 Hz, 2H), 7.58(t, J=8 Hz, 1H), 7.41(t, J=8 Hz, 1H), 5.41(dd, J=6.9, 3.6 Hz, 1H), 4.13–4.02(m, 1H), 4.00–3.90(m, 1H), 2.25(m, 2H), 1.57(m, 2H), 1.40–1.20(m, 8H), 0.88(t, J=6.3 Hz, 3H).

Example 19(19)

2-(3,5-Dimethoxyphenyl)-2-octanoylaminoethylphosphate Disodium Salt

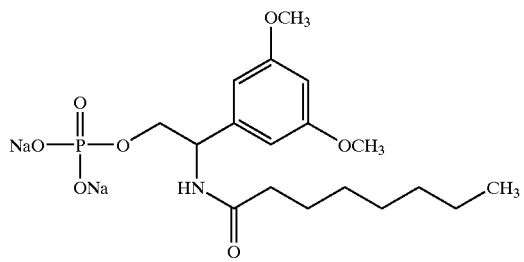

TLC: Rf 0.50(Chloroform:Methanol:Water=65:35:8);

NMR(CD$_3$OD): δ6.51(d, J=2.4 Hz, 2H), 6.30(t, J=2.4 Hz, 1H), 4.83(dd, J=7.8, 4.2 Hz, 1H), 4.01–3.87(m, 2H), 3.73(s, 6H), 2.39–2.18(m, 2H), 1.70–1.52(m, 2H), 1.37–1.24(m, 8H), 0.92–0.85(m, 3H).

Example 19(20)

2-(3-Fluorophenyl)-2-octanoylaminoethylphosphate Disodium Salt

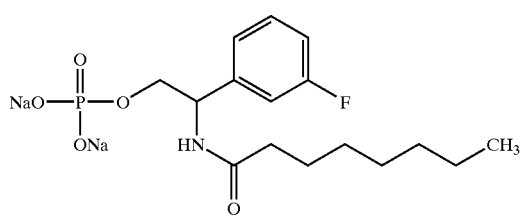

TLC: Rf 0.32(Chloroform:Methanol:Water=65:35:8);

NMR(CD$_3$OD): δ7.27(dt, J=5.7, 7.8 Hz, 1H), 7.16(d, J=7.8 Hz, 1H), 7.11–7.07(m, 1H), 6.94–6.87(m, 1H), 4.91–4.87(m, 1H), 4.05–3.88(m, 2H), 2.38–2.20(m, 2H), 1.68–1.53(m, 2H), 1.34–1.24(m, 8H), 0.92–0.85(m, 3H).

Example 19(21)

2-(3-Ethoxyphenyl)-2-octanoylaminoethylphosphate Disodium Salt

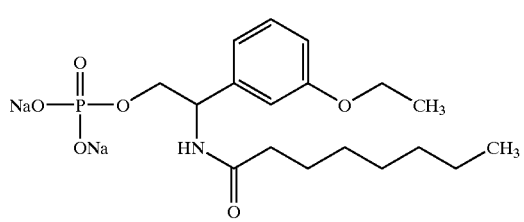

TLC: Rf 0.22(Chloroform:Methanol:Water=65:25:4);

NMR(CD$_3$OD): δ7.15(t, J=8.1 Hz, 1H), 6.89(m, 2H), 6.72(dd, J=8.1, 1.8 Hz, 1H), 4.83(m, 1H), 4.05–3.87(m, 4H), 2.38–2.18(m, 2H), 1.61(m, 2H), 1.35(t, J=7.2 Hz, 3H), 1.30–1.20(m, 8H), 0.88(brt, J=6.6 Hz, 3H).

Example 19(22)

2-Octanoylamino-2-(3-propyloxyphenyl)
ethylphosphate Disodium Salt

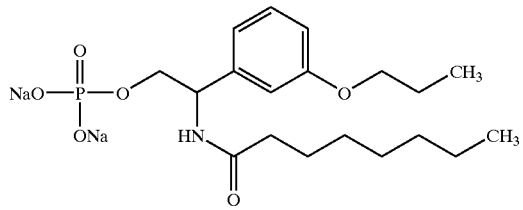

TLC: Rf 0.22(Chloroform:Methanol:Water=65:25:4);

NMR(CD$_3$OD): δ7.15(t, J=8.1Hz, 1H), 6.89(m, 2H), 6.72 (dd, J=8.1, 1.8 Hz, 1H), 4.83(m, 1H), 4.00–3.87(m, 4H), 2.38–2.18(m, 2H), 1.76(tq, J=7.5, 7.5 Hz, 2H), 1.61(m, 2H), 1.38–1.20(m, 8H), 1.02(t, J=7.5 Hz, 3H), 0.88(brt, J=6.6 Hz, 3H).

Example 19(23)

2-(3-Isopropyloxyphenyl)-2-
octanoylaminoethylphosphate Disodium Salt

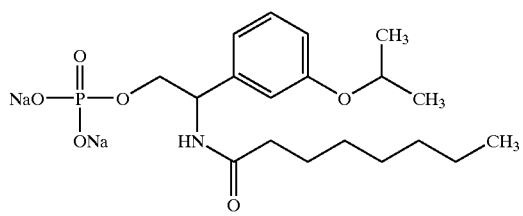

TLC: Rf 0.22(Chloroform:Methanol:Water=65:25:4);

NMR(CD$_3$OD): δ7.14(t, J=8.1 Hz, 1H), 6.89(m, 2H), 6.72(dd, J=8.1, 2.4 Hz, 1H), 4.83(m, 1H), 4.56(qq, J=6.0, 6.0 Hz, 1H), 4.00–3.87(m, 2H), 2.38–2.18(m, 2H), 1.62(m, 2H), 1.38–1.20(m, 8H), 1.28(d, J=6.0 Hz, 3H), 1.26(d, J=6.0 Hz, 3H), 0.88(brt, J=6.6 Hz, 3H).

Example 19(24)

2-Octanoylamino-2-(3-trifluoromethylphenyl)
ethylphosphate Disodium Salt

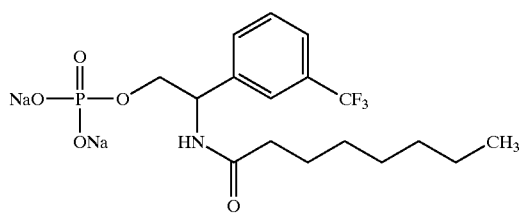

TLC: Rf 0.26(Chloroform:Methanol:Water=65:35:8);

NMR(CD$_3$OD): δ7.65–7.63(m, 2H), 7.55–7.47(m, 2H), 5.12(dd, J=6.6 Hz, 4.2 Hz, 1H), 4.13–3.98(m, 2H), 2.35–2.20(m, 2H), 1.68–1.55(m, 2H), 1.31–1.23(m, 8H), 0.90–0.86(m, 3H).

Example 19(25)

2-(1,3-Dioxaindan-4-yl)-2-
octanoylaminoethylphosphate Disodium Salt

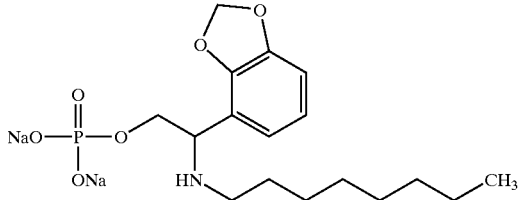

TLC: Rf 0.31(Chloroform:Methanol:Water=65:25:4);

NMR(CD$_3$OD): δ6.81(dd, J=7.5, 1.5 Hz, 1H), 6.73(t, J=7.5 Hz, 1H), 6.66(dd, J=7.5, 1.5 Hz, 1H), 5.93(dd, J=3.9, 1.2 Hz, 2H), 5.03(t, J=6.0 Hz, 1H), 4.01(t, J=6.0 Hz, 2H), 2.29(m, 2H), 1.59(m, 2H), 1.40–1.20(m, 8H), 0.89(t, J=6.6 Hz, 3H).

Example 19(26)

(2R)-2-(3-Methoxyphenyl)-2-
octanoylaminoethylphosphate Disodium Salt

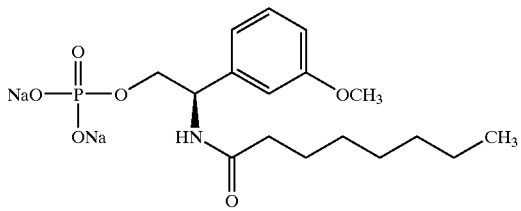

TLC: Rf 0.51(Chloroform:Methanol:Water=65:35:8);

NMR(CD$_3$OD): δ7.18(dd, J=8.1, 8.1 Hz, 1H), 6.95–6.88 (m, 2H), 6.78–6.72(m, 1H), 4.95–4.80(m, 1H), 4.02–3.85 (m, 2H), 3.77(s, 3H), 2.40–2.20(m, 2H), 1.70–1.50(m, 2H), 1.40–1.20(m, 8H), 0.89(t, J=6.8 Hz, 3H).

Example 19(27)

2-Heptanoylamino-2-(3-methoxyphenyl)
ethylphosphate Disodium Salt

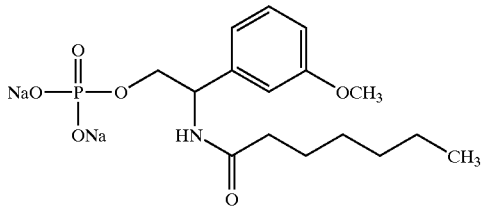

TLC: Rf 0.40(Chloroform:Methanol:Water=65:35:8);

NMR(CD$_3$OD): δ7.17(t, J=8.4 Hz, 1H), 6.92–6.89(m, 2H), 6.75–6.72(m, 1H), 4.86–4.84(m, 1H), 4.01–3.87(m, 2H), 3.76(s, 3H), 2.38–2.18(m, 2H), 1.63–1.58(m, 2H), 1.34–1.29(m, 6H), 0.88(t, J=6.6 Hz, 3H).

Example 19(28)

2-Hexanoylamino-2-(3-methoxyphenyl)ethylphosphate Disodium Salt

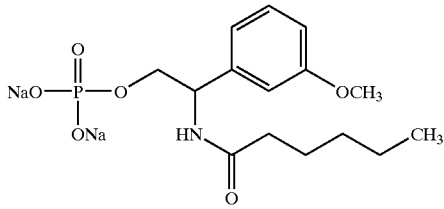

TLC: Rf 0.32(Chloroform:Methanol:Water=65:35:8);

NMR(CD$_3$OD): δ7.17(t, J=8.1 Hz, 1H), 6.92–6.90(m, 2H), 6.76–6.72(m, 1H), 4.88–4.84(m, 1H), 4.02–3.88(m, 2H), 3.76(s, 3H), 2.30–2.19(m, 2H), 1.65–1.56(m, 2H), 1.66–1.29(m, 4H), 0.89(t, J=6.9 Hz, 3H).

Example 19(29)

2-(3-Methoxyphenyl)-2-valerylaminoethylphosphate Disodium Salt

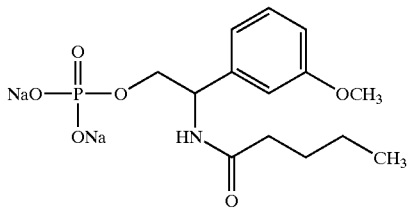

TLC: Rf 0.21(Chloroform:Methanol:Water=65:35:8);

NMR(CD$_3$OD): δ7.16(t, J=8.1 Hz, 1H), 6.92–6.89(m, 2H), 6.75–6.71(m, 1H), 4.88–4.83(m, 1H), 4.01–3.88(m, 2H), 3.76(s, 3H), 2.38–2.19(m, 2H), 1.64–1.53(m, 2H), 1.40–1.28(m, 2H), 0.91(t, J=7.2 Hz, 3H).

Example 19(30)

2-(3-(2-Methoxyethoxy)phenyl)-2-octanoylaminoethylphosphate Disodium Salt

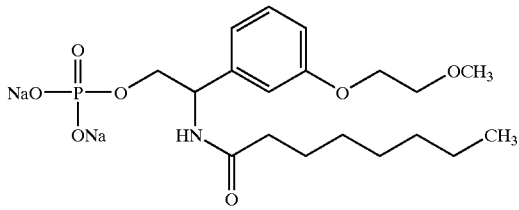

TLC: Rf 0.36(Chloroform:Methanol:Water=65:25:4);

NMR(CD$_3$OD): δ7.17(t, J=8.1 Hz, 1H), 6.96–6.88(m, 2H), 6.80–6.74(m, 1H), 4.80–4.78(m, 1H), 4.16–4.04(m, 2H), 4.02–3.88(m, 2H), 3.72(t, J=4.5 Hz, 2H), 3.41(s, 3H), 2.40–2.18(m, 2H), 1.70–1.50(m, 2H), 1.40–1.20(m, 8H), 0.89(brt, J=6.6 Hz, 3H).

Example 19(31)

2-(3-Butoxyphenyl)-2-octanoylaminoethylphosphate Disodium Salt

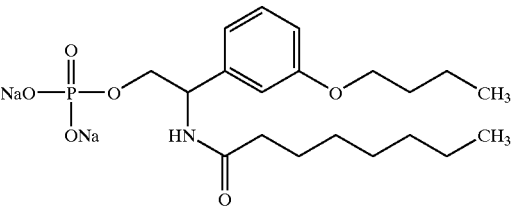

TLC: Rf 0.35(Chloroform:Methanol:Water=65:25:4);

NMR(CD$_3$OD): δ7.15(t, J=8.1 Hz, 1H), 6.89(m, 2H), 6.72(dd, J=8.1, 2.4 Hz, 1H), 4.83(m, 1H), 4.00–3.87(m, 4H), 2.40–2.18(m, 2H), 1.77–1.40(m, 6H), 1.40–1.20(m, 8H), 0.97(t, J=7.5 Hz, 3H), 0.88(brt, J=6.3 Hz, 3H).

Example 19(32)

2-Octanoylamino-2-(3-pentyloxyphenyl)ethylphosphate Disodium Salt

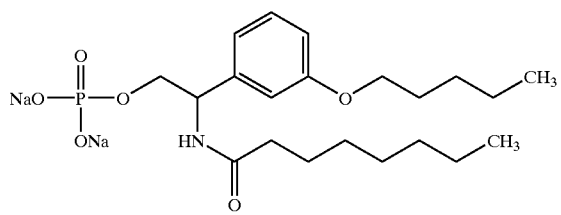

TLC: Rf 0.35(Chloroform:Methanol:Water=65:25:4);

NMR(CD$_3$OD): δ7.15(t, J=8.1 Hz, 1H), 6.89(m, 2H), 6.72(dd, J=8.1, 1.8 Hz, 1H), 4.83(m, 1H), 4.00–3.87(m, 4H), 2.40–2.18(m, 2H), 1.80–1.20(m, 16H), 0.94(t, J=7.2 Hz, 3H), 0.88(brt, J=6.3 Hz, 3H).

Example 19(33)

2-(3-Hexyloxyphenyl)-2-octanoylaminoethylphosphate Disodium Salt

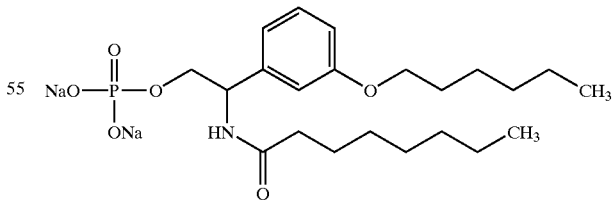

TLC: Rf 0.35(Chloroform:Methanol:Water=65:25:4);

NMR(CD$_3$OD): δ7.15(t, J=8.1 Hz, 1H), 6.89(m, 2H), 6.73(dd, J=8.1, 2.4 Hz, 1H), 4.83(m, 1H), 4.00–3.87(m, 4H), 2.40–2.18(m, 2H), 1.80–1.20(m, 18H), 0.92(t, J=6.9 Hz, 3H), 0.88(brt, J=6.6 Hz, 3H).

Example 19(34)

2-(3-Methoxymethylphenyl)-2-octanoylaminoethylphosphate Disodium Salt

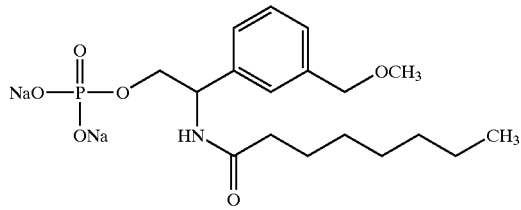

TLC: Rf 0.41(Chloroform:Methanol:Water=65:35:8);

NMR(CD$_3$OD): δ7.32(brs, 1H), 7.31–7.23(m, 2H), 7.17 (brd, J=6.6 Hz, 1H), 4.92–4.87(m, 1H), 4.42(s, 2H), 4.02–3.88(m, 2H), 3.33(s, 3H), 2.38–2.19(m, 2H), 1.66–1.53(m, 2H), 1.35–1.24(m, 8H), 0.92–0.85(m, 3H).

Example 19(35)

2-(3-Cyclopentyloxyphenyl)-2-octanoylaminoethylphosphate Disodium Salt

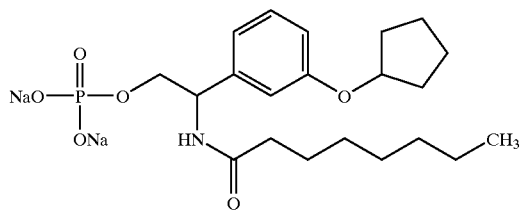

TLC: Rf 0.26(Chloroform:Methanol:Water=65:25:4);

NMR(CD$_3$OD): δ7.14(t, J=7.8 Hz, 1H), 6.87(m, 2H), 6.69(dd, J=7.8, 1.8 Hz, 1H), 4.84(m, 1H), 4.77(m, 1H), 4.00–3.87(m, 2H), 2.40–2.18(m, 2H), 1.95–1.50(m, 10H), 1.40–1.20(m, 8H), 0.88(brt, J=6.6 Hz, 3H).

Example 19(36)

2-(3-(2-Methylpropyloxy)phenyl)-2-octanoylaminoethylphosphate Disodium Salt

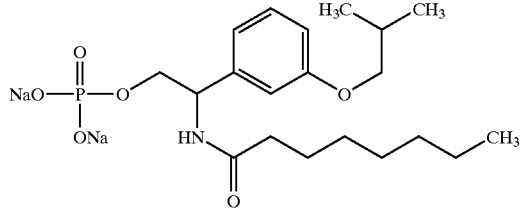

TLC: Rf 0.26(Chloroform:Methanol:Water=65:25:4);

NMR(CD$_3$OD): δ7.15(t, J=7.8 Hz, 1H), 6.89(m, 2H), 6.73(dd, J=7.8, 1.8 Hz, 1H), 4.84(m, 1H), 4.00–3.88(m, 2H), 3.75–3.65(m, 2H), 2.39–2.18(m, 2H), 2.09–1.95(m, 1H), 1.70–1.50(m, 2H), 1.40–1.20(m, 8H), 1.01(d, J=6.9 Hz, 6H), 0.88(brt, J=6.6 Hz, 3H).

Example 19(37)

2-Acetylamino-2-(3-methoxyphenyl)ethylphosphate Disodium Salt

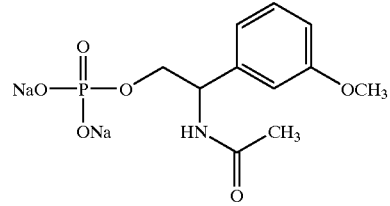

TLC: Rf 0.13(Chloroform:Methanol:Water 65:35:8);

NMR(CD$_3$OD): δ7.17(t, J=8.1 Hz, 1H), 6.92–6.89(m, 2H), 6.76–6.72(m, 1H), 4.86–4.82(m, 1H), 4.02–3.88(m, 2H), 3.76(s, 3H), 2.00(s, 3H).

Example 19(38)

2-Octanoylamino-2-(3-trifluoromethyloxyphenyl)ethylphosphate Disodium Salt

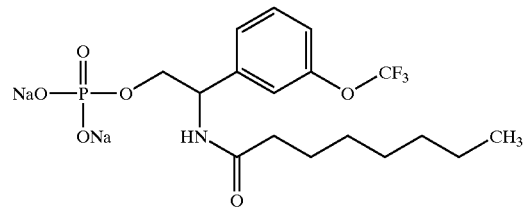

TLC: Rf 0.37(Chloroform:Methanol:Water=65:35:8);

NMR(CD$_3$OD): δ7.37(m, 2H), 7.25(s, 1H), 7.11–7.07(m, 1H), 4.90(dd, J=8.1 Hz, 3.9 Hz, 1H), 4.06–3.89(m, 2H), 2.39–2.19(m, 2H), 1.63–1.53(m, 2H), 1.35–1.26(m, 8H), 0.88(t, J=6.9 Hz, 3H).

Example 19(39)

2-(3-Dimethylaminocarbonylmethyloxyphenyl)-2-octanoylaminoethylphosphate Disodium Salt

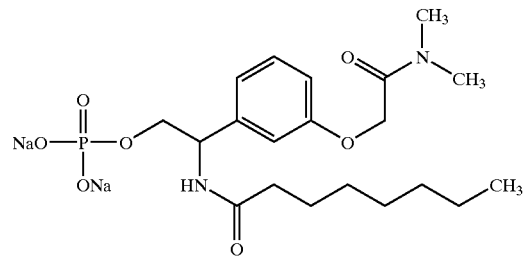

TLC: Rf 0.30(Chloroform:Methanol:Water=65:35:8);

NMR(CD$_3$OD): δ7.18(t, J=8.1 Hz, 1H), 6.98–6.96(m, 2H), 6.83–6.80(m, 1H), 4.88–4.84(m, 1H), 4.75(s, 2H), 3.99–3.91(m, 2H), 3.09(s, 3H), 2.96(s, 3H), 2.38–2.18(m, 2H), 1.66–1.53(m, 2H), 1.30–1.28(m, 8H), 0.88(t, J=6.9 Hz, 3H).

Example 19(40)

(2S)-2-(3-Methoxyphenyl)-2-octanoylaminoethylphosphate Disodium Salt

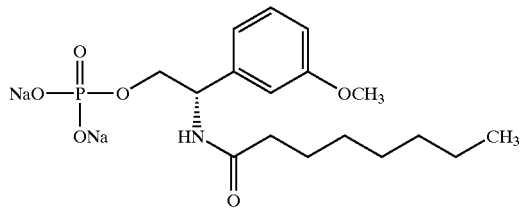

TLC: Rf 0.26(Chloroform:Methanol:Water=65:35:8);

NMR(CD$_3$OD): δ7.17(t, J=8.0 Hz, 1H), 6.92–6.89(m, 2H), 6.76–6.71(m, 1H), 4.89–4.83(m, 1H), 3.98–3.90(m, 2H), 3.76(s, 3H), 2.42–2.17(m, 2H), 1.67–1.55(m, 2H), 1.29–1.25(m, 8H), 0.88(t, J=7.0 Hz, 3H).

Example 19(41)

2-(3-Cyclobutyloxyphenyl)-2-octanoylaminoethylphosphate Disodium Salt

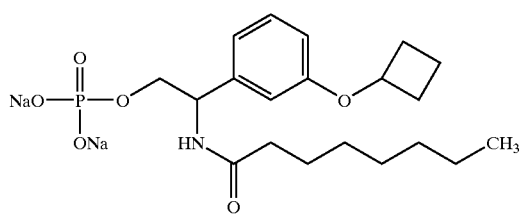

TLC: Rf 0.21(Chloroform:Methanol:Water=65:25:4);

NMR(CD$_3$OD) δ7.13(t, J=7.8 Hz, 1H), 6.89(brd, J=7.8 Hz, 1H), 6.79(brt, J=1.8 Hz, 1H), 6.63(dd, J=7.8, 1.8 Hz, 1H), 4.84(m, 1H), 4.64(m, 1H), 3.98–3.86(m, 2H), 2.50–2.00(m, 6H), 1.85–1.50(m, 4H), 1.40–1.20(m, 8H), 0.88(brt, J=6.6 Hz, 3H).

Example 19(42)

2-(3-(1-Ethylpropyloxy)phenyl)-2-octanoylaminoethylphosphate Disodium Salt

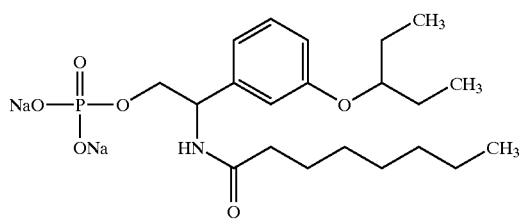

TLC: Rf 0.23(Chloroform:Methanol:Water=65:25:4);

NMR(CD$_3$OD): δ7.14(t, J=8.1 Hz, 1H), 6.88(m, 2H), 6.72(dd, J=8.1, 1.8 Hz, 1H), 4.84(m, 1H), 4.14(m, 1H), 4.00–3.87(m, 2H), 2.40–2.18(m, 2H), 1.70–1.50(m, 6H), 1.40–1.20(m, 8H), 0.94(t, J=7.5 Hz, 3H), 0.93(t, J=7.5 Hz, 3H), 0.88(brt, J=6.9 Hz, 3H).

Example 19(43)

2-(3-Methoxymethoxyphenyl)-2-octanoylaminoethylphosphate Disodium Salt

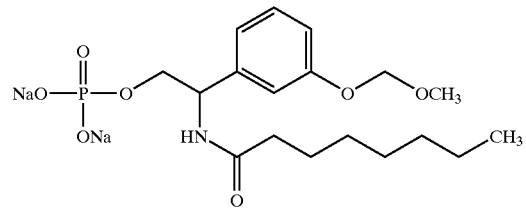

TLC: Rf 0.28(Chloroform:Methanol:Water=65:35:8);

NMR(CD$_3$OD): δ7.18(t, J=7.8 Hz, 1H), 7.01(brs, 1H), 6.98(brd, J=7.8 Hz, 1H), 6.86(ddd, J=7.8, 2.1, 0.9 Hz, 1H), 5.16(d, J=6.6 Hz, 1H), 5.13(d, J=6.6 Hz, 1H), 4.88–4.82(m, 1H), 4.01–3.87(m, 2H), 3.42(s, 3H), 2.38–2.18(m, 2H), 1.69–1.53(m, 2H), 1.36–1.24(m, 8H), 0.91–0.86(m, 3H).

Example 19(44)

(1S,2R)-2-(3-Methoxyphenyl)-1-methyl-2-octanoylaminoethylphosphate Disodium Salt

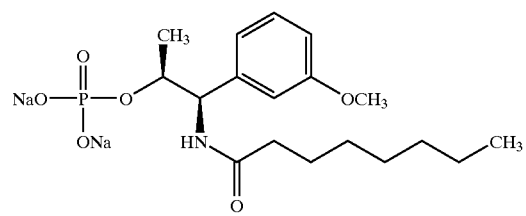

TLC: Rf 0.28(Chloroform:Methanol:Water=65:35:8);

NMR(CD$_3$OD): δ7.14(t, J=8.4 Hz, 1H), 7.01–6.99(m, 2H), 6.74(ddd, J=8.4, 2.7, 1.2 Hz, 1H), 4.65–4.53(m, 2H), 3.78(s, 3H), 2.35–2.19(m, 2H), 1.61–1.49(m, 2H), 1.30–1.20(m, 8H), 1.05(d, J=6.3 Hz, 3H), 0.88–0.84(m, 3H).

Example 19(45)

(1S,2R)-2-(3-Isopropyloxyphenyl)-1-methyl-2-octanoylaminoethylphosphate Disodium Salt

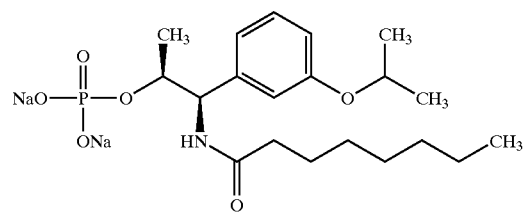

TLC: Rf 0.33(Chloroform:Methanol:Water=65:35:8);

NMR(CD$_3$OD): δ7.12(t, J=7.8 Hz, 1H), 6.99(brd, J=7.8 Hz, 1H), 6.96(brs, 1H), 6.73–6.69(m, 1H), 4.64–4.54(m, 3H), 2.35–2.19(m, 2H), 1.61–1.49(m, 2H), 1.29(d, J=6.0 Hz, 3H), 1.26(d, J=6.0 Hz, 3H), 1.30–1.20(m, 8H), 1.06(d, J=6.3 Hz, 3H), 0.89–0.84(m, 3H).

Example 19(46)

(1R,2R)-2-(3-Methoxyphenyl)-1-methyl-2-octanoylaminoethylphosphate Disodium Salt

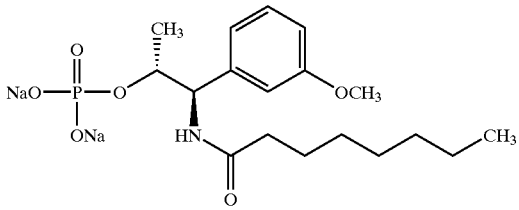

TLC: Rf 0.28(Chloroform:Methanol:Water=65:25:4);

NMR(CD$_3$OD): δ7.16(dd, J=8.0, 8.0 Hz, 1H), 6.92(m, 2H), 6.74(ddd, J=8.0, 2.4, 1.2 Hz, 1H), 4.35–4.29(m, 2H), 3.76(s, 3H), 2.38–2.12(m, 2H), 1.53(m, 2H), 1.30–1.20(m, 8H), 1.05(d, J=6.0 Hz, 3H), 0.86(brt, J=6.6 Hz, 3H).

Example 19(47)

(1R,2S)-2-(3-Methoxyphenyl)-1-methyl-2-octanoylaminoethylphosphate Disodium Salt

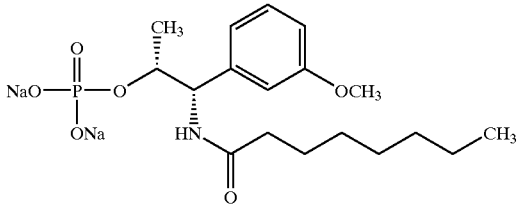

TLC: Rf 0.20(Chloroform:Methanol:Water=65:25:4);

NMR(CD$_3$OD): δ7.13(dd, J=8.1, 8.1 Hz, 1H), 7.01–6.99 (m, 2H), 6.73(ddd, J=8.1, 2.4, 1.2 Hz, 1H), 4.63–4.57(m, 2H), 3.77(s, 3H), 2.36–2.18(m, 2H), 1.55(m, 2H), 1.35–1.20 (m, 8H), 1.05(d, J=6.3 Hz, 3H), 0.86(brt, J=6.6 Hz, 3H).

Example 19(48)

(1S,2S)-2-(3-Methoxyphenyl)-1-methyl-2-octanoylaminoethylphosphate Disodium Salt

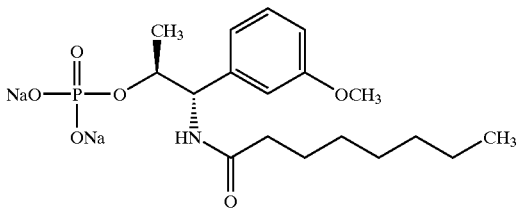

TLC: Rf 0.22(Chloroform:Methanol:Water=65:25:4);

NMR(CD$_3$OD): δ7.16(dd, J=8.0, 8.0 Hz, 1H), 6.92(m, 2H), 6.74(ddd, J=8.0, 2.4, 1.2 Hz, 1H), 4.35–4.29(m, 2H), 3.76(s, 3H), 2.38–2.12(m, 2H), 1.53(m, 2H), 1.30–1.20(m, 8H), 1.05(d, J=6.0 Hz, 3H), 0.86(brt, J=6.6 Hz, 3H).

Example 19(49)

2-Octanoylamino-2-(pyridin-2-yl)ethylphosphate Disodium Salt

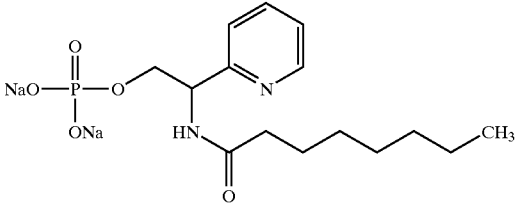

TLC: Rf 0.12(Chloroform:Methanol:Water=65:25:4);

NMR(CD$_3$OD): δ8.42(brd, J=5.1 Hz, 1H), 7.73(ddd, J=7.5, 7.5, 1.5 Hz, 1H), 7.47(brd, J=7.8 Hz, 1H), 7.23(ddd, J=7.5, 5.1, 1.2 Hz, 1H), 4.94(dd, J=6.3, 3.6 Hz, 1H), 4.17(ddd, J=10.8, 6.6, 3.6 Hz, 1H), 4.08(ddd, J=10.8, 7.2, 6.3 Hz, 1H), 2.40–2.24(m, 2H), 1.61(m, 2H), 1.40–1.20(m, 8H), 0.89(brt, J=6.6 Hz, 3H).

Example 19(50)

2-Octanoylamino-2-(pyridin-3-yl)ethylphosphate Disodium Salt

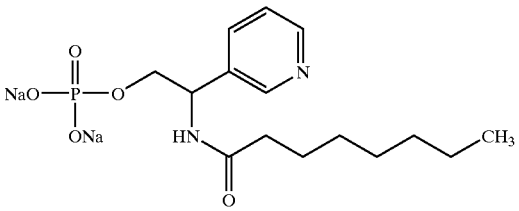

TLC: Rf 0.11(Chloroform:Methanol:Water=65:25:4);

NMR(CD$_3$OD): δ8.54(d, J=1.6 Hz, 1H), 8.36(dd, J=5.0, 1.6 Hz, 1H), 7.88(brd, J=8.2 Hz, 1H), 7.36(dd, J=8.2, 5.0 Hz, 1H), 4.93(dd, J=6.4, 3.8 Hz, 1H), 4.18–3.89(m, 2H), 2.33–2.24(m, 2H), 2.40–2.24(m, 2H), 1.70–1.50(m, 2H), 1.40–1.15(m, 8H), 0.87(brt, J=6.6 Hz, 3H).

Reference Example 6

2-Pentylthioacetylamino-2-phenylethanol

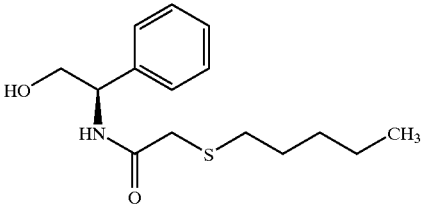

The compound of the present invention having the following physical data was obtained by the same procedure as Reference example 3, using pentylthioacetic acid instead of phenylpentanoic acid.

TLC: Rf 0.12(Hexane:Ethyl acetate=1:1);

NMR(CDCl$_3$): δ7.56(brd, J=6.9 Hz, 1H), 7.40–7.30(m, 5H), 5.09(ddd, J=7.8, 4.8, 4.8 Hz, 1H), 3.90(brd, J=4.8 Hz, 2H), 3.30(d, J=16.8 Hz, 1H), 3.23(d, J=16.8 Hz, 1H), 2.53(m, 1H), 2,53(brt, J=6.9 Hz, 2H), 1.65–1.50(m, 2H), 1.40–1.20(m, 4H), 0.87(brt, J=7.2 Hz, 3H).

Example 20

Di-t-butyl-(2R)-2-pentylthioacetylamino-2-phenylethylphosphate

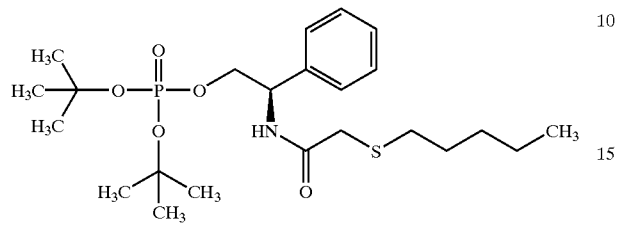

To a solution of the compound prepared in Reference example 6(281 mg) in benzene (2 ml) was added sodium hydride (60% dispersion in mineral oil)(80 mg) and the mixture was refluxed for 30 minutes. The reaction mixture was cooled to room temperature. To the mixture was added a solution of di-tbutyl phosphorobromidate (272 mg) in tetrahydrofuran (2 ml) and the mixture was stirred for 2 hours at 30° C. The reactio mixture was diluted with ethyl acetate and washed with a saturated aqueous solution of sodium bicarbonate and a saturated aqueous solution of sodium chloride, successively, dried and concentarated to give the compound (400 mg) of the present invention having the following physical data.

TLC: Rf 0.16(Hexane:Ethyl acetate=1:1).

Example 21

(2R)-2-Pentylthioacetylamino-2-phenylethylphosphate

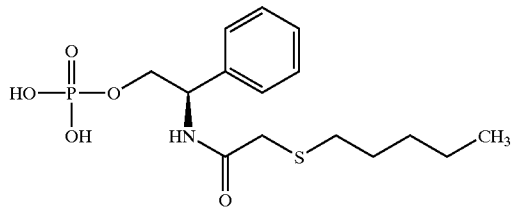

To a solution of the compound prepared in Example 20 (400 mg) in benzene (5 ml) was added trifluoroacetic acid (1 ml) and the mixture was stirred for 15 hours at room temperature. The reaction mixture was concentated. To the residue were added methylene chloride (5 ml) and 2N aqueous solution of sodium hydroxide (5 ml) and then extracted. The extracted aqueous layer was washed with methylene chloride (three times). To the aqueous layer was added 2N hydrochloric acid (10 ml) and then extracted with ethyl acetate. The organic layer was dried over anhydrous magnesium sulfate and concentrated to give the compound (284 mg) of the present invention having the following physical data.

TLC: Rf 0.35(Chloroform:Methanol:Water=65:35:8).

Example 22

(2R)-2-Pentylthioacetylamino-2-phenylethylphosphate Disodium Salt

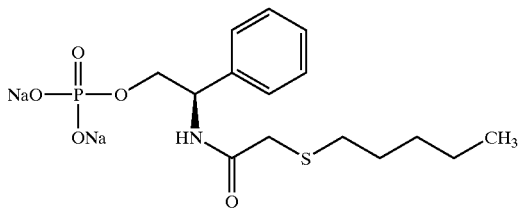

The compound of the present invention having the following physical data was obtained by the same procedure as Example 8, using the compound prepared in Example 21.

TLC: Rf 0.35(Chloroform:Methanol:Water=65:35:8);

NMR(CD$_3$OD): $\delta$7.37(brd, J=7.5 Hz, 2H), 7.26(brt, J=7.5 Hz, 2H), 7.18(m, 1H), 4.92(dd, J=8.1, 4.5 Hz, 1H), 3.97(m, 2H), 3.36(d, J=13.8 Hz, 1H), 3.13(d, J=13.8 Hz, 1H), 2.52(brt, J=7.2 Hz, 2H), 1.54(m, 2H), 1.30(m, 4H), 0.87(brt, J=7.2 Hz, 3H).

Example 22(1)~Example 22(7)

The compounds of the present invention having the following physical data were obtained by the same procedure as a series of reactions of Reference example 3→Example 20→Example 21→Example 22, using corresponding carboxylic acid instead of 5-phenylpentanoic acid and corresponding aminoalcohol instead of (2R)-2-amino-2-phenylethanol.

Example 22(1)

2-(4-Chlorophenyl)-2-octanoylaminoethylphosphate Disodium Salt

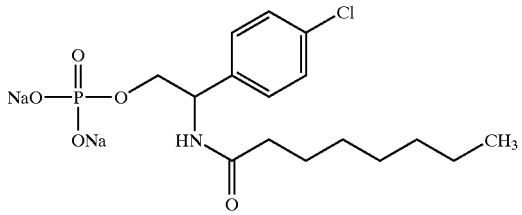

TLC: Rf 0.39(Chloroform:Methanol:Water=65:35:8);

NMR(CD$_3$OD): $\delta$7.36–7.33(m, 2H), 7.31–7.27(m, 2H), 5.05–5.01(m, 1H), 4.08–3.93(m, 2H), 2.28–2.23(m, 2H), 1.64–1.57(m, 2H), 1.30–1.27(m, 8H), 0.91–0.86(m, 3H).

Example 22(2)

(1S,2R)-1-Methyl-2-(2-pentylthioacetyl)amino-2-phenylethylphosphate Disodium Salt

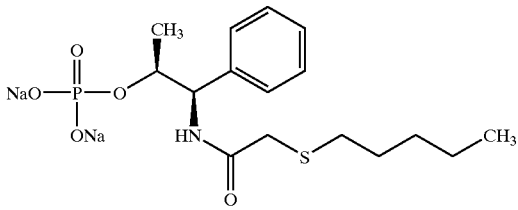

TLC: Rf 0.25(Chloroform:Methanol:Water=65:25:4);

NMR(CD$_3$OD): δ7.45(brd, J=7.2 Hz, 2H), 7.26–7.15(m, 3H), 4.65(m, 1H), 4.60(m, 1H), 3.33(d, J=13.8 Hz, 1H), 3.16(d, J=13.8 Hz, 1H), 2.48(brt, J=7.2 Hz, 2H), 1.47(m, 2H), 1.30–1.20(m, 4H), 1.03(d, J=6.6 Hz, 3H), 0.85(brt, J=7.2 Hz, 3H).

Example 22(3)

2-(3-Chlorophenyl)-2-octanoylaminoethylphosphate Disodium Salt

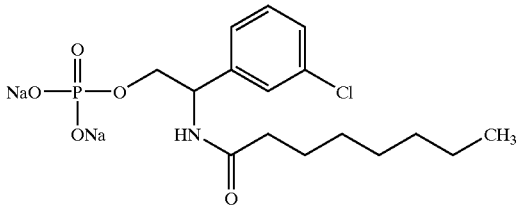

TLC: Rf 0.33(Chloroform:Methanol:Water=65:35:8);

NMR(CD$_3$OD): δ7.37(s, 1H), 7.30–7.20(m, 3H), 5.02(dd, J=6.9, 4.2 Hz, 1H), 4.10–3.90(m, 2H), 2.35–2.13(m, 2H), 1.70–1.55(m, 2H), 1.40–1.10(m, 8H), 0.88(t, J=6.6 Hz, 3H).

Example 22(4)

2-(2-Chlorophenyl)-2-octanoylaminoethylphosphate Disodium Salt

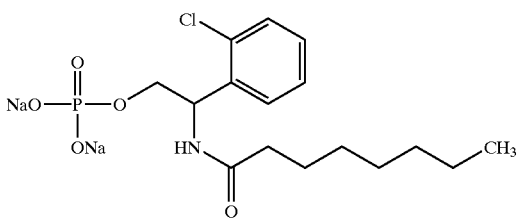

TLC: Rf 0.26(Chloroform:Methanol:Water=65:35:8);

NMR(CD$_3$OD): δ7.46–7.42(m, 1H), 7.38–7.33(m, 1H), 7.29–7.20(m, 2H), 5.44(dd, J=7.0 Hz, 4.0 Hz, 1H), 4.15–3.90(m, 2H), 2.32–2.24(m, 2H), 1.65–1.54(m, 2H), 1.36–1.22(m, 8H), 0.88(t, J=7.0 Hz, 3H).

Example 22(5)

2-(3-Methylthiophenyl)-2-octanoylaminoethylphosphate Disodium Salt

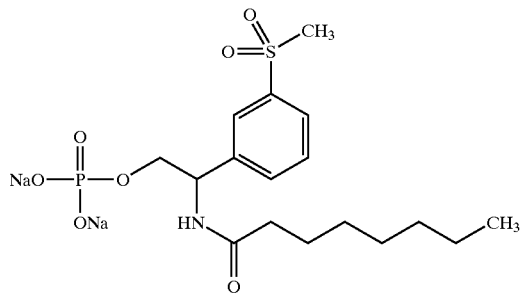

TLC: Rf 0.37(Chloroform:Methanol:Water=65:35:8);

NMR(CD$_3$OD): δ7.25(m, 1H), 7.18(d, J=6.8 Hz, 1H), 7.14–7.07(m, 2H), 4.89–4.83(m, 1H), 4.04–3.85(m, 2H), 2.45(s, 3H), 2.42–2.16(m, 2H), 1.68–1.52(m, 2H), 1.35–1.24(m, 8H), 0.92–0.84(m, 3H).

Example 22(6)

2-(3-Methylsulfonylphenyl)-2-octanoylaminoethylphosphate Disodium Salt

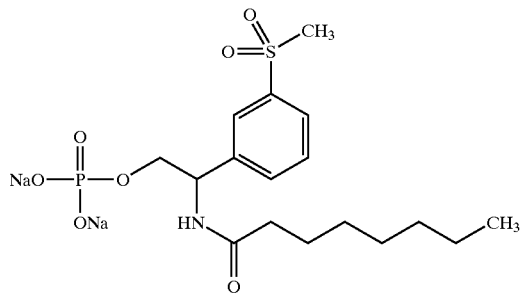

TLC: Rf 0.31(Chloroform:Methanol:Water=65:35:8);

NMR(CD$_3$OD): δ7.95(brs, 1H), 7.80(brd, J=7.8 Hz, 1H), 7.74(brd, J=7.8 Hz, 1H), 7.55(t, J=7.8 Hz, 1H), 5.00–4.95 (m, 1H), 4.14–3.89(m, 2H), 3.10(s, 3H), 2.43–2.18(m, 2H), 1.68–1.52(m, 2H), 1.36–1.22(m, 8H), 0.93–0.84(m, 3H).

Example 22(7)

2-(3-Isopropylthiophenyl)-2-octanoylaminoethylphosphate Disodium Salt

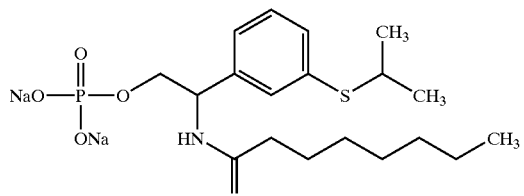

TLC: Rf 0.27(Chloroform:Methanol:Water=65:25:4);

NMR(CD$_3$OD): δ7.36(brs, 1H), 7.22(m, 3H), 4.84(m, 1H), 4.00–3.90(m, 2H), 3.37(m, 1H), 2.41–2.17(m, 2H), 1.70–1.50(m, 2H), 1.40–1.20(m, 8H), 1.24(d, J=6.6 Hz, 6H), 0.88(brt, J=6.6 Hz, 3H).

Reference Example 7 bis(2-Cyanoethoxy)(diisopropylamino)phosphine

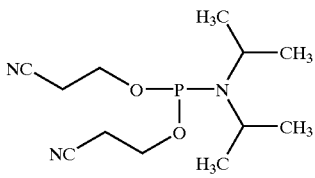

To a solution of 2-cyanoethyl-N,N,N',N'-tetraisopropyl phosphorodiamide (5.0 g) in methylene chloride (80 ml) was added a solution of diisopropylamine tetrazole salt (1.42 g) and ethylene cyanohydrine (1.30 g) in methylene chloride (10 ml) at room temperature and the mixture was stirred for 90 minutes. The reaction mixture was poured into a saturated aqueous solution of sodium bicarbonate. The mixture was extracted with methylene chloride, dried over anhydrous sodium sulfate and concentrated. The residue was purified by column chromatography on silica gel (hexane:ethyl acetate=3:1) to give the title compound (2.30 g) having the following physical data.

TLC: Rf 0.73(Hexane:Ethyl acetate=1:1);

NMR(CDCl$_3$): δ4.00–3.75(m, 4H), 3.75–3.50(m, 2H), 2.66(td, J=6.4, 0.7 Hz, 4H), 1.20(d, J=6.6 Hz, 12H).

Reference Example 8

(2R)-2-Octanoylamino-2-phenylethoxybis(2-cyanoethoxy)phosphine

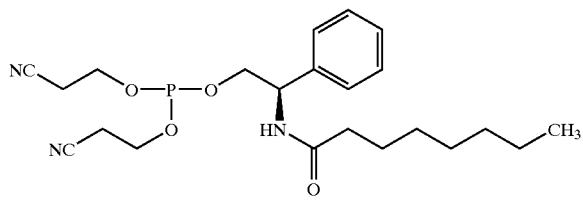

To a solution of (2R)-2-octanoylamino-2-phenylethanol (789 mg) in acetonitrile (8 ml) was added tetrazole (420 mg) and the compound prepared in Reference example 7 (1.14 g) and the mixture was stirred for 1 hour at room temperature. The reaction mixture was poured into a saturated aqueous solution of sodium bicarbonate. The mixure was extracted with ethyl acetate, washed with a saturated aqueous solution of sodium chloride. The organic layer was dried over anhydrous sodium sulfate and then concentrated. The residue was purified by column chromatography on silica gel (hexane:ethyl acetate=1:1) to give the title compound (1.20 g) having the following physical data.

TLC: Rf 0.22(Hexane:Ethyl acetate=1:1);

NMR(CDCl$_3$): δ7.45–7.20(m, 5H), 6.24(d, J=8.4 Hz, 1H), 5.28(td, J=8.4, 4.8 Hz, 1H), 4.20–4.05(m, 2H), 4.05–3.80(m, 4H), 2.57(t, J=6.0 Hz, 4H), 2.25(t, J=7.4 Hz, 2H), 1.75–1.50(m, 2H), 1.40–1.15(m, 8H), 0.88(t, J=6.6 Hz, 3H).

Example 23

(2R)-Bis(2-cyanoethyl)-2-octanoylamino-2-phenylethylthiophosphate

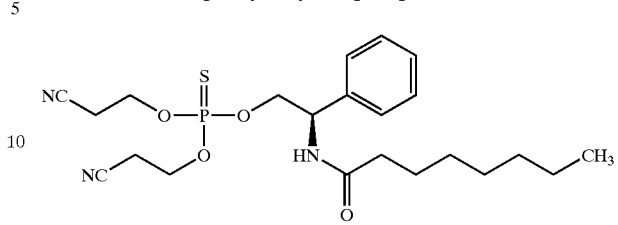

To a solution of the compound prepared in Reference example 8 (1.16 g) in acetonitrile (11 ml) was added 3H-1,2-benzodithiol-3-one 1,1-dioxide (590 mg), the mixture was stirred for 1 hour at room temperature. The reaction mixture was concentrated. The residue was purified by column chromatography on silica gel (hexane:ethyl acetate=1:1) to give the compound (797 mg) of the present invention having the following physical data.

TLC: Rf 0.24(Hexane:Ethyl acetate=1:1);

NMR(CDCl$_3$): δ7.50–7.22(m, 5H), 6.28(d, J=8.4 Hz, 1H), 5.40–5.30(m, 1H), 4.40–4.26(m, 2H), 4.26–4.00(m, 4H), 2.75–2.60(m, 4H), 2.26(t, J=7.5 Hz, 2H), 1.78–1.50(m, 2H), 1.50–1.18(m, 8H), 0.88(t, J=6.6 Hz, 3H).

Example 24

(2R)-2-Octanoylamino-2-phenylethylthiophosphoric acid

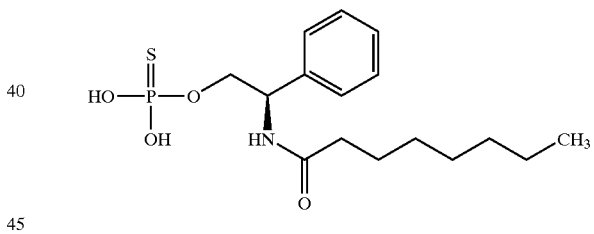

To a solution of the compound prepared in Example 23 (736 mg) in ethanol (10 ml) was added 50% aqueous solution of dimethylamine (10 ml). The mixture was stirred for 12 hours at 50° C. The reaction mixture was concentrated. To the residue was added 1N hydrochloric acid and the mixture was extracted with ethyl acetate. To the organic layer was added 2N aqueous solution of sodium hydroxide and the aqueous layer was washed with methylene chloride. The aqueous layer was acidified by adding 2N hydrochloric acid and then extracted with ethyl acetate. The organic layer was washed with a saturated aqueous solution of sodium chloride, dried over anhydrous sodium sulfate and concentared. The residue was solidified by adding hexane to give the compound (473 mg) of the present invention having the following physical data.

TLC: Rf 0.35(Chloroform:Methanol:Water=65:35:8);

NMR(CD$_3$OD): δ7.40–7.22(m, 5H), 5.19(dd, J=7.7, 5.0 Hz, 1H), 4.25–4.05(m, 2H), 2.27(t, J=7.4 Hz, 2H), 1.70–1.55 (m, 2H), 1.40–1.20(m, 8H), 0.89(t, J=6.8 Hz, 3H).

Example 25

(2R)-2-Octanoylamino-2-phenylethylthiophosphoric Acid Disodium Salt

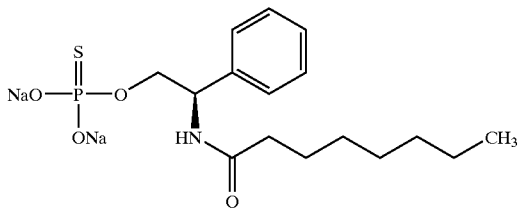

The compound of the present invention having the following physical data was obtained by the same procedure as Example 8, using the compound (458 mg) prepared in Example 23.

TLC: Rf 0.35(Chloroform:Methanol:Water=65:35:8);

NMR(CD$_3$OD): δ7.35(d, J=7.2 Hz, 2H), 7.27(dd, J=7.2, 7.2 Hz, 2H), 7.19(t, J=7.2 Hz, 1H), 4.92(t, J=6.3 Hz, 1H), 4.06(dd, J=7.8, 6.3 Hz, 2H), 2.40–2.20(m, 2H), 1.70–1.50 (m, 2H), 1.40–1.20(m, 8H), 0.89(t, J=6.6 Hz, 3H).

Reference Example 9

(1S,2R)-[Bis(2-cyanoethoxy)]-1,2-diphenyl-2-octanoylaminoethoxyphosphite

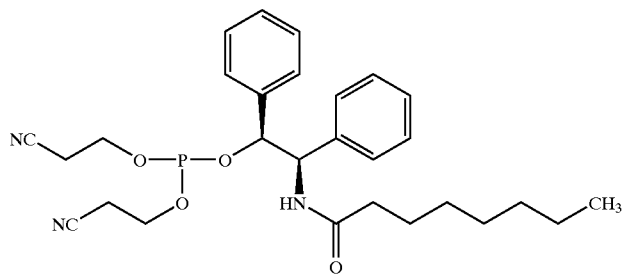

The title compound having the following physical data was obtained by the same procedure as a series of reactions of Reference example 3→Reference example 8, using (1S, 2R)-2-amino-1,2-diphenylethanol instead of (2R)-2-amino-2-phenylethanol.

TLC: Rf 0.43(Hexane:Ethyl acetate=1:1).

Example 26

(1S,2R)-[Bis(2-cyanoethyl)]-1,2-diphenyl-2-octanoylaminoethylphosphate

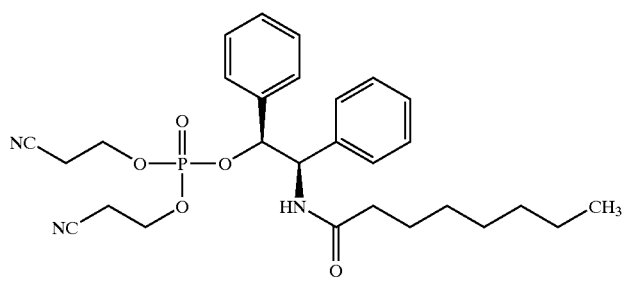

To a solution of the compound prepared in Reference example 9 (1.15 g) in methylene chloride (30 ml) was added 3-chloroperbenzoic acid (ca. 57% purity; 685 mg) under cooling with ice, and the mixture was stirred for 30 minutes at 0° C. To the reaction mixture was added a saturated aqueous solution of sodium thiosulfate and the mixture was extracted with ethyl acetate. After passing the organic layer through a column of alumina, the eluent was washed with a saturated aqueous solution of sodium bicarbonate, water and a saturated aqueous solution of sodium chloride, successively, dried over anhydrous sodium sulfate and then concentrated to give the title compound (1.0 g) having the following physical data.

TLC: Rf 0.20(Methylene chloride:Ethyl acetate=1:1).

Example 27

(1S,2R)-2-Octanoylamino-1,2-diphenylethylphosphate Disodium Salt

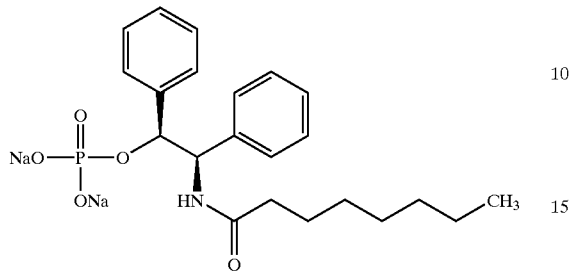

The compound of the present invention having the following physical data was obtained by the same procedure as a series of reactions of Example 24 Example 8, using the compound prepared in Example 26.

TLC: Rf 0.41(Chloroform:Methanol:Water=65 25 4);

NMR(CD$_3$OD): δ7.20–7.05(m)and 7.00(m)total 10H, 5.68(dd, J=10.2, 2.4 Hz, 1H), 4.96(d, J=2.4 Hz, 1H), 2.40–2.30(m, 2H), 1.65–1.55(m, 2H), 1.40–1.20(m, 8H), 0.88(t, J=6.3 Hz, 3H).

Reference Example 10

Bis(2-cyanoethoxy)-2-octanoylamino-2-(3-benzyloxyphenyl)ethoxyphosphite

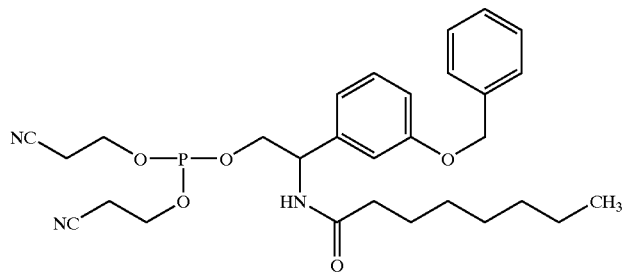

The title compound having the following physical data was obtained by the same procedure as a series of reactions of Reference example 3→ Reference example 8, using 2-(3-benzyloxyphenyl)aminoethanol instead of (1S,2R)-2-amino-1,2-diphenylethanol.

TLC: Rf 0.75(Hexane:Ethyl acetate=1:3).

Example 28

2-Octanoylamino-2-(3-benzyloxyphenyl)ethylphosphate Disodium Salt

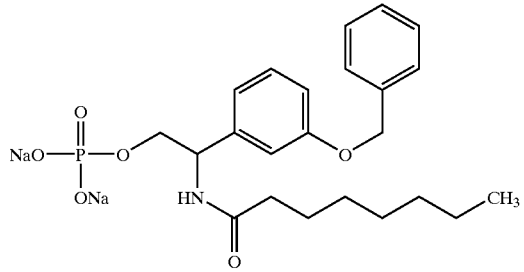

The compound of the present invention having the following physical data was obtained by the same procedure as a series of reactions of Example 26→Example24→Example 8, using the compound prepared in Reference example 10.

TLC: Rf 0.44(Chloroform:Methanol:Water=65:35:8);

NMR(CD$_3$OD): δ7.46–7.26(m, 5H), 7.18(t, J=7.5 Hz, 1H), 7.01(m, 1H), 6.94(d, J=7.5 Hz, 1H), 6.82(m, 1H), 5.08(d, J=12 Hz, 1H), 5.03(d, J=12 Hz, 1H), 4.95–4.80(m, 1H), 4.03–3.88(m, 2H), 2.40–2.18(m, 2H), 1.65–1.48(m, 2H), 1.40–1.20(m, 8H), 0.86(brt, J=6.9 Hz, 3H).

Reference Example 11

(2R)-2-t-Butoxycarbonylamino-2-phenyl-1-iodoethane

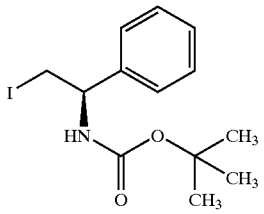

To a solution of the compound prepared in Reference example 1 (3.0 g) in a mixture of diethyl ether (60 ml) and acetonitrile (20 ml) were added imidazole (1.2 g) and iodine (4.16 g) at 0° C. and the mixture was stirred for 4 hours at 0° C. The reaction mixture was poured inth water and the mixture was extracted with diethyl ether. The organic layer was washed with a saturated aqueous solution of sodium thiosulfate, water and a saturated aqueous solution of sodium chloride, successively, dried over anhydrous magnesium sulfate and concentrated. The residue was purified by column chromatography on silica gel (hexane:ethyl acetate=5:1) to give the title compound (3.4 g) having the following physical data.

TLC: Rf 0.65(Hexane:Ethyl acetate=3:1);

NMR(CDCl$_3$): δ7.40–7.23(m, 5H), 5.04(br, 1H), 4.86–4.50(m, 1H), 3.60–3.43(m, 2H), 1.44(s, 9H).

Reference Example 12

(2R)-S-(2-t-Butoxycarbonylamino-2-phenyl)ethyl-1-acetothioate

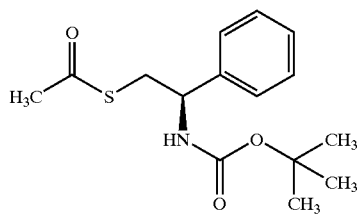

To a solution of the compound prepared in Reference example 11 (3.40 g) in acetone (50 ml) was added potassium thioacetate (1.68 g) and the mixture was refluxed for 30 minutes. After the cooling to room temperature the reaction mixture was extracted with ethyl acetate. The organic layer was washed with water and a saturated aqueous solution of sodium chloride, dried over anhydrous magnesium sulfate and then concentrated to give the title compound (2.86 g) having the following physical data.

TLC: Rf 0.45(Hexane:Ethyl acetate=3:1);

NMR(CDCl$_3$): δ7.40–7.23(m, 5H), 5.07(br, 1H), 4.83(br, 1H), 3.34–3.14(m, 2H), 2.35(s, 3H), 1.41(s, 9H).

Reference Example 13

(2R)-2-t-Butoxycarbonylamino-2-phenylethanethiol

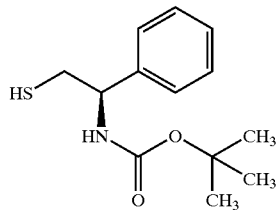

To a solution of the compound prepared in Reference example 12 (1.05 g) in a mixture of methanol (25 ml) and dioxane (15 ml) was added potassium carbonate (983 mg) and the mixture was stirred for 30 minutes at room temperature. The reaction mixture was filtered and the filtrate was concentrated to give the title compound (900 mg) having the following physical data.

TLC: Rf 0.80(Hexane:Ethyl acetate=3:1);

NMR(CDCl$_3$): δ7.40–7.23(m, 5H), 5.20(br, 1H), 4.90(br, 1H), 3.05–2.83(m, 2H), 1.44(s, 9H), 1.17(t, J=8.1 Hz, 1H).

Example 29

Diethyl-(2R)-S-(2-t-butoxycarbonylamino-2-phenyl)ethanephosphorothioate

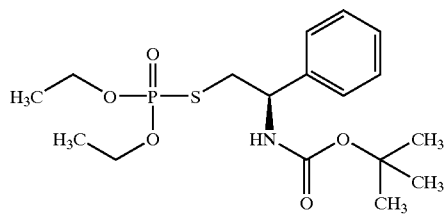

To a solution of the compound prepared in Reference example 13 (900 mg) in pyridine (15 ml) were added dimethylaminopyridine (869 mg) and diethyl chlorophosphate (924 mg) and the mixture was stirred for 2 days at room temperature. The reaction mixture was poured into 1N hydrochloric acid and the mixture was extracted with ethyl acetate. The organic layer was washed with water and a saturated aqueous solution of sodium chloride, successively, dried over anhydrous magnesium sulfate and concentrated. The residue was purified by column chromatography on silica gel (hexane:ethyl acetate=3:1) to give the compound (300 mg) of the present invention having the following physical data.

TLC: Rf 0.55(Hexane:Ethyl acetate=3:1);

NMR(CDCl$_3$): δ7.40–7.23(m, 5H), 5.83(br, 1H), 4.83(br, 1H), 4.30–4.03(m, 4H), 3.18(dd, J=15, 7.5 Hz, 2H), 1.40(s) and 1.35(m)total 15H.

Example 30

(2R)-S-(2-Octanoylamino-2-phenylethyl)-O,O'-diethylphosphorothioate

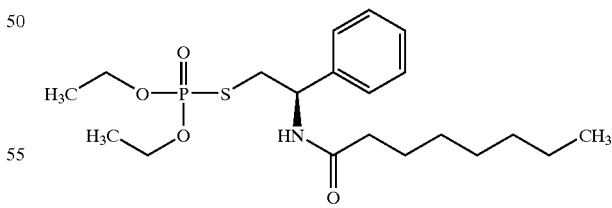

The compound of the present invention having the following physical data was obtained by the same procedure as a series of reactions of Reference example 2 Example 2, using the compound prepared in Example 29 instead of the compound prepared in Example 1.

TLC: Rf 0.43(Hexane:Ethyl acetate=1:1).

Example 31

(2R)-S-(2-Octanoylamino-2-phenylethyl)phosphorothioate

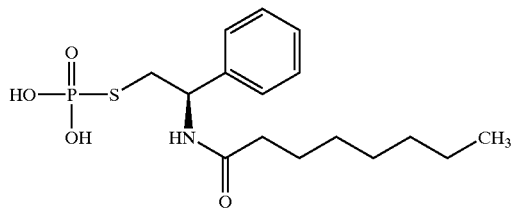

To a solution of the compound prepared in Example 30 (280 mg) in chloroform (2 ml) was added bromotrimethylsilane (0.35 ml) and the mixture was stirred overnight at room temperature. The reaction mixture was concentrated. To the residue was added 1N aqueous solution of sodium hydroxide and the mixture was extracted with ethyl acetate. The aqueous layer was acidified by adding 1N hydrochloric acid and extracted with ethyl acetate. The organic layer was washed with water and a saturated aqueous solution of sodium chloride, successively, dried over anhydrous sodium sulfate and concentrated to give the compound (157 mg) of the present invention having the following physical data.

TLC: Rf 0.23(Chloroform:Methanol:Water 65:25:4);

NMR(CD$_3$OD) δ7.40–7.20(m, 5H), 5.12(dd, J=9.2, 5.6 Hz, 1H), 3.24–3.00(m, 2H), 2.56(t, J=7.4 Hz, 2H), 1.61(m, 2H), 1.44–1.20(m, 8H), 0.89(m, 3H).

Example 32

(2R)-S-(2-Octanoylamino-2-phenylethyl)phosphorothioate Disodium Salt

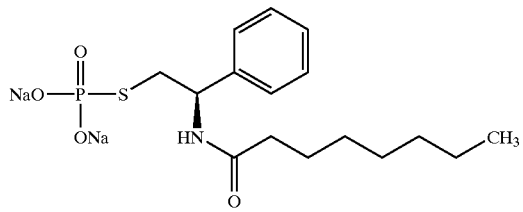

The compound of the present invention having the following physical data was obtained by the same procedure as Example 8, using the compound prepared in Example 31 instead of the compound prepared in Example 7.

TLC: Rf 0.23(Chloroform:Methanol:Water=65:25:4);

NMR(CD$_3$OD): δ7.38–7.10(m, 5H), 4.90–4.70(m, 1H), 3.20–2.98(m, 2H), 2.50–2.10(m, 2H), 1.59(m, 2H), 1.40–1.10(m, 8H), 0.89(t, J=6.3 Hz, 3H).

Example 33

2-(3-Hydroxyphenyl)-2-octanoylaminoethylphosphate Disodium Salt

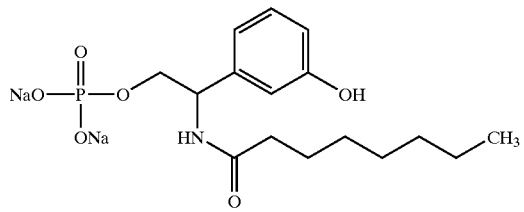

To a solution of the salt-free compound prepared in Example 19(43) (460 mg) in methanol (10 ml) was added 6N hydrochloric acid to adjust to pH 1 and the mixture was stirred overnight at room temperature. The reaction mixture was poured into water and then extracted with ethyl acetate. The organic layer was washed with a saturated aqueous solution of sodium chloride, dried over anhydrous magnesium sulfate and concentrated. To a solution of the residue in ethanol (10 ml) was added 1 N aqueous solution of sodium hydroxide (1.61 ml) and the mixture was stirred for 10 minutes at room temperature and then concentrated. To the residue was added ethanol and then the mixture was concentrated to give the compound (325 mg) of the present invention having the following physical data.

TLC: Rf 0.22(Chloroform:Methanol:Water=65:35:8);

NMR(CD$_3$OD): δ7.04(t, J=7.8 Hz, 1H), 6.78(brs, 1H), 6.74(brd, J=7.8 Hz, 1H), 6.59(dd, J=7.8, 2.4 Hz, 1H), 4.82(dd, J=8.1, 3.9 Hz, 1H), 4.00–3.86(m, 2H), 2.36–2.18 (m, 2H), 1.68–1.53(m, 2H), 1.35–1.24(m, 8H), 0.91–0.86 (m, 3H).

Example 34

2-(3-Hydroxymethylphenyl)-2-octanoylaminoethylphosphate Disodium Salt

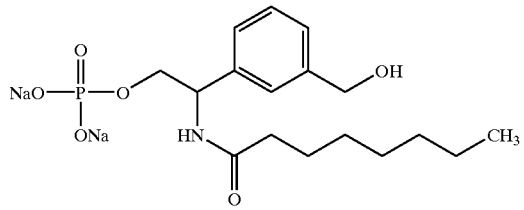

The compound of the present invention having the following physical data was obtained by the same procedure as a series of reactions of Reference example 3→Reference example 8→Example 26→Example 24→Example 33, using 2-amino-2-(3-methoxymethoxymethylphenyl)ethanol instead of (2R)-2-amino-2-phenylethanol.

TLC: Rf 0.30(Chloroform:Methanol:Water=65:35:8);

NMR(CD$_3$OD): δ7.34(brs, 1H), 7.25–7.18(m, 3H), 4.90–4.87(m, 1H), 4.56(s, 2H), 4.03–3.88(m, 2H), 2.37–2.19(m, 2H), 1.65–1.53(m, 2H), 1.34–1.25(m, 8H), 0.91–0.86(m, 3H).

Example 34(1)

(1S,2R)-2-(3-Hydroxymethylphenyl)-1-methyl-2-octanoylaminoethylphosphate Disodium Salt

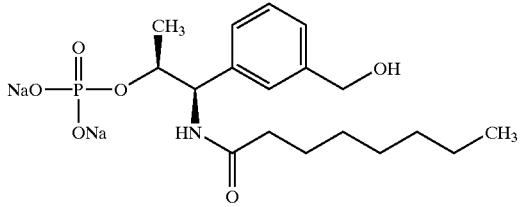

The compound of the present invention having the following physical data was obtained by the same procedure as Example 34, using (1S,2R)-2-amino-1-methyl-2-(3-methoxymethoxymethylphenyl)ethanol instead of (2R)-2-amino-2-(3-methoxymethoxymethylphenyl)ethanol.

TLC: Rf 0.26(Chloroform:Methanol:Water=65:35:8);

NMR(CD$_3$OD): δ7.45(brs, 1H), 7.31(dt, J=7.2, 1.5 Hz, 1H), 7.24–7.16(m, 2H), 4.62–4.53(m, 4H), 2.29–2.23(m, 2H), 1.60–1.48(m, 2H), 1.32–1.22(m, 8H), 1.04(d, J=6.6 Hz, 3H), 0.89–0.84(m, 3H).

Reference Example 14

Bis(benzyloxy)-2-(3-ethoxycarbonylmethoxyphenyl)-2-octanoylaminoethoxyphosphine

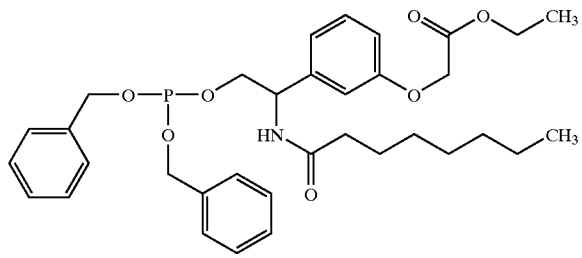

The title compound having the following physical data was obtained by the same procedure as Reference example 8, using 2-octanoylamino-2-(3-ethoxycarbonylmethoxyphenyl)ethanol instead of (2R)-2-octanoylamino-2-phenylethanol and dibenzyloxydiisopropylaminophosphine instead of the compound prepared in Reference example 7.

TLC: Rf 0.65(Hexane:Ethyl acetate=1:1).

Example 35

2-(3-Ethoxycarbonylmethoxyphenyl)-2-octanoylaminoethylphosphate

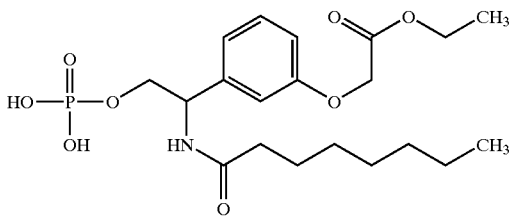

The compound of the present invention having the following physical data was obtained by the same procedure as a series of reactions of Example 26→Example 11, using the compound prepared in Reference example 14.

TLC: Rf 0.50(Chloroform:Methanol:Water=65:35:8).

Example 36

2-(3-Ethoxycarbonylmethoxyphenyl)-2-octanoylaminoethylphosphate Disodium Salt

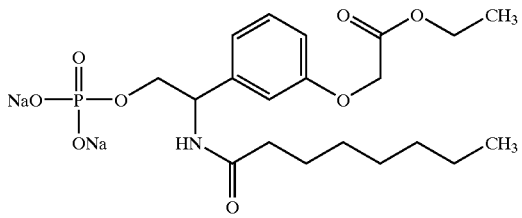

The compound of the present invention having the following physical data was obtained by the same procedure as a series of reactions of Example 8, using the compound prepared in Example 35 (390 mg) and 1M aqueous solution of sodium bicarbonate (1.74 ml) instead of 1N aqueous solution of sodium hydroxide.

TLC: Rf 0.50(Chloroform:Methanol:Water=65:35:8);

NMR(CD$_3$OD): δ7.19(t, J=7.8 Hz, 1H), 6.98(d, J=7.8 Hz, 1H), 6.94(t, J=2.1 Hz, 1H), 6.76(m, 1H), 4.85–4.83(m, 1H), 4.67(s, 2H), 4.24(q, J=7.2 Hz, 2H), 4.04–3.86(m, 2H), 2.40–2.18(m, 2H), 1.65–1.55(m, 2H), 1.40–1.20(m)and 1.28 (t, J=7.2 Hz)total 11H, 0.89(brt, J=6.9 Hz, 3H).

Example 36(1)–Example 36(6)

The compounds of the present invention having the following physical data were obtained by the same procedure as a series of reactions of Reference example 3→Reference example 14→Example 35→Example 36, using corresponding aminoalcohol instead of (2R)-2-amino-2-phenylethanol and corresponding carboxylic acid instead of 5-phenylpentanoic acid.

Example 36(1)

(1S,2R)-2-(3-Methoxycarbonylphenyl)-1-methyl-2-octanoylaminoethylphosphate Disodium Salt

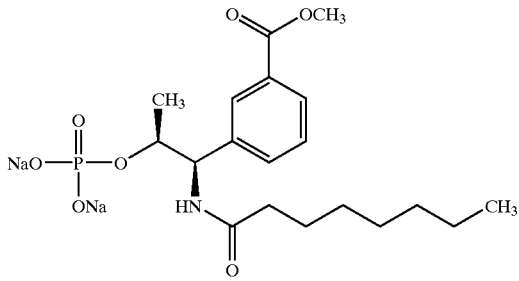

TLC: Rf 0.30(Chloroform:Methanol:Water=65:35:8);

NMR(CD$_3$OD): δ8.03(brs, 1H), 7.86(brd, J=7.8 Hz, 1H), 7.75(brd, J=7.8 Hz, 1H), 7.38(t, J 7.8 Hz, 1H), 4.69–4.60(m, 2H), 3.88(s, 3H), 2.35–2.19(m, 2H), 1.60–1.48(m, 2H), 1.32–1.16(m, 8H), 1.04(d, J=6.3 Hz, 3H), 0.88–0.83(m, 3H).

Example 36(2)

2-(3-Methoxycarbonylmethylphenyl)-2-octanoylaminoethylphosphate Disodium Salt

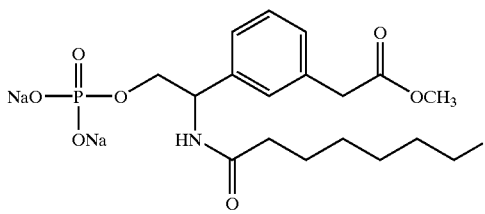

TLC: Rf 0.42(Chloroform:Methanol:Water=65:35:8);

NMR(CD$_3$OD): δ7.25–7.19(m, 3H), 7.13–7.10(m, 1H), 4.90–4.85(m, 1H), 4.02–3.87(m, 2H), 3.65(s, 3H), 3.60(s, 2H), 2.37–2.18(m, 2H), 1.63–1.55(m, 2H), 1.37–1.25(m, 8H), 0.88(t, J=6.9 Hz, 3H).

Example 36(3)

2-(3-Methoxyphenyl)-1,1-dimethyl-2-octanoylaminoethylphosphate Disodium Salt

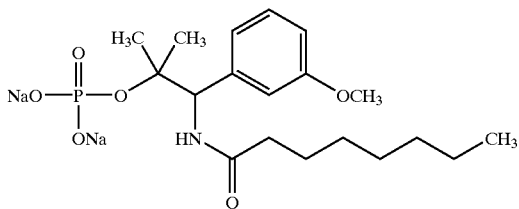

TLC: Rf 0.31 (Chloroform:Methanol:Water=65:25:4);

NMR(CD$_3$OD): δ7.13(t, J=7.8 Hz, 1H), 7.09–7.05(m, 2H), 6.73–6.69(m, 1H), 4.49(d, J=1.5 Hz, 1H), 3.78(s, 3H), 2.27(t, J=7.2 Hz, 2H), 1.66(s, 3H), 1.62–1.53(m, 2H), 1.32–1.23(m, 8H), 1.16(s, 3H), 0.86(t, J=6.3 Hz, 3H).

Example 36(4)

2-(3-Methylsulfonylaminophenyl)-2-octanoylaminoethylphosphate Trisodium Salt

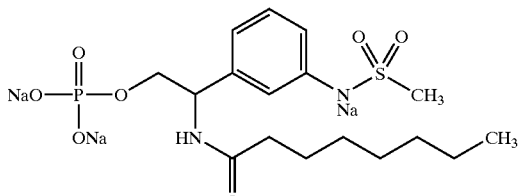

TLC: Rf 0.29(Chloroform:Methanol:Water=65:35:8);

NMR(CD$_3$OD): δ7.08(brs, 1H), 7.05(t, J=7.5 Hz, 1H), 6.93(brd, J=7.5 Hz, 1H), 6.79(brd, J=7.5 Hz, 1H), 4.84–4.81(m, 1H), 4.00–3.87(m, 2H), 2.79(s, 3H), 2.36–2.18(m, 2H), 1.66–1.54(m, 2H), 1.35–1.25(m, 8H), 0.91–0.86(m, 3H).

Example 36(5)

(1S,2R)-2-(3-Methoxycarbonylmethylphenyl)-1-methyl-2-octanoylaminoethylphosphate Disodium Salt

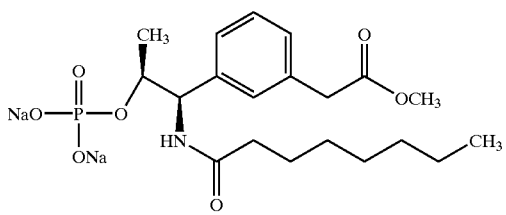

TLC: Rf 0.50(Chloroform:Methanol:Water=65:35:8);

NMR(CD$_3$OD): δ7.37–7.32(m, 2H), 7.20(brt, J=7.5 Hz, 1H), 7.11(brd, J=7.5 Hz, 1H), 4.63–4.54(m, 2H), 3.68(d, J=15.0 Hz, 1H), 3.65(s, 3H), 3.60(d, J=15.0 Hz, 1H), 2.34–2.18(m, 2H), 1.60–1.49(m, 2H), 1.34–1.20(m, 8H), 1.04(d, J=6.3 Hz, 3H), 0.89–0.84(m, 3H).

Example 36(6)

2-(3-Methoxycarbonylphenyl)-2-octanoylaminoethylphosphate Disodium Salt

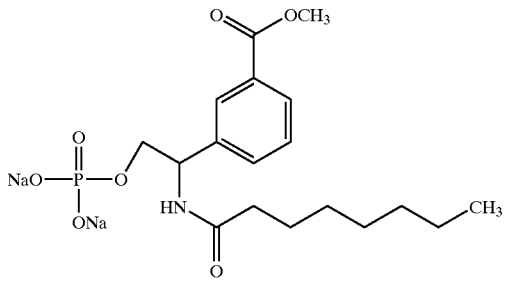

TLC: Rf 0.34(Chloroform:Methanol:Water=65:35:8);

NMR(CD$_3$OD): δ8.01(brs, 1H), 7.86(brd, J=8.1 Hz, 1H), 7.61(brd, J=8.1 Hz, 1H), 7.39(t, J=8.1 Hz, 1H), 4.94(dd, J=8.1, 3.9 Hz, 1H), 4.06–3.93(m, 2H), 3.88(s, 3H), 2.39–2.20(m, 2H), 1.66–1.53(m, 2H), 1.34–1.22(m, 8H), 0.91–0.84(m, 3H).

Reference Example 15

(1S,2R)-2-Hexyloxycarbonylamino-1-methyl-2-(3-hydroxyphenyl)ethanol

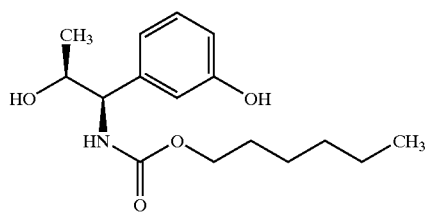

To a solution of (1R,2S)-2-hydroxy-1-(3-hydroxyphenyl)propylamine (17.2 g) in tetrahydrofuran (500 ml) was added 0.5M aqueous solution of sodium bicarbonate (500 ml) and the mixture was stirred at 0° C. To the mixture was added a solution of hexyl chloroformate (14 g) in dioxane (20 ml) and the mixture was stirred for 30 minutes at 0° C. The reaction mixture was extracted with ethyl acetate (300 ml). The organic layer was washed with a saturated aqueous solution of sodium chloride, dried over anhydrous magnesium sulfate and then concentrated. The residue was purified by column chromatography on silica gel (hexane:ethyl acetate=4:1→2:1→3:2) to give the title compound (24.2 g) having the following physical data.

TLC: Rf 0.22(Hexane:Ethyl acetate=1:1);

NMR(CDCl$_3$): δ7.16(dd, J=8.0, 8.0 Hz, 1H), 6.78–6.72 (m, 3H), 5.70(brd, J=7.4 Hz, 1H), 4.56(brs, 1H), 4.05(m, 1H), 4.00(t, J=6.6 Hz, 2H), 1.70–1.40(m, 2H), 1.40–1.20(m, 6H), 1.07(d, J=6.2 Hz, 3H), 0.87(brt, J=6.8 Hz, 3H).

Reference Example 16

(1S,2R)-2-Hexyloxycarbonylamino-1-methyl-2-(3-methoxyphenyl)ethanol

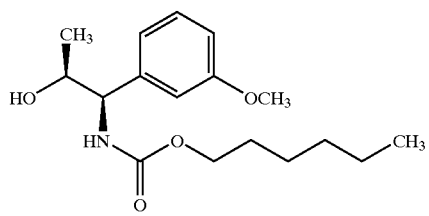

To a solution of the compound prepared in Reference example 15 (5.90 g) in N,N'-dimethylformamide (50 ml) were added potassium carbonate (6.91 g) and methyl iodide (2.0 ml) and the mixture was stirred for 13 hours at 45° C. The reaction mixture was cooled to room temperature and filterd. The filtrate was concentrated and the residue was dissolved in ethyl acetate. The solution was washed with water and a saturated aqueous solution of sodium chloride, successively, dried over anhydrous magnesium sulfate and concentrated. The residue was purified by column chromatography on silica gel (hexane:ethyl acetate=7:1→5:1→3:1) to give the title compound (4.11 g) having the following physical data.

TLC: Rf 0.33(Hexane:Ethyl acetate=1:1);

NMR(CDCl$_3$): δ7.26(dd, J=8.4, 8.4 Hz, 1H), 6.89–6.82 (m, 3H), 5.53(brd, J=7.4 Hz, 1H), 4.60(brs, 1H), 4.20–3.95 (m, 3H), 3.80(s, 3H), 1.90–1.70(m, 3H), 1.40–1.20(m, 6H), 1.10(d, J=6.0 Hz, 3H), 0.87(brt, J=6.6 Hz, 3H).

Example 37

(1S,2R)-2-Hexyloxycarbonylamino-1-methyl-2-(3-methoxyphenyl)ethylphosphate Disodium Salt

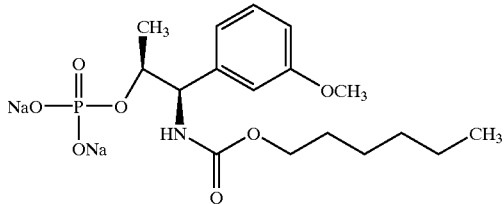

The compound of the present invention having the following physical data was obtained by the same procedure as a series of reactions of Reference example 14→Example 26→Example 11→Example 8, using the compound prepared in Reference example 16 instead of 2-octanoylamino-2-(3-ethoxycarbonylmethoxyphenyl)ethanol.

TLC: Rf 0.42(Chloroform:Methanol:Water=65:25:4);

NMR(CD$_3$OD): δ7.16(t, J=8 Hz, 1H), 7.04–6.94(m, 2H), 6.78–6.72(m, 1H), 4.68–4.54(m, 1H), 4.52(brs)and 4.40 (brs)total 1H, 3.94(t, J=6.3 Hz, 2H), 3.79(s, 3H), 1.64–1.50 (m, 2H), 1.40–1.20(m, 6H), 1.06(d, J=6.3 Hz, 3H), 0.88(m, 3H).

Example 37(1)

(1S,2R)-2-Hexyloxycarbonylamino-1-methyl-2-phenylethylphosphate Disodium Salt

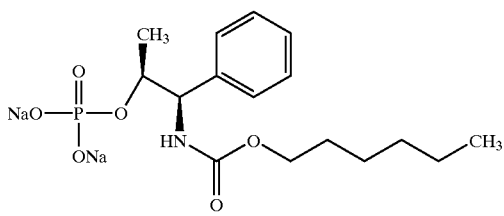

The compound of the present invention having the following physical data was obtained by the same procedure as Example 37, using (1S,2R)-2-hexyloxycarbonylamino-1-methyl-2-phenylethanol instead of the compound prepared in Reference example 16.

TLC: Rf 0.44(Chloroform:Methanol:Water=65:35:8);

NMR(CD$_3$OD): δ7.43(d, J=7.2 Hz, 2H), 7.30–7.15(m, 3H), 4.62(m, 1H), 4.50(m, 1H), 3.93(t, J=6.6 Hz, 2H), 1.58(m, 2H), 1.43–1.15(m, 6H), 1.04(d, J=6.6 Hz, 3H), 0.88(t, J=6.9 Hz, 3H).

Example 37(2)

(1S,2R)-2-Hexyloxycarbonylamino-1-methyl-2-(3-isopropyloxyphenyl)ethylphosphate Disodium Salt

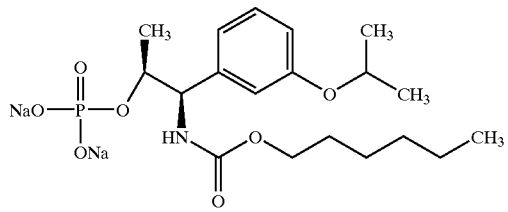

The compound of the present invention having the following physical data was obtained by the same procedure as Example 37, using (1S,2R)-2-hexyloxycarbonylamino-1-methyl-2-(3-isopropyloxyphenyl)ethanol instead of the compound prepared in Reference example 16.

TLC: Rf 0.50(Chloroform:Methanol:Water=65:35:8);

NMR(CD$_3$OD): δ7.14(t, J=7.2 Hz, 1H), 7.01–6.96(m, 2H), 6.72(dd, J=7.2 Hz, 1.8 Hz, 1H), 4.64–4.58(m, 2H), 4.50–4.37(m, 1H), 3.96–3.78(m, 2H), 1.61–1.51(m, 2H), 1.40–1.25(m, 12H), 1.06(d, J=6.3 Hz, 3H), 0.90–0.86(m, 3H).

Example 37(3)

(1S,2R)-2-Hexyloxycarbonylamino-2-(3-methoxycarbonylphenyl)-1-methylethylphosphate Disodium Salt

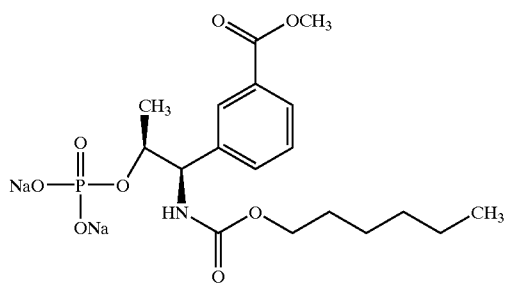

The compound of the present invention having the following physical data was obtained by the same procedure as a series of reactions of Reference example 14→Example 26→Example 11→Example 36, using (1S,2R)-2-hexyloxycarbonylamino-1-methyl-2-(3-methoxycarbonyl)phenylethanol instead of the compound prepared in Reference example 16.

TLC: Rf 0.43(Chloroform:Methanol:Water=65:35:8);

NMR(CD$_3$OD): (8.03–7.96(m, 1H), 7.87(brd, J=7.8 Hz, 1H), 7.76(brd, J=7.8 Hz, 1H), 7.39(t, J=7.8 Hz, 1H), 4.70–4.59(m, 1H), 4.56–4.47(m, 1H), 3.94–3.70(m, 2H), 3.89(s, 3H), 1.60–1.49(m, 2H), 1.37–1.22(m, 6H), 1.04(d, J=6.6 Hz, 3H), 0.91–0.78(m, 3H).

Example 38

(1S,2R)-1-Methyl-2-(3-methylthiophenyl)-2-octanoylaminoethylphosphate Disodium Salt

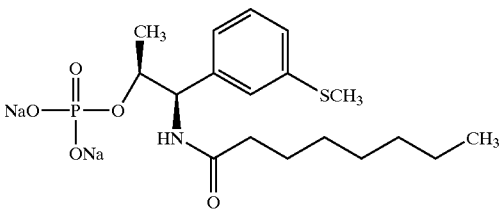

The compound of the present invention having the following physical data was obtained by the same procedure as a series of reactions of Reference example 3→Example 5→Example 7→Example 8, using (1S,2R)-2-amino-1-methyl-2-(3-methylthiophenyl)ethanol instead of (2R)-2-amino-2-phenylethanol.

TLC: Rf 0.40(Chloroform:Methanol:Water=65:25:4);

NMR(CD$_3$OD): δ7.31(brs, 1H), 7.24(brd, J=7.5 Hz, 1H), 7.17(dd, J=7.5, 7.5 Hz, 1H), 7.10(brd, J=7.5 Hz, 1H), 4.60(m, 2H), 2.46(s, 3H), 2.35–2.18(m, 2H), 1.55(m, 2H), 1.30–1.20(m, 8H), 1.05(d, J=6.3 Hz, 3H), 0.86(brt, J=6.6 Hz, 3H).

Example 39

(1S,2R)-2-Hexyloxycarbonylamino-1-methyl-2-(3-methylthiophenyl)ethylphosphate Disodium Salt

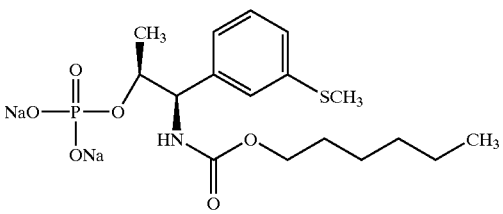

The compound of the present invention having the following physical data was obtained by the same procedure as a series of reactions of Reference example 15→Example 5→Example 7→Example 8, using (1S,2R)-2-amino-1-methyl-2-(3-methylthiophenyl)ethanol instead of (1R,2S)-2-hydroxy-1-(3-hydroxyphenyl)propylamine.

TLC: Rf 0.62(Chloroform:Methanol:Water=65:35:8);

NMR(CD$_3$OD): δ7.31–7.16(m, 3H), 7.10(dt, J=7.5 Hz, 1.8 Hz, 1H), 4.66–4.56(m, 1H), 4.4–4.37(m, 1H), 3.95–3.78(m, 2H), 2.46(s, 3H), 1.61–1.51(m, 2H), 1.39–1.23(m, 6H), 1.04(d, J=6.6 Hz, 3H), 0.88(t, J=6.9 Hz, 3H).

Reference Example 17

(2R,3R)-3-Octanoylamino-3-phenylpropan-1,2-diol

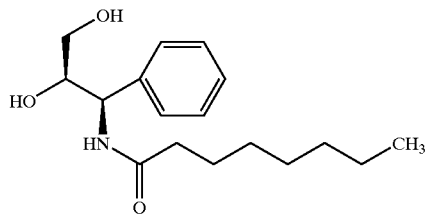

The title compound having the following physical data was obtained by the same procedure as Reference example 3, using (2R,3R)-3-amino-3-phenylpropan-1,2-diol instead of (2R)-2-amino-2-phenylethanol.

TLC: Rf 0.60(Ethyl acetate).

Reference example 18

(2R,3R)-2-Hydroxy-3-octanoylamino-3-phenylpropyl t-butyidiphenylsilyl Ether

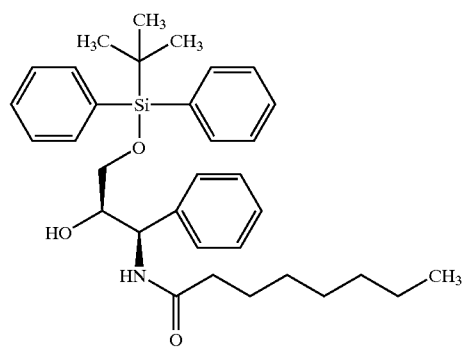

To a solution of the compound prepared in Reference example 17 (1.27 g) in dimethylformamide (20 ml) were added imidazole (589 mg) and t-butyldiphenylchlorosilane (1.43 g) and the mixture was stirred overnight. The reaction mixture was diluted with diethyl ether and then washed with a saturated aqueous solution of sodium bicarbonate, water and a saturated aqueous solution of sodium chloride, successively, dried over anhydrous sodium sulfate and then concentrated to give the title compound (2.3 g) having the following physical data.

TLC: Rf 0.35(Hexane:Ethyl acetate=2:1);

NMR(CDCl$_3$): δ7.73(m, 1H), 7.60(m, 3H), 7.45–7.30(m, 6H), 7.28–7.20(m, 5H), 6.70(d, J=8.1 Hz, 1H), 5.19(dd, J=8.1, 4.2 Hz, 1H), 3.99(dd, J=9.6, 4.2 Hz, 1H), 3.59(dd, J=10.8, 4.2 Hz, 1H), 3.48(dd, J=10.8, 5.7 Hz, 1H), 2.18(t, J=7.2 Hz, 2H), 1.60(m, 2H), 1.38–1.15(m, 8H), 1.09(s, 9H), 0.87(t, J=6.6 Hz, 3H).

Reference example 19

(1R,2R)-1-t-Butyidiphenylsilyloxymethyl-2-octanoylamino-2-phenylethylphosphate

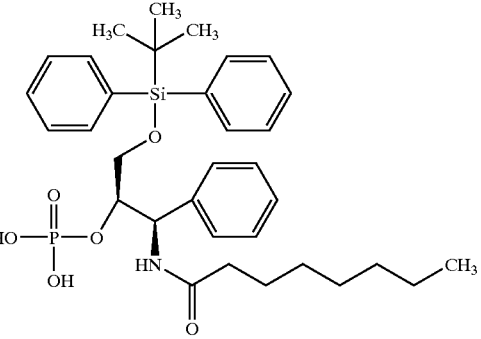

The title compound having the following physical data was obtained by the same procedure as a series of reactions of Reference example 14→Example 26→Example 11, using the compound prepared in Reference example 18 instead of 2-octanoylamino-2-(3-ethoxycarbonylmethoxyphenyl)ethanol.

TLC: Rf 0.50(Chloroform:Methanol:Water=65:25:4).

Example 40

(1 R,2R)-1-Hydroxymethyl-2-octanoylamino-2-phenylethylphosphate

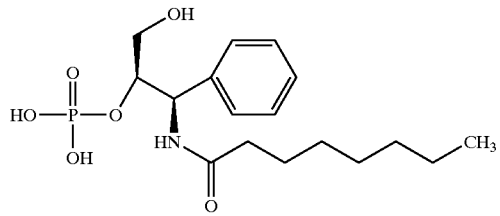

To a solution of the compound prepared in Reference example 19 (1.83 g) in tetrahydrofuran(20 ml) was added a 1M tetrabutylammonium fluoride in tetrahydrofuran (7.5 ml) and the mixture was stirred for 15 minutes. To the reaction mixture was added water and 1N aqueous solution of sodium hydroxide to adjust to pH 12, and the mixture was extracted with diethyl ether. To the aqueous layer was added 2N hydrochloric acid to adjust to pH 1, and the mixture was extracted with ethyl acetate. The combined organic layer was washed with water and a saturated aqueous solution of sodium chloride, successively, dried over anhydrous sodium sulfate and then concentrated to give the compound (700 mg) of the present invention having the following physical data.

TLC: Rf 0.23(Chloroform:Methanol:Water=65:25:4);

NMR(CD$_3$OD): δ7.42–7.20(m, 5H), 5.28(d, J=5 Hz, 1H), 4.60–4.43(m, 1H), 3.60–3.40(m, 2H), 2.28(t, J=7.5 Hz, 2H), 1.60(m, 2H), 1.40–1.20(m, 8H), 0.88(m, 3H).

Example 41

(1R,2R)-1-Hydroxymethyl-2-octanoylamino-2-phenylethylphosphate Disodium Salt

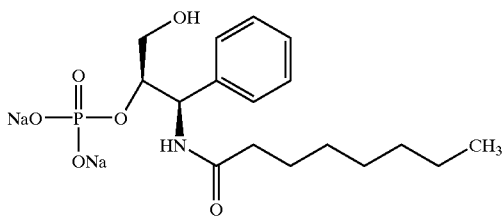

The compound of the present invention having the following physical data was obtained by the same procedure as Example 8, using the compound prepared in Example 40.

TLC: Rf 0.23 (Chloroform:Methanol:Water=65:25:4);

NMR(CD$_3$OD): δ7.44(d, J=7.2 Hz, 2H), 7.26–7.14(m, 3H), 4.93(d, J=2.7 Hz, 1H), 4.48(m, 1H), 3.38–3.25(m, 2H), 2.36–2.18(m, 2H), 1.55(m, 2H), 1.38–1.18(m, 8H), 0.86(t, J=6.3 Hz, 3H).

Example 42

2-(3-Carboxyphenyl)-2-octanoylaminoethylphosphate Trisodium Salt

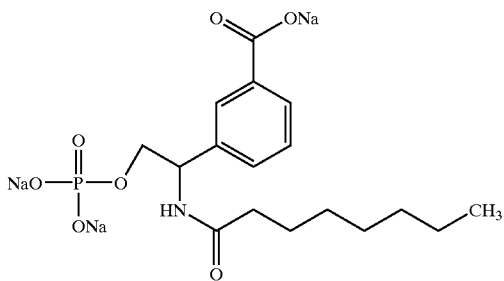

To a solution of the compound prepared in Example 36(6) (775 mg) in a mixture of ethanol (5.0 ml) and tetrahydrofuran (5.0 ml) was added 2N aqueous solution of sodium hydroxide (0.96 ml) under cooling with ice and the mixture was stirred for 3 hours at room temperature. To the mixture was added 2N hydrochloric acid and the mixture was extracted with ethyl acetate. The organic layer was washed with 1 N hydrochloric acid, water and a saturated aqueous solution of sodium chloride, successively, dried over anhydrous magnesium sulfate and then concentrated. To the residue were added ethanol and 1N aqueous solution of sodium hydroxide and the mixture was stirred for 10 minutes at room temperature and then concentrated. To the reaction mixture was added ethanol and then concentrated to give the compound (750 mg) of the present invention having the following physical data.

TLC: Rf 0.20(Chloroform:Methanol:Water=65:35:8);

NMR(CD$_3$OD): δ7.96(brs, 1H), 7.80(dt, J=7.5,1.2 Hz, 1H), 7.42(brd, J=7.5 Hz, 1H), 7.26(t, J=7.5 Hz, 1H), 4.98–4.94(m, 1H), 4.04–3.90(m, 2H), 2.38–2.20(m, 2H), 1.65–1.54(m, 2H), 1.34–1.22(m, 8H), 0.90–0.86(m, 3H).

Example 42(1)

2-(3-Carboxymethylphenyl)-2-octanoylaminoethylphosphate Trisodium Salt

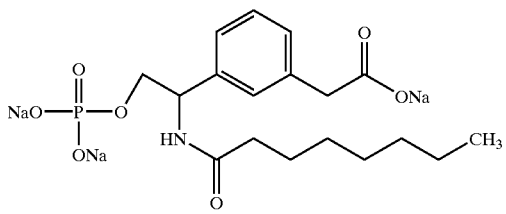

The compound of the present invention having the following physical data was obtained by the same procedure as Example 42, using the compound prepared in Example 36(2) instead of the compound prepared in Example 36(6).

TLC: Rf 0.28(Chloroform:Methanol:Water=65:35:8);

NMR(CD$_3$OD): δ7.26(brs, 1H), 7.18(brs, 3H), 4.92–4.88 (m, 1H), 4.02–3.88(m, 2H), 3.45(s, 2H), 2.34–2.18(m, 2H), 1.66–1.54(m, 2H), 1.36–1.24(m, 8H), 0.90–0.86(m, 3H).

Example 43

(2R)-2-(2-Pentylsulfonylacetyl)amino-2-phenylethylphosphate

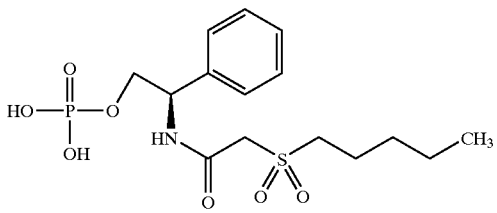

To a solution of the compound prepared in Example 21 (166 mg) in methanol (2.5 ml) was added a solution of potassium peroxomonosulfate (trade mark: oxone)(311 mg) in water (2.5 ml) at 0° C. and the mixture was stirred 3 hours at 0° C. and then stirred for 15 hours at room temperature. The reaction mixture was filtered and the filtrate was concentrated. The residue was washed with methanol and then concentrated. To the residue was added ethyl acetate. The mixture was washed with 1N hydrochloric acid, dried over anhydrous magnesium sulfate and then concentrated to give the compound (132 mg) of the present invention having the following physical data.

TLC: Rf 0.16(Chloroform:Methanol:Water=65:25:4).

Example 44

(2R)-2-(2-Pentylsulfonylacetyl)amino-2-phenylethylphosphate Disodium Salt

The compound of the present invention having the following physical data was obtained by the same procedure as Example 8, using the compound prepared in Example 43 instead of the compound prepared in Example 7.

TLC: Rf 0.16(Chloroform:Methanol:Water=65:25:4);

NMR(CD$_3$OD): δ7.40(brd, J=7.2 Hz, 2H), 7.30–7.15(m, 3H), 4.91 (dd, J=8.1, 3.9 Hz, 1H), 4.05–3.90(m, 2H), 3.17(m, 2H), 1.78(m, 2H), 1.45–1.30(m, 4H), 0.89(brt, J=7.2 Hz, 3H).

Example 45

(2R)-2-(4-Hydroxyphenyl)-2-octanoylaminoethylphosphate Disodium Salt

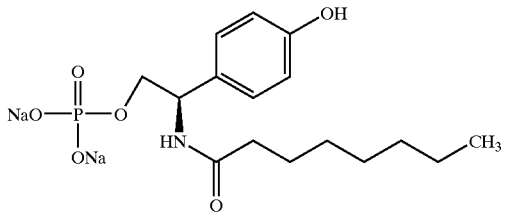

The compound of the present invention having the following physical data was obtained by the same procedure as a series of reactions of Reference example 3→Reference example 14→Example 26→Example 11→Example 8, using (2R)-2-amino-2-(4-benzyloxyphenyl)ethanol instead of (2R)-2-amino-2-phenylethanol.

TLC: Rf 0.26(Chloroform:Methanol:Water=65:35:8);

NMR(CD$_3$OD): δ7.14(d, J=8.4 Hz, 2H), 6.68(d, J=8.4 Hz, 2H), 4.82(dd, J=8.1, 4.8 Hz, 1H), 3.95–3.86(m, 2H), 2.35–2.16(m, 2H), 1.66–1.52(m, 2H), 1.35–1.25(m, 8H), 0.91–0.86(m, 3H).

Example 46

Diphenyl-(1S,2R)-2-methoxyphenyl-1-methyl-2-octanoylaminoethylphosphate

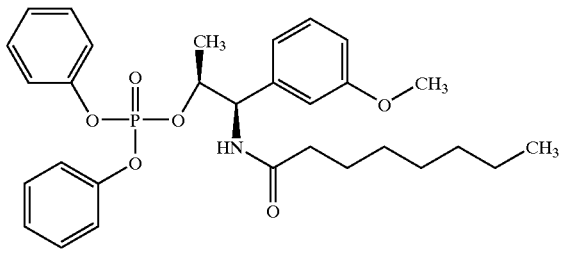

The compound of the present invention having the following physical data was obtained by the same procedure as Example 1, using (1S,2R)-2-(3-methoxyphenyl)-1-methyl-2-octanoylaminoethanol instead of the compound prepared in Reference example 1.

TLC: Rf 0.47 (n-Hexane:Ethyl acetate=1:1);

NMR (CDCl$_3$): δ7.34 (m, 4H), 7.24–7.15 (m, 7H), 6.88–6.74 (m, 3H), 6.69 (d, J=8.1Hz, 1H), 5.10–4.98 (m, 2H), 3.76 (s, 3H), 2.08 (m, 2H), 1.60–1.46 (m, 2H), 1.34–1.14 (m) and 1.24 (d, J=6.3 Hz) total 11H, 0.85 (t, J=6.6 Hz, 3H).

Formulation Example

Formulation Example 1

The following components were admixed in conventional method and punched out to obtain 100 tablets each containing 5 mg of active ingredient.

| | |
|---|---|
| (R)-2-(N-octanoylamino)-2-phenylethylphosphate disodium salt (the compound prepared in Example 8) | 500 mg |
| Carboxymethyl Cellulose calcium | 200 mg |
| Magnesium stearate | 100 mg |
| Microcrystalline cellulose | 9.2 g |

What is claimed is:
1. Phosphoric acid derivatives of the formula (I)

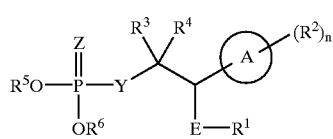

(I)

wherein R$^1$ is
(1) C1–20 alkyl,
(2) C1–20 alkyl which one carbon atom is replaced by an oxygen atom, a sulfur atom, —S(O)— or S(O)$_2$— (with the proviso that, a carbon atom which attached with E is not replaced by these groups),
(3) C2–20 alkenyl,
(4) C2–20 alkynyl,
(5) Cyc$^1$ (wherein Cyc$^1$ is C5–15 membered mono-, bi- or tricarbocyclic ring or 5–15 membered mono-, bi- or tricyclic hetero ring containing 1–4 nitrogen atoms, 1–2 oxygen atoms and/or one sulfur atom),
(6) C1–20 alkyl, C2–20 alkenyl or C2–20 alkynyl substituted by Cyc$^1$ (wherein all symbols are the same meaning as hereinbefore defined), Cyc$^1$ may be substituted by one or more substituents selected from the following (a)–(r):
 (a) C1–8 alkyl,
 (b) C1–8 alkoxy,
 (c) nitro,
 (d) halogen atom,
 (e) trfluoromethyl,
 (f) trifluoromethyloxy,
 (g) hydroxy,
 (h) cyano,
 (i) NR$^{10}$R$^{11}$ (wherein R$^{10}$ and R$^{11}$ each, independently, is a hydrogen atom, C1–8 alkyl, C1–8 hydroxyalkyl, C2–5 acyl or C1–8 alkylsulfonyl),
 (j) COOR$^{20}$ (wherein R$^{20}$ is a hydrogen atom or C1–4 alkyl),
 (k) CONR$^{30}$R$^{31}$ (wherein R$^{30}$ and R$^{31}$ each, independently, is a hydrogen atom or C1–4 alkyl),
 (l) —S(O)$_m$—R$^{32}$ (wherein m is 0, 1 or 2, R$^{32}$ is 1–8 alkyl or C1–8 alkyl substituted by C1–8 alkoxy, COOR$^{20}$ (wherein R$^{20}$ is the same meaning as hereinbefore defined) or CONR$^{30}$R$^{31}$ (wherein R$^{30}$ and R$^{31}$ each, independently, is a hydrogen atom or C1–4 alkyl)),
 (m) —O—Cyc$^2$ (wherein Cyc$^2$ is C3–8 cycloalkyl or phenyl),
 (n) —S—Cyc$^2$ (wherein Cyc$^2$ is the same meaning as hereinbefore defined),
 (o) C1–8alkyl substituted by one substituent selected from C1–8 alkoxy, COOR$^{20}$ (wherein R$^{20}$ is the same meaning as hereinbefore defined), CONR$^{30}$R$^{31}$ (wherein R$^{30}$ and R$^{31}$ are the same meaning as hereinbefore defined), phenyl or hydroxy, (p) C1–8alkoxy substituted by one substituent selected from C1–8 alkoxy, COOR$^{20}$ (wherein R$^{20}$ is the same meaning as hereinbefore defined), CONR$^{30}$R$^{31}$ (wherein R$^{30}$ and R$^{31}$ are the same meaning as hereinbefore defined), phenyl or hydroxy.

(q) C3–15 membered mono-, bi- or tricarbocyclic ring, (r) 5–15 membered mono-, bi- or tricyclic hetero ring containing 1–4 nitrogen atoms, 1–2 oxygen atoms and/or one sulfur atom, E is
(a) —NR$^7$CO—,
(b) —NR$^7$SO$_2$—,
(c) —NR$^7$CONR$^8$—,
(d) —NR$^7$COO—,
(e) —CONR$^7$—,
(f) —NR$^7$CS—,
(g) —NR$^7$CSNR$^8$—,
(h) —NR$^7$CS—O—,
(i) —CSNR$^7$— or
(j) —NR$^7$— (wherein R$^7$ and R$^8$ each, independently, is a hydrogen or C1–4 alkyl), A ring is C3–15 membered mono-, bi- or tricarbocyclic ring or 5–15 membered mono-, bi- or trycyclic hetero ring containing 1–4 nitrogen atoms, 1–2 oxygen atoms and/or one sulfur atom, R$^2$ is the same meaning as hereinbefore defined substituents (a)–(r), R$^3$ and R$^4$
 i) each, independently, is a hydrogen atom, C1–8 alkyl, C1–8 alkoxy, C1–8 hydroxyalkyl or phenyl, or
 ii) taken together represents C2–6 alkylene, or
 iii) one of R$^3$ or R$^4$, taken together with R$^2$, represent C1–5 alkylene, and the other one is a hydrogen atom, C1–8alkyl or C1–8alkoxy, n is an integer of 0, 1 or more, R$^5$ and R$^6$ each, independently, is a hydrogen atom, C1–8 alkyl, phenyl, C1–4 alkyl substituted by phenyl, C1–4 alkyl substituted by cyano or C1–4 alkyl substituted by trihalomethyl, Y and Z each, independently, is an oxygen atom or a sulfur atom.

with the proviso that,
(1) when n is 2 or more integer, then R$^2$ is the same or different,
(2) when R$^1$ and R$^2$ contains a sulfur atom, then Y is an oxygen atom, and R$^1$ and R$^2$ do not contains a sulfur atom at the same time or a non-toxic salt thereof.

2. A compound according to claim 1, wherein A ring is C3–15 membered mono-, bi- or tricarbocyclic ring.

3. A compound according to claim 1, wherein A ring is 3–4 membered monocyclichetero ring containing 1–4 nitrogen atoms, 1–2 oxygen atoms and/or one sulfur atom.

4. A compound according to claim 1, wherein A ring is 5–7 membered monocyclic hetero ring containing 1–4 nitrogen atoms, 1–2 oxygen atoms and/or one sulfur atom.

5. A compound according to claim 1, wherein A ring is 8–15 membered monocyclic hetero ring containing 1–4 nitrogen atoms, 1–2 oxygen atoms and/or one sulfur atom.

6. A compound according to claim 1, wherein A ring is 8–15 membered bi- or tricyclic hetero ring.

7. A compound according to claim 1, wherein both R$^5$ and R$^6$ are hydrogen.

8. A compound according to claim 1, wherein R$^5$ and R$^6$ each, independently, is C1–8 alkyl, phenyl, C1–4 alkyl substituted by phenyl, C1–4 alkyl substituted by cyano or C1–4 alkyl substituted by trihalomethyl.

9. A compound according to claim 1, wherein one of R$^5$ or R$^6$ is a hydrogen, and the other is C1–8 alkyl, phenyl, C1–4 alkyl substituted by phenyl, C1–4 alkyl substituted by cyano or C1–4 alkyl substituted by trihalomethyl.

10. A compound according to claim 2, which is (1) Diphenyl-(2R)-2-t-butoxycarbonylamino-2-phenylethylphosphate,
(2) Diphenyl-(2R)-2-N-octanoylamino-2-phenylethylphosphate,
(3) Phenyl-(2R)-2-octanoylamino-2-phenylethylphosphate,
(4) (2R)-2-Octanoylamino-2-cyclohexylethylphosphate,
(5) Bis(2,2,2-trichloroethyl)-(2R)-2-t-butoxycarbonylamino-2-phenylethylphosphate,
(6) Bis(2,2,2-trichloroethyl)-(2R)-2-octanoylamino-2-phenylethylphosphate,
(7) (2R)-2-Octanoylamino-2-phenylethylphosphate,
(8) (2S)-2-Octanoylamino-2-phenylethylphosphate,
(9) 1-Methyl-2-nonanoylamino-2-phenylethylphosphate,
(10) 1-Methyl-2-octanoylamino-2-phenylethylphosphate,
(11) 2-Octanoylamino-2-phenyl-1,1-propanoethylphosphate,
(12) (1S,2R)-1-Methyl-2-octanoylamino-2-phenylethylphosphate,
(13) (1R,2S)-1-Methyl-2-octanoylamino-2-phenylethylphosphate,
(14) (1R,2R)-1-Methyl-2-octanoylamino-2-phenylethylphosphate,
(15) (1S,2S)-1-Methyl-2-octanoylamino-2-phenylethylphosphate,
(16) Dibenzyl-(1R,2R)-1-octanoylaminoindan-2-ylphosphate,
(17) (1R,2R)-1-Octanoylaminoindan-2-ylphosphate,
(18) (1R,2R)-1-Octanoylaminoindan-2-ylphosphate,
(19) (1R,2S)-1-Octanoylaminoindan-2-ylphosphate,
(20) Dibenzyl-(2R)-2-(5-phenylpentanoylamino)-2-phenylethylphosphate,
(21) (2R)-2-(5-Phenylpentanoylamino)-2-phenylethylphosphate,
(22) (2R)-2-Nonanoylamino-2-phenylethylphosphate,
(23) (2R)-2-Decanoylamino-2-phenylethyl phosphate,
(24) (2R)-2-Undecanoylamino-2-phenylethylphosphate,
(25) 2-Heptylaminocarbonyl-2-phenylethylphosphate,
(26) (2R)-2-Propionylamino-2-phenylethylphosphate,
(27) (2R)-2-Butyrylamino-2-phenylethylphosphate,
(28) (2R)-2-Pentanoylamino-2-phenylethylphosphate,
(29) (2R)-2-Hexanoylamino-2-phenylethylphosphate,
(30) (2R)-2-Heptanoylamino-2-phenylethylphosphate,
(31) (2R)-2-Cyclopropylcarbonylamino-2-phenylethylphosphate,
(32) (2R)-2-t-Butylcarbonylamino-2-phenylethylphosphate,
(33) (2R)-2-Acetylamino-2-phenylethylphosphate,
(34) (2R)-2-Ethoxycarbonylamino-2-phenylethylphosphate,
(35) (2R)-2-(N-Methyl-N-octanoylamino)-2-phenylethylphosphate,
(36) (2R)-2-Hexyloxycarbonylamino-2-phenylethylphosphate,
(37) (2R)-2-(2,2-Dimethyloctanoylamino)-2-phenylethylphosphate,
(38) (2R)-2-(2,2-Propanooctanoylamino)-2-phenylethylphosphate,
(39) (2R)-2-(2-Methyloctanoylamino)-2-phenylethylphosphate,
(40) (2R)-2-Benzoylamino-2-phenylethylphosphate,
(41) (2R)-2-t-Butoxycarbonylamino-2-phenylethylphosphate,

(42) (2R)-2-Octylsulfonylamino-2-phenylethylphosphate,
(43) (2R)-2-(N'-Hexylureido)-2-phenylethylphosphate,
(44) (2R)-2-Phenyl-2-(4-propyloxybutanoyl)aminoethylphosphate,
(45) (2R)-2-(6-Methoxyhexanoyl)amino-2-phenylethylphosphate,
(46) (2R)-2-Phenyl-2-(2-propylvaleryl)aminoethylphosphate,
(47) (2R)-2-(2-Pentyloxyacetyl)amino-2-phenylethylphosphate,
(48) (2R)-2-(5-Ethoxyvaleryl)amino-2-phenylethylphosphate,
(49) (1S,2R)-2-Heptanoylamino-1-methyl-2-phenylethylphosphate,
(50) (1S,2R)-1-Methyl-2-nonanoylamino-2-phenylethylphosphate,
(51) 2-(4-Methoxyphenyl)-2-octanoylaminoethylphosphate,
(52) 2-(3-Methoxyphenyl)-2-octanoylaminoethylphosphate,
(53) 2-(2-Methoxyphenyl)-2-octanoylaminoethylphosphate,
(54) 2-(2-Methylphenyl)-2-octanoylaminoethylphosphate,
(55) 2-(3-Methylphenyl)-2-octanoylaminoethylphosphate,
(56) 2-(4-Methylphenyl)-2-octanoylaminoethylphosphate,
(57) 2-(Naphthalen-1-yl)-2-octanoylaminoethylphosphate,
(58) 2-(Naphthalen-2-yl)-2-octanoylaminoethylphosphate,
(59) 2-Octanoylamino-2-(4-trifluoromethylphenyl)ethylphosphate,
(60) 2-Octanoylamino-2-(2-trifluoromethylphenyl)ethylphosphate,
(61) 2-(3,5-Dimethoxyphenyl)-2-octanoylaminoethylphosphate,
(62) 2-(3-Fluorophenyl)-2-octanoylaminoethylphosphate,
(63) 2-(3-Ethoxyphenyl)-2-octanoylaminoethylphosphate,
(64) 2-Octanoylamino-2-(3-propyloxyphenyl)ethylphosphate,
(65) 2-(3-Isopropyloxyphenyl)-2-octanoylaminoethylphosphate,
(66) 2-Octanoylamino-2-(3-trifluoromethylphenyl)ethylphosphate,
(67) (2R)-2-(3-Methoxyphenyl)-2-octanoylaminoethylphosphate,
(68) 2-Heptanoylamino-2-(3-methoxyphenyl)ethyphosphate,
(69) 2-Hexanoylamino-2-(3-methoxyphenyl)ethylphosphate,
(70) 2-(3-Methoxyphenyl)-2-valerylaminoethylphosphate,
(71) 2-(3-(2-Methoxyethoxy)phenyl)-2-octanoylaminoethylphosphate,
(72) 2-(3-Butoxyphenyl)-2-octanoylaminoethylphosphate,
(73) 2-Octanoylamino-2-(3-pentyloxyphenyl)ethylphosphate,
(74) 2-(3-Hexyloxyphenyl)-2-octanoylaminoethylphosphate,
(75) 2-(3-Methoxymethylphenyl)-2-octanoylaminoethylphosphate,
(76) 2-(3-Cyclopentyloxyphenyl)-2-octanoylamnoethylphosphate,
(77) 2-(3-(2-Methylpropyloxy)phenyl)-2-octanoylaminoethylphosphate,
(78) 2-Acetylamino-2-(3-methoxyphenyl)ethylphosphate,
(79) 2-octanoylamino-2-(3-trifluoromethyloxyphenyl)ethylphosphate,
(80) 2-(3-Dimethylaminocarbonylmethyloxyphenyl)-2-octanoylaminoethylphosphate,
(81) (2S)-2-(3-methoxyphenyl)-2-octanoylaminoethylphosphate,
(82) 2-(3-Cyclobutyloxyphenyl)-2-octanoylaminoethylphosphate,
(83) 2-(3-(1-Ethylpropyloxy)phenyl)-2-octanoylaminoethylphosphate,
(84) 2-(3-Methoxymethoxyphenyl)-2-octanoylaminoethylphosphate,
(85) (1S,2R)-2-(3-Methoxyphenyl)-1-methyl-2-octanoylaminoethylphosphate,
(86) (1S,2R)-2-(3-Isopropyloxyphenyl)-1-methyl-2-octanoylaminoethylphosphate,
(87) (1R,2R)-2-(3-Methoxyphenyl)-1-methyl-2-octanoylaminoethylphosphate,
(88) (1R,2S)-2-(3-Methoxyphenyl)-1-methyl-2-octanoylaminoethylphosphate,
(89) (1S,2S)-2-(3-Methoxyphenyl)-1-methyl-2-octanoylaminoethylphosphate,
(90) Di-t-butyl-(2R)-2-pentylthioacetylamino-2-phenylethylphosphate,
(91) (2R)-2-Pentylthioacetylamino-2-phenylethylphosphate,
(92) (2R)-2-Pentylthioacetylamino-2-phenylethylphosphate,
(93) 2-(4-Chlorophenyl)-2-octanoylaminoethylphosphate,
(94) (1S,2R -1-Methyl-2-(2-pentylthioacetyl)amino-2-phenylethylphosphate,
(95) 2-(3-Chorophenyl)-2-octanoylaminoethylphosphate,
(96) 2-(2-Chlorophenyl)-2-octanoylaminoethylphosphate,
(97) 2-(3-Methylthiophenyl)-2-octanoylaminoethylphosphate,
(98) 2-(3-Methylsulfonyphenyl)-2-octanoylaminoethylphosphate,
(99) 2-(3-Isopropylthiophenyl)-2-octanoylaminoethylphosphate,
(100) (2R)-Bis(2-cyanoethyl)-2-octanoylamino-2-phenylethylthiophosphate,
(101) (2R)-2-Octanoylamino-2-phenylethylthiophosphoric acid,
(102) (1S,2R)-[Bis(2-cyanoethyl)]-1,2-diphenyl-2-octanoylaminoethylphosphate,
(103) (1S,2R)-2-Octanoylamino-1,2-diphenylethylphosphate,
(104) 2-Octanoylamino-2-(3-benzyloxyphenyl)ethylphosphate,
(105) Diethyl-(2R)-S-(2-t-butoxycarbonylamino-2-phenyl)ethanephosphorothioate,
(106) (2R)-S-(2-Octanoylamino-2-phenylethyl)-O,O'-diethylphosphorothioate,
(107) (2R)-S-(2-Octanoylamino-2-phenylethyl)phosphorothioate,
(108) 2-(3-Hydroxyphenyl)-2-octanoylaminoethylphosphate,
(109) 2-(3-Hydroxymethylphenyl)-2-octanoylaminoethylphosphate,
(110) (1S,2R)-2-(3-Hydroxymethylphenyl)-1-methyl-2-octanoylaminoethylphosphate,
(111) 2-(3-Ethoxycarbonylmethoxyphenyl)-2-octanoylaminoethylphosphate,
(112) (1S,2R)-2-(3-Methoxycarbonylphenyl)-1-methyl-2-octanoylaminoethylphosphate,
(113) 2-(3-Methoxycarbonylmethylphenyl)-2-octanoylaminoethylphosphate,
(114) 2-(3-Methoxyphenyl)-1,1-dimethyl-2-octanoylaminoethylphosphate,
(115) 2-(3-Methylsulfonylaminophenyl)-2-octanoylaminoethylphosphate,
(116) (1S,2R)-2-(3-Methoxycarbonylmethylphenyl)-1-methyl-2-octanoylaminoethylphosphate,
(117) 2-(3-Methoxycarbonylphenyl)-2-octanoylaminoethylphosphate, (118) (1S,2R)-2-Hexyloxycarbonylamino-1-methyl-2-(3-methoxyphenyl)ethylphosphate,
(119) (1S,2R)-2-Hexyloxycarbonylamino-1-methyl-2-phenylethylphosphate,
(120) (1S,2R)-2-Hexyloxycarbonylamino-1-methyl-2-(3-isopropyloxyphenyl)ethylphosphate,
(121) (1S,2R)-2-Hexyloxycarbonylamino-2-(3-methoxycarbonylphenyl)1-methylethylphosphate,
(122) (1S,2R)-1-Methyl-2-(3-methylthiophenyl)-2-octanoylaminoethylphosphate,
(123) (1S,2R)-2-Hexyloxycarbonylamino-1-methyl-2-(3-methylthiophenyl)ethylphosphate,
(124) (1R,2R)-1-Hydroxymethyl-2-octanoylamino-2-phenylethylphosphate,
(125) 2-(3-Carboxyphenyl)-2-octanoylaminoethylphosphate,
(126) 2-(3-Carboxymethylphenyl)-2-octanoylaminoethylphosphate,
(127) (2R)-2-(2-Pentylsulfonylacetyl)amino-2-phenylethylphosphate,
(128) (2R)-2-(4-Hydroxyphenyl)-2-octanoylaminoethylphosphate or
(129) Diphenyl-(1S,2R)-2-(3-methoxyphenyl)-1-methyl-2-octanoylaminoethylphosphate, or a non-toxic salt thereof.

11. A compound according to claim 4, which is (1) 2-(1,3-Dioxaindan-5-yl)-2-octanoylaminoethylphosphate or
(2) 2-(1,3-Dioxaindan-4-yl)-2-octanoylaminoethylphosphate, or a non-toxic salt thereof.

12. A compound according to claim 5, which is (1) 2-Octanoylamino-2-(thiophen-2-yl)ethylphosphate,
(2) 2-Octanoylamino-2-(pyridin-2-yl)ethylphosphate or
(3) 2-Octanoylamino-2-(pyridin-3-yl)ethylphosphate, or a non-toxic salt thereof.

13. A TNFa production inhibitor, which comprises a phosphoric acid derivative having the formula (I) depicted in claim 1 or non-toxic salt thereof.

14. A compound for the prevention and/or treatment of rheumatoid arthritis, ulcerative colitis, Crohn's disease, hepatitis, sepsis, hemorrhagic shock, multiple sclerosis, cerebral infarction, diabetes, interstitial pneumonia, uveitis, pain, glomerulonephritis, HIV-associated diseases, cachexia, myocardial infarction, chronic heart failure, oral aphtha, Hansen's disease, infection, which comprises a phosphoric acid derivative having the formula (I) depicted in claim 1 or non-toxic salt thereof.

15. A pharmaceutical composition which comprises, as an active ingredient, a phosphoric acid derivative having the formula (I) depicted in claim 1 or a non-toxic salt thereof.

* * * * *